(12) United States Patent
Evans et al.

(10) Patent No.: US 7,307,090 B2
(45) Date of Patent: Dec. 11, 2007

(54) PIPERIDINE DERIVATIVES USEFUL AS MODULATORS OF CHEMOKINE RECEPTOR ACTIVITY

(75) Inventors: Richard Evans, Loughborough (GB); Matthew Perry, Loughborough (GB); Brian Springthorpe, Loughborough (GB)

(73) Assignee: AstraZeneca AB, Södertälje (SE)

( * ) Notice: Subject to any disclaimer, the term of this patent is extended or adjusted under 35 U.S.C. 154(b) by 254 days.

(21) Appl. No.: 10/480,625

(22) PCT Filed: Jul. 1, 2002

(86) PCT No.: PCT/SE02/01311

§ 371 (c)(1),
(2), (4) Date: Dec. 12, 2003

(87) PCT Pub. No.: WO03/004487

PCT Pub. Date: Jan. 16, 2003

(65) Prior Publication Data

US 2004/0235894 A1    Nov. 25, 2004

(30) Foreign Application Priority Data

Jul. 2, 2001 (GB) .................... 0116179.3
Sep. 25, 2001 (GB) .................... 0123037.4

(51) Int. Cl.
*A61K 31/445* (2006.01)
*C07D 401/00* (2006.01)

(52) U.S. Cl. ............... 514/316; 514/235.5; 544/129; 546/187

(58) Field of Classification Search ............... 514/317, 514/235.5, 316; 546/186, 187; 544/129
See application file for complete search history.

(56) References Cited

U.S. PATENT DOCUMENTS

| | | | |
|---|---|---|---|
| 4,695,575 A | 9/1987 | Janssens et al. | |
| 5,883,096 A | 3/1999 | Lowe et al. | 514/17 |
| 5,889,006 A | 3/1999 | Lowe et al. | 514/252.02 |
| 5,952,349 A | 9/1999 | Asberom et al. | 514/316 |
| 5,977,138 A | 11/1999 | Wang et al. | |
| 6,066,636 A | 5/2000 | Kozlowski et al. | |
| 6,387,930 B1 | 5/2002 | Baroudy et al. | |
| 6,440,440 B1 | 8/2002 | Meerpoel et al. | 424/405 |
| 6,759,411 B2 | 7/2004 | Ko et al. | 514/235.5 |
| 6,903,115 B2 | 6/2005 | Rigby et al. | 514/316 |

FOREIGN PATENT DOCUMENTS

| | | |
|---|---|---|
| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| GB | 1250719 | 10/1971 |
| WO | WO93/10091 | 5/1993 |
| WO | WO95/08535 | 3/1995 |
| WO | WO96/26196 | 8/1996 |
| WO | WO96/34857 | 11/1996 |
| WO | WO96/41631 | 12/1996 |
| WO | WO97/24324 | 7/1997 |
| WO | WO98/01425 | 1/1998 |
| WO | WO98/05291 | 2/1998 |
| WO | WO 98/05292 | 2/1998 |
| WO | WO98/05292 | 2/1998 |
| WO | WO 98/06697 | 2/1998 |
| WO | WO98/06697 | 2/1998 |
| WO | WO98/11128 | 3/1998 |
| WO | WO99/04794 | 2/1999 |
| WO | WO99/37304 | 7/1999 |
| WO | WO99/38514 | 8/1999 |
| WO | WO99/51578 | 10/1999 |
| WO | WO 00/00488 | 1/2000 |
| WO | WO 00/12478 | 3/2000 |
| WO | WO 00/32590 | 6/2000 |
| WO | WO 00/35877 | 6/2000 |
| WO | WO 00/66559 | 11/2000 |
| WO | WO 01/02381 | 1/2001 |

(Continued)

OTHER PUBLICATIONS

Cohen et al., Am. J. Clin. Pathol., 1996, 105, 589.*
Patani et al., Chem. Rev., 1996, 96, pp. 3147-3176.*
U.S. Appl. No. 10/341,027, filed Jan. 8, 2004, Lawrence et al.
Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *Psychopharmacology* 106 (Suppl.).

(Continued)

*Primary Examiner*—Celia Chang
(74) *Attorney, Agent, or Firm*—Fish & Richardson P.C.

(57) ABSTRACT

The invention provides a compound of formula (I), wherein: T is C(O) or S(O)$_2$; W is C(O) or S(O)$_2$; X is CH$_2$, O or NH; Y is CR$^5$ or N; R$^1$ is optionally substituted aryl or optionally substituted heterocyclyl; R$^2$ is hydrogen or C$_{1-6}$alkyl; R$^3$ is hydrogen or optionally substituted C$_{1-6}$alkyl; and R$^4$ is alkyl, optionally substituted aryl, optionally substituted aralkyl or optionally substituted heterocyclyl; that are modulators of chemokine (especially CCR3) activity and are especially useful for treating asthma and/or rhinitis

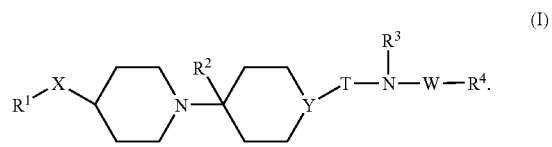

9 Claims, No Drawings

FOREIGN PATENT DOCUMENTS

| | | |
|---|---|---|
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/079190 | 10/2002 |
| WO | WO 02/079194 | 10/2002 |
| WO | WO 02/081449 | 10/2002 |
| WO | WO 03/018576 | 3/2003 |
| WO | WO 03/020716 | 3/2003 |
| WO | WO 03/024962 | 3/2003 |
| WO | WO 03/078395 | 9/2003 |
| WO | WO 03/078421 | 9/2003 |
| WO | WO 2004/029041 | 4/2004 |
| WO | WO 2004/085423 | 10/2004 |
| WO | WO 2004/087659 | 10/2004 |
| WO | WO 2004/099144 | 11/2004 |
| WO | WO 2004/113323 | 12/2004 |

OTHER PUBLICATIONS

Hermans et al., "4-Substituted Piperidines. II. Reaction of 1-Benzyl-4-cyano-4-*t*-aminopiperidines with Organometallic Compounds", *J. Med. Chem.* 8(6):851-855 (1965) at p. 852 ("compound 12"in Table I).

STN International, File Caplus, Caplus accession No. 1988:630911, Document No. 109:230911, Lehmann, Jochen et al: "Lactones. XVIII. Synthesis of lactone-bridged 1,1-diarylpropanamines"; & *Arch. Pharm.* (Weinheim, Ger.) (1988), 321(7), 443-445.

Harada et al., Novel N-[1-Substituted 4-Piperidinylmethyl)-4-piperidinyl] benzamides as potent Colonic Prokinetic Agents, Bioorganic & Medicinal Chemistry Letters 12:967-970, 2002.

\* cited by examiner

PIPERIDINE DERIVATIVES USEFUL AS MODULATORS OF CHEMOKINE RECEPTOR ACTIVITY

CROSS-REFERENCE TO RELATED APPLICATIONS

This application is the national phase application under 35 U.S.C. § 371 of PCT International Application No. PCT/SE02/01311, which has an International filing date of Jul. 1, 2002, and which designated United Kingdom Application Serial No. 0116179.3, filed Jul. 2, 2001, and United Kingdom application Ser. No. 0123037.4, filed Sep. 25, 2001, as priority applications. The contents of all these applications are incorporated by reference in their entirety.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/35877.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria. Antagonists of H1 are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The present invention provides a compound of formula (I):

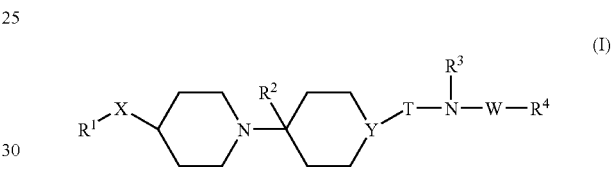

wherein:
T is C(O) or S(O)$_2$;
W is C(O) or S(O)$_2$;
X is CH$_2$, O or NH;
Y is CR$^5$ or N;
R$^1$ is optionally substituted aryl or optionally substituted heterocyclyl;
R$^2$ is hydrogen or C$_{1-6}$ alkyl;
R$^3$ is hydrogen or optionally substituted C$_{1-6}$ alkyl;
R$^4$ is alkyl, cycloalkyl, optionally substituted aryl, optionally substituted aralkyl or optionally substituted heterocyclyl;
R$^5$ is hydrogen or C$_{1-6}$ alkyl;
wherein the foregoing aryl and heterocyclyl moieties are optionally substituted by: halogen, cyano, nitro, hydroxy, oxo, S(O)$_p$R$^{25}$, OC(O)NR$^6$R$^7$, NR$^8$R$^9$, NR$^{10}$C(O)R$^{11}$, NR$^{12}$C(O)NR$^{13}$R$^{14}$, S(O)$_2$NR$^{15}$R$^{16}$, NR$^{17}$S(O)$_2$R$^{18}$, C(O)NR$^{19}$R$^{20}$, C(O)R$^{21}$, CO$_2$R$^{22}$, NR$^{23}$CO$_2$R$^{24}$, C$_{1-6}$ alkyl, CF$_3$, C$_{1-6}$ alkoxy(C$_{1-6}$)alkyl, C$_{1-6}$ alkoxy, OCF$_3$, C$_{1-6}$ alkoxy(C$_{1-6}$)alkoxy (preferably not forming an acetal), C$_{1-6}$ alkylthio, C$_{2-6}$ alkenyl, C$_{2-6}$ alkynyl, C$_{3-10}$ cycloalkyl (itself optionally substituted by C$_{1-4}$ alkyl or oxo), methylenedioxy, difluoromethylenedioxy, phenyl, phenyl(C$_{1-4}$)alkyl, phenoxy, phenylthio, phenyl(C$_{1-4}$)alkoxy, heteroaryl, heteroaryl(C$_{1-4}$)alkyl, heteroaryloxy or heteroaryl(C$_{1-4}$)alkoxy; wherein any of the immediately foregoing phenyl and heteroaryl moieties are optionally substituted with halogen, hydroxy, nitro, S(O)$_q$(C$_{1-4}$ alkyl), S(O)$_2$NH$_2$, cyano, C$_{1-4}$ alkyl, C$_{1-4}$ alkoxy, C(O)NH$_2$, C(O)NH(C$_{1-4}$ alkyl), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$;
p and q are, independently, 0, 1 or 2;
R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{19}$, R$^{20}$, R$^{21}$, R$^{22}$, and R$^{23}$ are, independently, hydrogen, C$_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2$ $NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2$ $(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

alternatively $NR^6R^7$, $NR^8R^9$, $NR^{13}R^{14}$, $NR^{15}R^{16}$, $NR^{19}R^{20}$ or $N(C_{1-4}$ alkyl)$_2$ may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen; $R^{25}$, $R^{18}$ and $R^{24}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^6$ and $R^7$ above), $S(O)_2(C_{1-4}$ alkyl), $S(O)_2$ $NH_2$, $S(O)_2NH(C_{1-4}$ alkyl), $S(O)_2N(C_{1-4}$ alkyl)$_2$ (and these alkyl groups may join to form a ring as described for $R^6$ and $R^7$ above), cyano, $C_{1-4}$ alkyl, $C_{1-4}$ alkoxy, $C(O)$ $NH_2$, $C(O)NH(C_{1-4}$ alkyl), $C(O)N(C_{1-4}$ alkyl)$_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^6$ and $R^7$ above), $S(O)_2(C_{1-4}$ alkyl), $S(O)_2$ $NH_2$, $S(O)_2NH(C_{1-4}$ alkyl), $S(O)_2N(C_{1-4}$ alkyl)$_2$ (and these alkyl groups may join to form a ring as described for $R^6$ and $R^7$ above), cyano, $C_{1-4}$ alkyl, $C_{1-4}$ alkoxy, $C(O)$ $NH_2$, $C(O)NH(C_{1-4}$ alkyl), $C(O)N(C_{1-4}$ alkyl)$_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate. Salts also include metal salts, such as alkali metal salts (for example a sodium salt).

The compounds of the invention may exist as solvates (such as hydrates) and the present invention covers all such solvates.

Halogen includes fluorine, chlorine, bromine and iodine.

Alkyl groups and moieties (including those of alkoxy) are straight or branched chain and are, for example, methyl, ethyl, n-propyl, 1-methylethyl or 1,1-dimethylethyl.

Alkenyl is, for example, vinyl or allyl.

Alkynyl is, for example, propargyl.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system).

Haloalkyl is preferably $CF_3$. Haloalkoxy is preferably $OCF_3$.

Aryl is preferably phenyl or naphthyl.

Arylalkyl is preferably aryl($C_{1-4}$ alkyl) for example benzyl or 2-phenyleth-1-yl.

Heterocyclyl is an aromatic or non-aromatic 5 or 6 membered ring, optionally fused to one or more other rings, comprising at least one heteroatom selected from the group comprising nitrogen, oxygen and sulfur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1,1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8] naphthyridinyl or in 1H-[1,8]naphthyridin-4-one-yl), a benzothiazinyl (for example in 4H-benzo[1,4]thiazin-3-one-yl), benzo[d]imidazo[2,1-b]thiazol-2-yl or dibenzothiophenyl (also known as dibenzothienyl); or an N-oxide thereof (such as a pyridine N-oxide), or an S-oxide or S-dioxide thereof.

An N-oxide of a compound of formula (I) is, for example, a 1-oxido-[1,4']bipiperidinyl-1'-yl compound.

In one particular aspect the present invention provides a compound of formula (I) wherein: T is $C(O)$ or $S(O)_2$; W is $C(O)$ or $S(O)_2$; X is $CH_2$, O or NH; Y is $CR^5$ or N; $R^1$ is optionally substituted aryl or optionally substituted heterocyclyl; $R^2$ is hydrogen or $C_{1-6}$ alkyl; $R^3$ is hydrogen or optionally substituted $C_1$alkyl; $R^4$ is alkyl; optionally substituted aryl, optionally substituted aralkyl or optionally substituted heterocyclyl; $R^5$ is hydrogen or $C_{1-6}$ alkyl; wherein the foregoing aryl and heterocyclyl moieties are optionally substituted by: halogen, cyano, nitro, hydroxy, oxo, $S(O)_pR^{25}$, $OC(O)NR^6R^7$, $NR^8R^9$, $NR^{10}OC(O)R^{11}$, $NR^{12}C(O)NR^{13}R^{14}$, $S(O)_2NR^{15}R^{16}$, $NR^{17}S(O)_2R^{18}$, $C(O)$ $NR^{19}R^{20}$, $C(O)R^{21}$, $CO_2R^{22}$, $NR^{23}CO_2R^{24}$, $C_{1-6}$ alkyl, $C_{1-6}$ haloalkyl, $C_{1-6}$ alkoxy($C_1$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$) alkyl, phenoxy, phenylthio, phenyl($C_{1-4}$)alkoxy, heteroaryl, heteroaryl($C_{1-4}$)alkyl, heteroaryloxy or heteroaryl($C_{1-4}$) alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; p and q are, independently, 0, 1 or 2; $R^6$, $R^7$, $R^8$, $R^9$, $R^{10}$, $R^{11}$, $R^{12}$, $R^{13}$, $R^{14}$, $R^{13}$, $R^{14}$, $R^{15}$, $R^{16}$, $R^{17}$, $R^{19}R^{20}$, $R^{21}$, $R^{22}$, and $R^{23}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $NH(C_{1-4}$ alkyl)$_2$, $S(O)_2$ $(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)$ $NH_2$, $C(O)NH(C_{1-4}$ alkyl), $C(O)N(C_{1-4}$ alkyl)$_2$, $CO_2H$, $CO_2$ $(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^6R^7$, $NR^8R^9$, $NR^{13}R^{14}$, $NR^{15}R^{16}$, $NR^{19}R^{20}$, may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen; $R^{25}$, $R^{18}$ and $R^{24}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^6$ and $R^7$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^6$ and $R^7$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS$ $(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^6$ and $R^7$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^6$ and $R^7$ above), cyano, $C_{1-4}$ alkyl, $C_{1-4}$ alkoxy, $C(O)NH_2$, $C(O)NH(C_{1-4}$ alkyl), $C(O)N$ $(C_{1-4}$ alkyl)$_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or an N-oxide thereof; or a pharmaceutically acceptable salt thereof;

or a solvate thereof.

In a further aspect X is O.

In another aspect $R^1$ is phenyl substituted with one or more of fluorine, chlorine, $C_{1-4}$ alkyl (especially methyl) or $C_{1-4}$ alkoxy (especially methoxy).

In a further aspect $R^1$ is phenyl optionally substituted (for example with one, two or three of) by halogen (especially fluoro or chloro), $C_{1-4}$ alkyl (especially methyl) or $C_{1-4}$ alkoxy (especially methoxy). In a still further aspect $R^1$ is phenyl substituted by one, two or three of: fluoro, chloro, methyl or methoxy. In another aspect $R^1$ is phenyl optionally substituted by halogen (especially fluoro or chloro), $C_{1-4}$ alkyl (especially methyl); especially optionally substituted (for example independently with one, two or three of, especially two or three of) by fluoro, chloro or methyl. In a still further aspect $R^1$ is 3,4-dichlorophenyl, or, additionally 2-chloro-4-fluorophenyl, 2-methyl-4-chlorophenyl, 2,4-dichloro-3-methylphenyl or 3,4-dichloro-2-methylphenyl.

In another aspect one of T and W is C(O) and the other is $S(O)_2$.

In a still further aspect T is C(O).

In another aspect W is $S(O)_2$.

In yet another aspect of the invention, and when Y is $CR^5$, the compounds of formula (I) are preferably trans in terms of relative stereochemistry, that is, the piperidine ring and the T-N($R^3$)-W—$R^4$ group are both equatorial on the cyclohexane ring.

In a still further aspect of the invention Y is CH or N; especially N.

In yet another aspect $R^2$ is hydrogen or methyl; for example $R^2$ is hydrogen.

In a further aspect $R^3$ is hydrogen or methyl; for example hydrogen.

In a still further aspect $R^4$ is unsubstituted phenyl, monosubstituted phenyl, unsubstituted heterocyclyl or monosubstituted heterocyclyl, the substituents being chosen from those described above.

In a further aspect the present inention provides a compound of formula (I) wherein $R^4$ is aryl (for example phenyl or naphthyl; especially phenyl) optionally substituted by one or more of $C_{1-6}$ alkyl (for example methyl or ethyl), $C_{1-4}$ alkoxy (for example methoxy), halogen (for example chloro or fluoro), $CF_3$, CN, $CO_2(C_{1-4}$ alkyl) (for example $CO_2CH_3$), OH, $OCF_3$, $S(O)_2(C_{1-4}$ alkyl) (for example $S(O)_2$ $CH_3$) or $NR^8R^9$ (wherein $R^8$ and $R^9$ are, independently, hydrogen or $C_{1-4}$ alkyl); or heterocyclyl (for example imidazolyl, thienyl, tetrahydrothienyl, thiazolyl, 1,3,4-thiadiazolyl, pyridyl or dihydroisoquinolinyl) optionally substituted by oxo, halogen (for example chloro or fluoro), $C_{1-4}$ alkyl (for example methyl), $NR^8R^9$ (wherein $R^8$ and $R^9$ are, independently, hydrogen or $C_{1-4}$ alkyl), piperidinyl or morpholinyl. In another aspect $R^4$ is phenyl optionally substituted by one or more of $C_{1-6}$ alkyl (for example methyl or ethyl), $C_{1-4}$ alkoxy (for example methoxy), halogen (for example chloro or fluoro), $CF_3$, CN, $CO_2(C_{1-4}$ allyl) (for example $CO_2CH_3$), OH, $OCF_3$, $S(O)_2(C_{1-4}$ alkyl) (for example $S(O)_2CH_3$) or $NR^8R^9$ (wherein $R^8$ and $R^9$ are, independently, hydrogen or $C_{1-4}$ alkyl).

In a further aspect of the invention $R^4$ is substituted (especially mono-substituted) phenyl, the substituents being chosen from those described above.

In a still further aspect $R^4$ is phenyl or heterocyclyl, either of which is optionally substituted by: halo, hydroxy, nitro, cyano, oxo, amino, $C_{1-4}$ alkyl (itself optionally substituted by $S(O)_2(C_{1-4}$ alkyl), $S(O)_2$phenyl), $C_{1-4}$ alkoxy, $S(O)_kR^{26}$ (wherein k is 0, 1 or 2 (preferably 2); and $R^{26}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), $C_{1-4}$ haloalkylthio, $C(O)$ $NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$.

In yet another aspect $R^4$ is phenyl or heterocyclyl, either of which is optionally substituted by: halo, hydroxy, nitro, cyano, oxo, $NR^8R^9$ (wherein $R^8$ and $R^9$ are, independently, hydrogen or $C_{1-4}$ alkyl), $C_{1-4}$ alkyl (itself optionally substituted by $S(O)_2(C_{1-4}$ alkyl), $S(O)_2$phenyl), $C_{1-4}$ alkoxy, $S(O)_k$ $R^{26}$ (wherein k is 0, 1 or 2 (preferably 2); and $R^{26}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), $C_{1-4}$ haloalkylthio, $C(O)$ $NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$.

In one aspect the variable $R^4$ is phenyl optionally substituted by: halo, hydroxy, nitro, cyano, amino, $C_{1-4}$ alkyl (itself optionally substituted by $S(O)_2(C_{1-4}$ alkyl), $S(O)_2$ phenyl), $C_{1-4}$ alkoxy, $S(O)_kR^{26}$ (wherein k is 0, 1 or 2 (preferably 2); and $R^{26}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), $C_{1-4}$ haloalkylthio, $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$ (and these alkyl groups may join to form a ring as described for $R^6$ and $R^7$ above).

In another aspect the variable $R^4$ is phenyl optionally substituted by: halo, hydroxy, nitro, cyano, $NR^8R^9$ (wherein $R^8$ and $R^9$ are, independently, hydrogen or $C_{1-6}$ alkyl), $C_{1-4}$ alkyl (itself optionally substituted by $S(O)_2(C_{1-4}$ alkyl), $S(O)_2$phenyl), $C_{1-4}$ alkoxy, $S(O)_kR^{26}$ (wherein k is 0, 1 or 2 (preferably 2); and $R^{26}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), $C_{1-4}$ haloalkylthio, $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$ (and these alkyl groups may join to form a ring as described for $R^6$ and $R^7$ above).

In another aspect the variable $R^4$ is phenyl optionally substituted by: halo, hydroxy, nitro, cyano, amino, $C_{1-4}$ alkyl (itself optionally substituted by $S(O)_2$phenyl), $C_{1-4}$ alkoxy, $S(O)^kR^{26}$ (wherein k is 0, 1 or 2; and $R^{26}$ is $C_{1-4}$ alkyl or phenyl) or $C_{1-4}$ haloalkylthio.

In a further aspect the variable $R^4$ is phenyl optionally substituted by: halo, hydroxy, nitro, cyano, $NR^8R^9$ (wherein $R^8$ and $R^9$ are, independently, hydrogen or $C_{1-4}$ alkyl), $C_{1-4}$ alkyl (itself optionally substituted by $S(O)_2$phenyl), $C_{1-4}$ alkoxy, $S(O)_kR^{26}$ (wherein k is 0, 1 or 2; and $R^{26}$ is $C_{1-4}$ alkyl or phenyl) or $C_{1-4}$ haloalkylthio.

The amine group $NR^8R^9$ is, for example, mono-($C_{1-4}$) alkylamino (such as $NHCH_3$ or $NHCH_2CH_3$) or di-($C_{1-4}$) alkylamino (such as $N(CH_3)_2$).

In yet another aspect of the invention $R^4$ is phenyl mono-substituted with halogen (for example fluorine or chlorine), $C_{1-4}$ alkyl (for example methyl or ethyl), $C_{1-4}$ alkoxy (for example methoxy or ethoxy) or $NR^8R^9$ (wherein $R^8$ and $R^9$ are, independently, hydrogen or $C_{1-6}$ alkyl; and $NR^8R^9$ is especially $NHCH_3$, $NHCH_2CH_3$ or $N(CH_3)_2$).

In a further aspect $R^4$ is phenyl substituted with halogen, alkyl or alkoxy.

In a still further aspect of the invention $R^4$ is phenyl mono-substituted with halogen (especially chlorine) or $C_{1-4}$ alkyl (especially methyl).

In yet another aspect $R^5$ is hydrogen.

In another aspect the present invention provides a pharmaceutically acceptable salt of a compound of formula (I), for example a metal salt {such as an alkali metal salt (for example the sodium salt)} of a compound of formula (I).

Compounds of formula (Ia), (Ib), (Ic), (Id), (Ie), (If), (Ig) and (Ih) are examples of compounds of formula (I).

In a still further aspect the present invention provides a compound of formula (Ia):

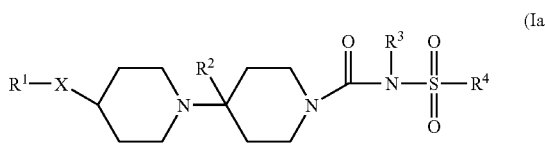

(Ia)

wherein: X, $R^1$, $R^2$, $R^3$ and $R^4$ are as defined above; or a pharmaceutically acceptable salt thereof.

In a still further aspect the present invention provides a compound of formula (Ib):

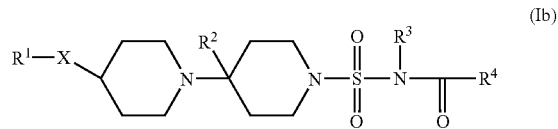

(Ib)

wherein: X, $R^1$, $R^2$, $R^3$ and $R^4$ are as defined above; or a pharmaceutically acceptable salt thereof.

In a still further aspect the present invention provides a compound of formula (Ic):

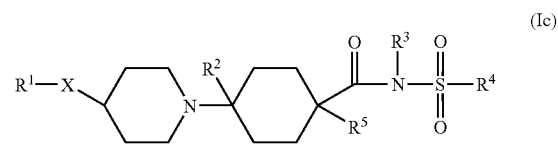

(Ic)

wherein: X, $R^1$, $R^2$, $R^3$, $R^4$ and $R^5$ are as defined above; or a pharmaceutically acceptable salt thereof. In another aspect the compounds of formula (Ic) are preferably trans in terms of relative stereochemistry, that is, the piperidine ring and the $C(O)N(R^3)S(O)_2R^4$ group are both equatorial on the cyclohexane ring.

In a still further aspect the present invention provides a compound of formula (Id):

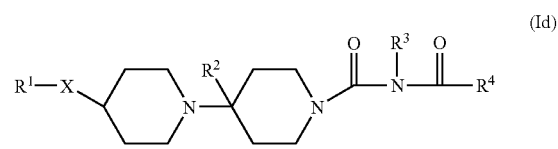

(Id)

wherein: X, $R^1$, $R^2$, $R^3$ and $R^4$ are as defined above; or a pharmaceutically acceptable salt thereof.

In a still further aspect the present invention provides a compound of formula (Ie):

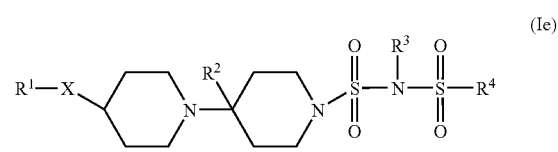

(Ie)

wherein: X, $R^1$, $R^2$, $R^3$ and $R^4$ are as defined above; or a pharmaceutically acceptable salt thereof.

In a still further aspect the present invention provides a compound of formula (If):

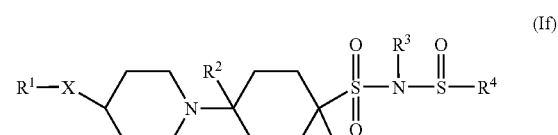

(If)

wherein: X, $R^1$, $R^2$, $R^3$, $R^4$ and $R^5$ are as defined above; or a pharmaceutically acceptable salt thereof. In another aspect the compounds of formula (If) are preferably trans in terms of relative stereochemistry, that is, the piperidine ring and the $S(O)_2N(R^3)C(O)R^4$ group are both equatorial on the cyclohexane ring.

In a still further aspect the present invention provides a compound of formula (Ig):

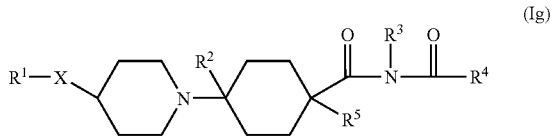

(Ig)

wherein: X, $R^1$, $R^2$, $R^3$, $R^4$ and $R^5$ are as defined above; or a pharmaceutically acceptable salt thereof. In another aspect the compounds of formula (Ig) are preferably trans in terms of relative stereochemistry, that is, the piperidine ring and the $C(O)N(R^3)C(O)R^4$ group are both equatorial on the cyclohexane ring.

In a still further aspect the present invention provides a compound of formula (Ih):

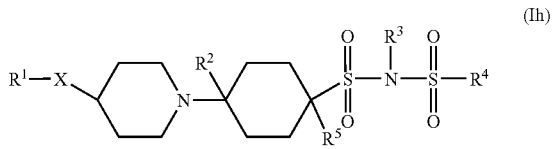

(Ih)

wherein: X, $R^1$, $R^2$, $R^3$, $R^4$ and $R^5$ are as defined above; or a pharmaceutically acceptable salt thereof. In another aspect the compounds of formula (Ih) are preferably trans in terms of relative stereochemistry, that is the piperidine ring and the $S(O)_2N(R^3)S(O)_2R^4$ group are both equatorial on the cyclohexane ring.

A compound of formula (Ia) is, for example:

N-[[4-(2-Chloro-4-fluorophenoxy)[1,4'-bipiperidin]-1'-yl]carbonyl]4-methyl-benzenesulfonamide;
N-[[4-(2-Chloro-4-fluorophenoxy)[1,4'-bipiperidin]-1'-yl]carbonyl]-2-methyl-benzenesulfonamide;
4-Chloro-N-[[4-(2-chloro-4-fluorophenoxy)[1,4'-bipiperidin]-1'-yl]carbonyl]-benzenesulfonamide;
2-Chloro-N-[[4-(2-chloro-4-fluorophenoxy)[1,4'-bipiperidin]-1'-yl]carbonyl]-benzenesulfonamide;
N-[[4-(2-Chloro-4-fluorophenoxy)[1,4'-bipiperidin]-1'-yl]carbonyl]-4-fluoro-benzenesulfonamide;
N-[[4-(2-Chloro-4-fluorophenoxy)[1,4'-bipiperidin]-1'-yl]carbonyl]-benzenesulfonamide;
N-[[4-(4-Chloro-2-methylphenoxy)[1,4'-bipiperidin]-1'-yl]carbonyl]-2-methyl-benzenesulfonamide;
4-Chloro-N-[[4-(4-chloro-2-methylphenoxy)[1,4'-bipiperidin]-1'-yl]carbonyl]-benzenesulfonamide;
2-Chloro-N-[[4-(4-chloro-2-methylphenoxy)[1,4'-bipiperidin]-1'-yl]carbonyl]-benzenesulfonamide;
N-[[4-(4-Chloro-2-methylphenoxy)[1,4'-bipiperidin]-1'-yl]carbonyl]-4-fluoro-benzenesulfonamide;
N-[[4-(4-Chloro-2-methylphenoxy)[1,4'-bipiperidin]-1'-yl]carbonyl]-4-methyl-benzenesulfonamide;
N-[[4-(4-Chloro-2-methylphenoxy)[1,4'-bipiperidin]-1'-yl]carbonyl]-benzenesulfonamide;
N-[[4-(2,4-Dichloro-3-methylphenoxy)[1,4'-bipiperidin]-1'-yl]carbonyl]-2-methyl-benzenesulfonamide;
N-[[4-(2,4-Dichloro-3-methylphenoxy)[1,4'-bipiperidin]-1'-yl]carbonyl]-4-methyl-benzenesulfonamide;
2-Chloro-N-[[4-(2,4-dichloro-3-methylphenoxy)[1,4'-bipiperidin]-1'-yl]carbonyl]-benzenesulfonamide;
4-Chloro-N-[[4-(2,4-dichloro-3-methylphenoxy)[1,4'-bipiperidin]-1'-yl]carbonyl]-benzenesulfonamide;
N-[[4-(2,4-Dichloro-3-methylphenoxy)[1,4'-bipiperidin]-1'-yl]carbonyl]-4-fluoro-benzenesulfonamide;
N-[[4-(2,4-Dichloro-3-methylphenoxy)[1,4'-bipiperidin]-1'-yl]carbonyl]-benzenesulfonamide;
N-[[4-(3,4-Dichloro-2-methylphenoxy)[1,4'-bipiperidin]-1'-yl]carbonyl]-2-methyl-benzenesulfonamide;
N-[[4-(3,4-Dichloro-2-methylphenoxy)[1,4'-bipiperidin]-1'-yl]carbonyl]-4-methyl-benzenesulfonamide;
2-Chloro-N-[[4-(3,4-dichloro-2-methylphenoxy)[1,4'-bipiperidin]-1'-yl]carbonyl]-benzenesulfonamide;
4-Chloro-N-[[4-(3,4-dichloro-2-methylphenoxy)[1,4'-bipiperidin]-1'-yl]carbonyl]-benzenesulfonamide;
N-[[4-(3,4-Dichloro-2-methylphenoxy)[1,4'-bipiperidin]-1'-yl]carbonyl]-4-fluoro-benzenesulfonamide;
N-[[4-(3,4-Dichloro-2-methylphenoxy)[1,4'-bipiperidin]-1'-yl]carbonyl]-benzenesulfonamide;
N-[[4-(3,4-Dichlorophenoxy)-4'-methyl[1,4'-bipiperidin]-1'-yl]carbonyl]-4-methyl-benzenesulfonamide;
N-[[4-(3,4-Dichlorophenoxy)-4'-methyl[1,4'-bipiperidin]-1'-yl]carbonyl]-4-fluoro-benzenesulfonamide;
N-[[4-(3,4-Dichlorophenoxy)-4'-methyl[1,4'-bipiperidin]-1'-yl]carbonyl]-2-methyl-benzenesulfonamide;
4-Chloro-N-[[(4-(3,4-dichlorophenoxy)-4'-methyl[1,4'-bipiperidin]-1'-yl]carbonyl]-benzenesulfonamide;
2-Chloro-N-[[4-(3,4-dichlorophenoxy)-4'-methyl[1,4'-bipiperidin]-1'-yl]carbonyl]-benzenesulfonamide;
N-[[4-(3,4-Dichlorophenoxy)-4'-methyl[1,4'-bipiperidin]-1'-yl]carbonyl]-3-trifluoromethyl-benzenesulfonamide;
3-Cyano-N-[[4-(3,4-dichlorophenoxy)-4'-methyl[1,4'-bipiperidin]-1'-yl]carbonyl]-benzenesulfonamide;
N-[[4-(3,4-Dichlorophenoxy)[1,4'-bipiperidin]-1'-yl]carbonyl]-benzenemethanesulfonamide;
N-[[4-(3,4-Dichlorophenoxy)[1,4'-bipiperidin]-1'-yl]carbonyl]-methanesulfonamide;
N-[[4-(4-Chloro-3-methylphenoxy)[1,4'-bipiperidin]-1'-yl]carbonyl]-2-methyl-benzenesulfonamide;
N-[[4-(4-Chloro-3-methylphenoxy)[1,4'-bipiperidin]-1'-yl]carbonyl]-4-methyl-benzenesulfonamide;
4-Chloro-N-[[4-(4-chloro-3-methylphenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-N,4-dimethyl-benzenesulfonamide;
N-[[4-[(3,4-Dichlorophenyl)methyl][1,4'-bipiperidin]-1'-yl]carbonyl]-4-methyl-benzenesulfonamide;
4-Chloro-N-[[4-[(3,4-dichlorophenyl)methyl][1,4'-bipiperidin]-1'-yl]carbonyl]-benzenesulfonamide;
N-[[4-[(3,4-Dichlorophenyl)amino][1,4'-bipiperidin]-1'-yl]carbonyl]-4-methyl-benzenesulfonamide;
4-Chloro-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]4-methyl-benzenesulfonamide;
N-[[4-(3,4-Dichlorophenoxy)[1,4'-bipiperidin]-1'-yl]carbonyl]-2-methyl-benzenesulfonamide;
3-Bromo-N-[[4-(3,4-dichlorophenoxy)[1,4'-bipiperidin]-1'-yl]carbonyl]-benzenesulfonamide;
4-Bromo-N-[[4-(3,4-dichlorophenoxy)[1,4'-bipiperidin]-1'-yl]carbonyl]-benzenesulfonamide;
3,5-Dichloro-N-[[4-(3,4-dichlorophenoxy)[1,4'-bipiperidin]-1'-yl]carbonyl]-benzenesulfonamide;

3-Cyano-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-2,5-dimethoxy-benzenesulfonamide;
N-[[4-(3,4-Dichlorophenoxy)([1,4'-bipiperidin]-1'-yl]carbonyl)-3,4-dimethoxy-benzenesulfonamide;
N-[[4-(3,4-Dichlorophenoxy)[1,4'-bipiperidin]-1'-yl]carbonyl]-4-(3,3-dimethyl-2-oxo-1-azetidinyl)-benzenesulfonamide;
N-[[4-(3,4-Dichlorophenoxy)[1,4'-bipiperidin]-1'-yl]carbonyl]-4-(4,5-dihydro-3-methyl-5-oxo-1H-pyrazol-1-yl)-benzenesulfonamide;
N-[[4-(3,4-Dichlorophenoxy)[1,4'-bipiperidin]-1'-yl]carbonyl]-3-(4,5-dihydro-3-methyl-5-oxo-1H-pyrazol-1-yl)-benzenesulfonamide;
N-[[4-(3,4-Dichlorophenoxy)[1,4'-bipiperidin]-1'-yl]carbonyl]-4-hydroxy-benzenesulfonamide;
N-[(4-(3,4-Dichlorophenoxy)[1,4'-bipiperidin]-1'-yl]carbonyl]-3-(trifluoromethyl)-benzenesulfonamide;
N-[[4-(3,4-Dichlorophenoxy)[1,4'-bipiperidin]-1'-yl]carbonyl]-benzenesulfonamide;
4-[[[[4-(3,4-Dichlorophenoxy)[1,4'-bipiperidin]-1'-yl]carbonyl]amino]sulfonyl]-benzoic acid, methyl ester;
2-Bromo-N-[[4-(3,4-dichlorophenoxy)[1,4'-bipiperidin]-1'-yl]carbonyl]-benzenesulfonamide;
N-[5-[[[[4-(3,4-Dichlorophenoxy)[1,4'-bipiperidin]-1'-yl]carbonyl]amino]sulfonyl]-1,3,4-thiadiazol-2-yl]-acetamide;
N-[[4-(3,4-Dichlorophenoxy)[1,4'-bipiperidin]-1'-yl]carbonyl]-5-(dimethylamino)-1-naphthalenesulfonamide;
N-[[4-(3,4-Dichlorophenoxy)[1,4'-bipiperidin]-1'-yl]carbonyl]-2-naphthalenesulfonamide;
N-[[4-(3,4-Dichlorophenoxy)[1,4'-bipiperidin]-1'-yl]carbonyl]-2,4-dimethyl-5-thiazolesulfonamide;
N-[[4-(3,4-Dichlorophenoxy)[1,4'-bipiperidin]-1'-yl]carbonyl]-2-(1-piperidinyl)-3-pyridinesulfonamide;
5-Chloro-N-[[4-(3,4-dichlorophenoxy)[1,4'-bipiperidin]-1'-yl]carbonyl]-2-thiophenesulfonamide;
5-Bromo-N-[[4-(3,4-dichlorophenoxy)[1,4'-bipiperidin]-1'-yl]carbonyl]-2-thiophenesulfonamide;
N-[[4-(3,4-Dichlorophenoxy)[1,4'-bipiperidin]-1'-yl]carbonyl]tetrahydro-3-thiophenesulfonamide; 1,1-dioxide
4,5-Dichloro-N-[[4-(3,4-dichlorophenoxy)[1,4'-bipiperidin]-1'-yl]carbonyl]-2-thiophenesulfonamide;
4-Chloro-N-[[4-(3,4-dichlorophenoxy)[1,4'-bipiperidin]-1'-yl]carbonyl]-2,5-dimethyl-benzenesulfonamide;
4-n-Butyl-N-[[4-(3,4-dichlorophenoxy)[1,4'-bipiperidin]-1'-yl]carbonyl]-benzenesulfonamide;
2,5-Dichloro-N-[[4-(3,4-dichlorophenoxy)[1,4'-bipiperidin]-1'-yl]carbonyl]-3-thiophenesulfonamide;
4-n-Butoxy-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-2-(trifluoromethoxy)-benzenesulfonamide;
N-[[4-(3,4-Dichlorophenoxy)[1,4'-bipiperidin]-1'-yl]carbonyl]-1-methyl-1H-imidazole-4-sulfonamide;
5-Amino-N-[[4-(3,4-dichlorophenoxy)[1,4'-bipiperidin]-1'-yl]carbonyl]-1,3,4-thiadiazole-2-sulfonamide;
4-Bromo-N-[[4-(3,4-dichlorophenoxy)[1,4'-bipiperidin]-1'-yl]carbonyl]-2-thiophenesulfonamide;
N-[[4-(3,4-Dichlorophenoxy)[1,4'-bipiperidin]-1'-yl]carbonyl]-2-(4-morpholinyl)-3-pyridinesulfonamide;
6-Bromo-N-[[4-(3,4-dichlorophenoxy)[1,4'-bipiperidin]-1'-yl]carbonyl]-3-pyridinesulfonamide;
N-[[4-(3,4-Dichlorophenoxy)[1,4'-bipiperidin]-1'-yl]carbonyl]-4-(1,1-dimethylethyl)-benzenesulfonamide;
N-[[4-(3,4-Dichlorophenoxy)[1,4'-bipiperidin]-1'-yl]carbonyl]-5-methyl-2-pyridinesulfonamide;
N-[[4-(3,4-Dichlorophenoxy)[1,4'-bipiperidin]-1'-yl]carbonyl]-2,5-difluoro-benzenesulfonamide;
N-[[4-(3,4-Dichlorophenoxy)[1,4'-bipiperidin]-1'-yl]carbonyl]-4-(trifluoromethoxy)-benzenesulfonamide;
N-[[4-(3,4-Dichlorophenoxy)[1,4'-bipiperidin]-1'-yl]carbonyl]-2,4,5-trifluoro-benzenesulfonamide;
5-Chloro-N-[[4-(3,4-dichlorophenoxy)[1,4'-bipiperidin]-1'-yl]carbonyl]-2,4-difluoro-benzenesulfonamide;
4-Chloro-N-[[4-(3,4-dichlorophenoxy)[1,4'-bipiperidin]-1'-yl]carbonyl]-2,5-difluoro-benzenesulfonamide;
3-Chloro-N-[[4-(3,4-dichlorophenoxy)[1,4'-bipiperidin]-1'-yl]carbonyl]-5-fluoro-2-methyl-benzenesulfonamide;
N-[[4-(2,4-dichloro-3-methylphenoxy)[1,4'-bipiperidin]-1'-yl]carbonyl]-4-fluoro-benzenesulfonamide;
2-chloro-N-[[4-(2,4-dichloro-3-methylphenoxy)[1,4'-bipiperidin]-1'-yl]carbonyl]-benzenesulfonamide;
N-[[4-(3,4-dichloro-2-methylphenoxy)[1,4'-bipiperidin]-1'-yl]carbonyl]4-methyl-benzenesulfonamide;
2-chloro-N-[[4-(3,4-dichloro-2-methylphenoxy)[1,4'-bipiperidin]-1'-yl]carbonyl]-benzenesulfonamide;
N-[[4-(4-chlorophenoxy)[1,4'-bipiperidin]-1'-yl]carbonyl]4-methyl-benzenesulfonamide;
N-[[4 (2,4-dichloro-3-methylphenoxy)[1,4'-bipiperidin]-1'-yl]carbonyl]-2-methyl-benzenesulfonamide;
N-[[4-(2,4-dichloro-3-fluorophenoxy)[1,4'-bipiperidin]-1'-yl]carbonyl]+methyl-benzenesulfonamide;
N-[[4-(4-chloro-2-methylphenoxy)[1,4'-bipiperidin]-1'-yl]carbonyl]-2-methyl-benzenesulfonamide,
2-chloro-N-[[4-(4-chloro-2-methylphenoxy)[1,4'-bipiperidin]-1'-yl]carbonyl]-benzenesulfonamide;
4-chloro-N-[[4-(4-chloro-2-methylphenoxy)[1,4'-bipiperidin]-1'-yl]carbonyl]-benzenesulfonamide;
N-[[4-(2,4-dichlorophenoxy)[1,4'-bipiperidin]-1'-yl]carbonyl]-4-methyl-benzenesulfonamide;
N-[[4-(3-chlorophenoxy)[1,4'-bipiperidin]-1'-yl]carbonyl]-4-methyl-benzenesulfonamide;
2-chloro-N-[[4-(3-chlorophenoxy)[1,4'-bipiperidin]-1'-yl]carbonyl]-benzenesulfonamide;
N-[[4-(3-chlorophenoxy)[1,4'-bipiperidin]-1'-yl]carbonyl]-benzenesulfonamide;
2-chloro-N-[[4-(3-chloro-2-methylphenoxy)[1,4'-bipiperidin]-1'-yl]carbonyl]-benzenesulfonamide;
N-[[4-(2-chloro-4-fluorophenoxy)[1,4'-bipiperidin]-1'-yl]carbonyl]-2-methyl-benzenesulfonamide;
2-chloro-N-[[4-(2,4-dichloro-3-fluorophenoxy)[1,4'-bipiperidin]-1'-yl]carbonyl]-benzenesulfonamide;
4-chloro-N-[[4-(2,4-dichloro-3-fluorophenoxy)[1,4'-bipiperidin]-1'-yl]carbonyl]-benzenesulfonamide;
N-[[4-(2,4-dichloro-3-fluorophenoxy)[1,4'-bipiperidin]-1'-yl]carbonyl]-2-methyl-benzenesulfonamide;
2-chloro-N-[[4-(4-chlorophenoxy)[1,4'-bipiperidin]-1'-yl]carbonyl]benzenesulfonamide;
4-chloro-N-[[4-(4-chlorophenoxy)[1,4'-bipiperidin]-1'-yl]carbonyl]-benzenesulfonamide;
N-[[4-(4-chlorophenoxy)[1,4'-bipiperidin]-1'-yl]carbonyl]-2-methyl-benzenesulfonamide;
2-chloro-N-[[4-(2,4-dichlorophenoxy)[1,4'-bipiperidin]-1'-yl]carbonyl]-benzenesulfonamide;
4-chloro-N-([4-(2,5-dichlorophenoxy)[1,4'-bipiperidin]-1'-ylcarbonyl]-benzenesulfonamide;
N-[[4-(2,4-dichlorophenoxy)[1,4'-bipiperidin]-1'-yl]carbonyl]-2-methyl-benzenesulfonamide;
2-chloro-N-[[4-(3,4-difluorophenoxy)[1,4'-bipiperidin]-1'-yl]carbonyl]-benzenesulfonamide;

N-[[4-(3,4-difluorophenoxy)[1,4'-bipiperidin]-1'-yl]carbonyl]-2-methyl-benzenesulfonamide;
N-[[4-(3,4-difluorophenoxy)[1,4'-bipiperidin]-1'-yl]carbonyl]4-methyl-benzenesulfonamide;
N-[[4-(3-chloro-2-methylphenoxy)[1,4'-bipiperidin]-1'-yl]carbonyl]-4-methyl-benzenesulfonamide;
N-[[4-(3-chloro-2-methylphenoxy)[1,4'-bipiperidin]-1'-yl]carbonyl]-benzenesulfonamide;
3-chloro-N-[[4-(3,4-dichlorophenoxy)[1,4'-bipiperidin]-1'-yl]carbonyl]-benzenesulfonamide;
N-[[4-(3,4-dichlorophenoxy)[1,4'-bipiperidin]-1'-yl]carbonyl]-4-methoxy-benzenesulfonamide;
N-[[4-(3,4-dichlorophenoxy)[1,4'-bipiperidin]-1'-yl]carbonyl]-2,4,5-trifluoro-benzenesulfonamide;
N-[[4-(3,4-dichlorophenoxy)[1,4'-bipiperidin]-1'-yl]carbonyl]-2,5-difluoro-benzenesulfonamide;
N-[[4-(3,4-dichlorophenoxy)[1,4'-bipiperidin]-1'-yl]carbonyl]4-(dimethylamino)-benzenesulfonamide;
N-[[4-(3,4-dichlorophenoxy)(1,4'-bipiperidin]-1'-yl]carbonyl]-2-methoxy-benzenesulfonamide;
4-bromo-N-[[4-(3,4-dichlorophenoxy)[1,4'-bipiperidin]-1'-yl]carbonyl]-benzenesulfonamide;
3,5-dichloro-N-[[4-(3,4-dichlorophenoxy)[1,4'-bipiperidin]-1'-yl]carbonyl]-benzenesulfonamide;
Methyl 2-[[[[4-(3,4-dichlorophenoxy)[1,4'-bipiperidin]-1'-yl]carbonyl]amino]sulfonyl]-benzoate;
2-bromo-N-[[4-(3,4-dichlorophenoxy)[1,4'-bipiperidin]-1'-yl]carbonyl]-benzenesulfonamide;
5-chloro-N-[[4-(3,4-dichlorophenoxy)[1,4'-bipiperidin]-1'-yl]carbonyl]-2-thiophenesulfonamide;
4,5-dichloro-N-[[4-(3,4-dichlorophenoxy)[1,4'-bipiperidin]-1'-yl]carbonyl]-2-thiophenesulfonamide;
4-chloro-N-[[4-(3,4-dichlorophenoxy)[1,4'-bipiperidin]-1'-yl]carbonyl]-2,5-dimethyl-benzenesulfonamide;
2,5-dichloro-N-[[4-(3,4-dichlorophenoxy)[1,4'-bipiperidin]-1'-yl]carbonyl]-3-thiophenesulfonamide;
N-[[4-(3,4-dichlorophenoxy)[1,4'-bipiperidin]-1'-yl]carbonyl]-2-(trifluoromethoxy)-benzenesulfonamide;
4-bromo-N-[[4-(3,4-dichlorophenoxy)[1,4'-bipiperidin]-1'-yl]carbonyl]-2-thiophenesulfonamide;
N-[[4-(3,4-dichlorophenoxy)[1,4'-bipiperidin)-1'-yl]carbonyl]-4-(trifluoromethoxy)-benzenesulfonamide;
5-chloro-N-[[4-(3,4-dichlorophenoxy)[1,4'-bipiperidin]-1'-yl]carbonyl]-2,4-difluoro-benzenesulfonamide;
4-chloro-N-[[4-(3,4-dichlorophenoxy)([1,4'-bipiperidin]-1'-yl]carbonyl]-2,5-difluoro-benzenesulfonamide;
3-chloro-N-[[4-(3,4-dichlorophenoxy)[1,4'-bipiperidin]-1'-yl]carbonyl]-5-fluoro-2-methyl-benzenesulfonamide;
N-[[4-(3,4-dichlorophenoxy)(1,4'-bipiperidin]-1'-yl]carbonyl]-2,6-dimethyl-benzenesulfonamide; or,
N-[[4-(3,4-Dichlorophenoxy)[1,4'-bipiperidin]-1'-yl]carbonyl]-2-propanesulfonamide.

A compound of formula (Ib) is, for example:
4-(3,4-Dichlorophenoxy)-N-(4-methylbenzoyl)-[1,4'-bipiperidine]-1'-sulfonamide;
4-(3,4-dichlorophenoxy)-N-(4-fluorobenzoyl)-[1,4'-bipiperidine]-1'-sulfonamide;
N-(4-chlorobenzoyl)-4-(3,4-dichlorophenoxy)-[1,4'-bipiperidine]-1'-sulfonamide;
4-(3,4-dichlorophenoxy)-N-(4-methylbenzoyl)-[1,4'-bipiperidine]-1'-sulfonamide;
4-(3,4-dichlorophenoxy)-N-[4-(dimethylamino)benzoyl]-[1,4'-bipiperidine]-1'-sulfonamide;
4-(3,4-dichlorophenoxy)-N-(4-ethylbenzoyl)-[1,4'-bipiperidine]-1'-sulfonamide;
4-(3,4-dichlorophenoxy)-N-(2-methoxybenzoyl)-[1,4'-bipiperidine]-1'-sulfonamide;
4-(3,4-dichlorophenoxy)-N-(4-methoxybenzoyl)-[1,4'-bipiperidine]-1'-sulfonamide;
N-(2-chlorobenzoyl)-4-(3,4-dichlorophenoxy)-[1,4'-bipiperidine]-1'-sulfonamide;
4-(3,4-dichlorophenoxy)-N-[3-(methylsulfonyl)benzoyl]-[1,4'-bipiperidine]-1'-sulfonamide;
N-(3-cyanobenzoyl)-4-(3,4-dichlorophenoxy)-[1,4'-bipiperidine]-1'-sulfonamide;
4-(4-chloro-2-methylphenoxy)-N-(4-fluorobenzoyl)-[1,4'-bipiperidine]-1'-sulfonamide;
N-(4-chlorobenzoyl)-4-(4-chloro-2-methylphenoxy)-[1,4'-bipiperidine]-1'-sulfonamide;
4-(4-chloro-2-methylphenoxy)-N-(4-methylbenzoyl)-[1,4'-bipiperidine]-1'-sulfonamide;
4-(4-chloro-2-methylphenoxy)-N-[4-(dimethylamino)benzoyl]-[1,4'-bipiperidine]-1'-sulfonamide;
4-(4-chloro-2-methylphenoxy)-N-(4-ethylbenzoyl)-[1,4'-bipiperidine]-1'-sulfonamide;
4-(4-chloro-2-methylphenoxy)-N-(2-methoxybenzoyl)-[1,4'-bipiperidine]-1'-sulfonamide;
4-(4-chloro-2-methylphenoxy)-N-(4-methoxybenzoyl)-[1,4'-bipiperidine]-1'-sulfonamide;
N-(2-chlorobenzoyl)-4-(4-chloro-2-methylphenoxy)-[1,4'-bipiperidine]-1'-sulfonamide;
4-(4-chloro-2-methylphenoxy)-N-[3-(methylsulfonyl)benzoyl]-[1,4'-bipiperidine]-1'-sulfonamide;
4-(4-chloro-2-methylphenoxy)-N-(3-cyanobenzoyl)-[1,4'-bipiperidine]-1'-sulfonamide;
4-(2,4-dichloro-3-methylphenoxy)-N-(4-fluorobenzoyl)-[1,4'-bipiperidine]-1'-sulfonamide;
N-(4-chlorobenzoyl)-4-(2,4-dichloro-3-methylphenoxy)-[1,4'-bipiperidine]-1'-sulfonamide;
4-(2,4-dichloro-3-methylphenoxy)-N-(4-methylbenzoyl)-[1,4'-bipiperidine]-1'-sulfonamide;
4-(2,4-dichloro-3-methylphenoxy)-N-[4-(dimethylamino)benzoyl]-[1,4'-bipiperidine]-1'-sulfonamide;
4-(2,4-dichloro-3-methylphenoxy)-N-(4-ethylbenzoyl)-[1,4'-bipiperidine]-1'-sulfonamide;
4-(2,4-dichloro-3-methylphenoxy)-N-(2-methoxybenzoyl)-[1,4'-bipiperidine]-1'-sulfonamide;
4-(2,4-dichloro-3-methylphenoxy)-N-(4-methoxybenzoyl)-[1,4'-bipiperidine]-1'-sulfonamide;
N-(2-chlorobenzoyl)-4-(2,4-dichloro-3-methylphenoxy)-[1,4'-bipiperidine]-1'-sulfonamide;
4-(2,4-dichloro-3-methylphenoxy)-N-[3-(methylsulfonyl)benzoyl]-[1,4'-bipiperidine]-1'-sulfonamide;
N-(3-cyanobenzoyl)-4-(3,4-dichlorophenoxy)-[1,4'-bipiperidine]-1'-sulfonamide;
4-(3,4-dichloro-2-methylphenoxy)-N-(4-fluorobenzoyl)-[1,4'-bipiperidine]-1'-sulfonamide;
N-(4-chlorobenzoyl)-4-(3,4-dichloro-2-methylphenoxy)-[1,4'-bipiperidine]-1'-sulfonamide;
4-(3,4-dichloro-2-methylphenoxy)-N-(4-methylbenzoyl)-[1,4'-bipiperidine]-1'-sulfonamide;
4-(3,4-dichloro-2-methylphenoxy)-N-[4-(dimethylamino)benzoyl]-[1,4'-bipiperidine]-1'-sulfonamide;
4-(3,4-dichloro-2-methylphenoxy)-N-(4-ethylbenzoyl)-[1,4'-bipiperidine]-1'-sulfonamide;
4-(3,4-dichloro-2-methylphenoxy)-N-(2-methoxybenzoyl)-[1,4'-bipiperidine]-1'-sulfonamide;
4-(3,4-dichloro-2-methylphenoxy)-N-(4-methoxybenzoyl)-[1,4'-bipiperidine]-1'-sulfonamide;
N-(2-chlorobenzoyl)-4-(3,4-dichloro-2-methylphenoxy)-[1,4'-bipiperidine]-1'-sulfonamide;
4-(3,4-dichloro-2-methylphenoxy)-N-[3-(methylsulfonyl)benzoyl]-[1,4'-bipiperidine]-1'-sulfonamide;

N-(3-cyanobenzoyl)-4-(3,4-dichloro-2-methylphenoxy)-[1,4'-bipiperidine]-1'-sulfonamide;
N-benzoyl-4-(3,4-dichloro-2-methylphenoxy)-[1,4'-bipiperidine]-1'-sulfonamide;
N-benzoyl-4-(2,4-dichlorophenoxy)-[1,4'-bipiperidine]-1'-sulfonamide;
N-(3-cyanobenzoyl)-4-(3,4-dichlorophenoxy)-[1,4'-bipiperidine]-1'-sulfonamide;
4-(3,4-dichlorophenoxy)-N-(4-fluorobenzoyl)-[1,4'-bipiperidine]-1'-sulfonamide;
4-(3,4-dichlorophenoxy)-N-[3-(methylsulfonyl)benzoyl]-[1,4'-bipiperidine]-1'-sulfonamide;
4-(4-chloro-2-methylphenoxy)-N-[3-(methylsulfonyl)benzoyl]-[1,4'-bipiperidine]-1'-sulfonamide;
N-(2-chlorobenzoyl)-4-(3,4-dichlorophenoxy)-[1,4'-bipiperidine]-1'-sulfonamide;
N-(4-chlorobenzoyl)-4-(3,4-dichlorophenoxy)-[1,4'-bipiperidine]-1'-sulfonamide;
N-(4-chlorobenzoyl)-4-(4-chloro-2-methylphenoxy)-[1,4'-bipiperidine]-1'-sulfonamide;
4-(3,4-dichlorophenoxy)-N-(2-methoxybenzoyl)-[1,4'-bipiperidine]-1'-sulfonamide;
4-(3,4-dichlorophenoxy)-N-(4-methoxybenzoyl)-[1,4'-bipiperidine]-1'-sulfonamide;
4-(3,4-dichlorophenoxy)-N-(4-methylbenzoyl)-[1,4'-bipiperidine]-1'-sulfonamide;
4-(3,4-dichlorophenoxy)-N-[(1,2-dihydro-1-oxo-4-isoquinolinyl)carbonyl]-[1,4'-bipiperidine]-1'-sulfonamide;
N-(cyclohexylcarbonyl)-4-(3,4-dichlorophenoxy)-[1,4'-bipiperidine]-1'-sulfonamide;
4-(3,4-dichlorophenoxy)-N-(2-methyl-1-oxopropyl)-[1,4'-bipiperidine)-1'-sulfonamide;
4-(3,4-dichlorophenoxy)-N-(2-phenylacetyl)-[1,4'-bipiperidine]-1'-sulfonamide; or,
N-[[4-(3,4-dichlorophenoxy)[1,4'-bipiperidin]-1'-yl]carbonyl]-2-propanesulfonamide.

A compound of formula (Ic) is, for example:
Trans N-[[4-[4-(3,4-Dichlorophenoxy)-1-piperidinyl]cyclohexyl]carbonyl]-4-methyl-benzenesulfonamide;
Trans N-[[4-[4-(3,4-Dichlorophenoxy)-1-piperidinyl]cyclohexyl]carbonyl]-N,4-dimethyl-benzenesulfonamide;
Trans 4-chloro-N-[[4-[4-(3,4-dichlorophenoxy)-1-piperidinyl]cyclohexyl]carbonyl]-benzenesulfonamide;
Trans N-[[4-[4-(3,4-dichlorophenoxy)-1-piperidinyl]cyclohexyl]carbonyl]-4-methyl-benzenesulfonamide;
Trans N-[[4-[4-(3,4-dichlorophenoxy)-1-piperidinyl]cyclohexyl]carbonyl]-2-methyl-benzenesulfonamide;
Trans 3-bromo-N-[[4-[4-(3,4-dichlorophenoxy)-1-piperidinyl]cyclohexyl]carbonyl]-benzenesulfonamide;
Trans 4-bromo-N-[[4-[4-(3,4-dichlorophenoxy)-1-piperidinyl]cyclohexyl]carbonyl]-benzenesulfonamide;
Trans 3,5-dichloro-N-[[4-[4-(3,4-dichlorophenoxy)-1-piperidinyl]cyclohexyl]carbonyl]-benzenesulfonamide;
Trans 3-cyano-N-[[4-[4-(3,4-dichlorophenoxy)-1-piperidinyl]cyclohexyl]carbonyl]-benzenesulfonamide;
Trans N-[[4-[4-(3,4-dichlorophenoxy)-1-piperidinyl]cyclohexyl]carbonyl]-2,5-dimethoxy-benzenesulfonamide;
Trans N-[[4-[4-(3,4-dichlorophenoxy)-1-piperidinyl]cyclohexyl]carbonyl]-3,4-dimethoxy-benzenesulfonamide;
Trans N-[[4-[4-(3,4-dichlorophenoxy)-1-piperidinyl]cyclohexyl]carbonyl]-4-(3,3-dimethyl-2-oxo-1-azetidinyl)-benzenesulfonamide;
Trans N-[[4-[4-(3,4-dichlorophenoxy)-1-piperidinyl]cyclohexyl]carbonyl]-4-(4,5-dihydro-3-methyl-5-oxo-1H-pyrazol-1-yl)-benzenesulfonamide;
Trans N-[[4-[4-(3,4-dichlorophenoxy)-1-piperidinyl]cyclohexyl]carbonyl]-3-(4,5-dihydro-3-methyl-5-oxo-1H-pyrazol-1-yl)-benzenesulfonamide;
Trans N-[[4-[4-(3,4-dichlorophenoxy)-1-piperidinyl]cyclohexyl]carbonyl]-4-hydroxy-benzenesulfonamide;
Trans N-[(4-[4-(3,4-dichlorophenoxy)-1-piperidinyl]cyclohexyl]carbonyl]-3-(trifluoromethyl)-benzenesulfonamide;
Trans N-[[4-[4-(3,4-dichlorophenoxy)-1-piperidinyl]cyclohexyl]carbonyl]-benzenesulfonamide;
Trans 2-[[[[4-[4-(3,4-dichlorophenoxy)-1-piperidinyl]cyclohexyl]carbonyl]amino]-sulfonyl]-benzoic acid, methyl ester;
Trans 2-bromo-N-[[4-[4-(3,4-dichlorophenoxy)-1-piperidinyl]cyclohexyl]carbonyl]-benzenesulfonamide;
Trans N-[5-[[[[4-[4-(3,4-dichlorophenoxy)-1-piperidinyl]cyclohexyl]carbonyl]amino]sulfonyl]-1,3,4-thiadiazol-2-yl]-acetamide;
Trans N-[[4-[4-(3,4-dichlorophenoxy)-1-piperidinyl]cyclohexyl]carbonyl]-5-(dimethylamino)-1-naphthalenesulfonamide;
Trans N-[[4-[4-(3,4-dichlorophenoxy)-1-piperidinyl]cyclohexyl]carbonyl]-2-naphthalenesulfonamide;
Trans N-[[4-[4-(3,4-dichlorophenoxy)-1-piperidinyl]cyclohexyl]carbonyl]-2,4-dimethyl-5-thiazolesulfonamide;
Trans N-[[4-[4-(3,4-dichlorophenoxy)-1-piperidinyl]cyclohexyl]carbonyl]-2-(1-piperidinyl)-3-pyridinesulfonamide;
Trans 5-chloro-N-[[4-[4-(3,4-dichlorophenoxy)-1-piperidinyl]cyclohexyl]carbonyl]-2-thiophenesulfonamide;
Trans 5-bromo-N-[[4-[4-(3,4-dichlorophenoxy)-1-piperidinyl]cyclohexyl]carbonyl]-2-thiophenesulfonamide;
Trans N-[[4-[4-(3,4-dichlorophenoxy)-1-piperidinyl]cyclohexyl]carbonyl]tetrahydro-3-thiophenesulfonamide, 1,1-dioxide;
Trans 4,5-dichloro-N-[[4-[4-(3,4-dichlorophenoxy)-1-piperidinyl]cyclohexyl-1-carbonyl)-2-thiophenesulfonamide;
Trans 4-chloro-N-[[4-[4-(3,4-dichlorophenoxy)-1-piperidinyl]cyclohexyl]carbonyl]-2,5-dimethyl-benzenesulfonamide;
Trans 4-n-butyl-N-([4-[4-(3,4-dichlorophenoxy)-1-piperidinyl]cyclohexyl]carbonyl]-benzenesulfonamide;
Trans 2,5-dichloro-N-[(4-[4-(3,4-dichlorophenoxy)-1-piperidinyl]cyclohexyl]carbonyl]-3-thiophenesulfonamide;
Trans 4-n-butoxy-N-[[4-[4-(3,4-dichlorophenoxy)-1-piperidinyl]cyclohexyl]carbonyl]-benzenesulfonamide;
Trans N-[[4-[4-(3,4-dichlorophenoxy)-1-piperidinyl]cyclohexyl]carbonyl]-2-(trifluoromethoxy)-benzenesulfonamide;
Trans N-[[4-[4-(3,4-dichlorophenoxy)-1-piperidinyl]cyclohexyl]carbonyl]-1-methyl-1H-imidazole-4-sulfonamide;
Trans 5-amino-N-[[4-[4-(3,4-dichlorophenoxy)-1-piperidinyl]cyclohexyl]carbonyl]-1,3,4-thiadiazole-2-sulfonamide;
Trans 4-bromo-N-[[4-[4-(3,4-dichlorophenoxy)-1-piperidinyl]cyclohexyl]carbonyl]-2-thiophenesulfonamide;
Trans N-[[4-[4-(3,4-dichlorophenoxy)-1-piperidinyl]cyclohexyl]carbonyl]-2-(4-morpholinyl)-3-pyridinesulfonamide;
Trans 6-bromo-N-[[4-[4-(3,4-dichlorophenoxy)-1-piperidinyl]cyclohexyl]carbonyl]-3-pyridinesulfonamide;
Trans N-[[4-[4-(3,4-dichlorophenoxy)-1-piperidinyl]cyclohexyl]carbonyl]-4-(1,1-dimethylethyl)-benzenesulfonamide;
Trans N-[[4-[4-(3,4-dichlorophenoxy)-1-piperidinyl]cyclohexyl]carbonyl]-5-methyl-2-pyridinesulfonamide;

Trans N-[[4-[4-(3,4-dichlorophenoxy)-1-piperidinyl]cyclohexyl]carbonyl]-2,5-difluoro-benzenesulfonamide;
Trans N-[[4-[4-(3,4-dichlorophenoxy)-1-piperidinyl]cyclohexyl]carbonyl]-4-(trifluoromethoxy)-benzenesulfonamide;
Trans N-[[4-[4-(3,4-dichlorophenoxy)-1-piperidinyl]cyclohexyl]carbonyl]-2,4,5-trifluoro-benzenesulfonamide;
Trans 5-chloro-N-[[4[4-(3,4-dichlorophenoxy)-1-piperidinyl]cyclohexyl]carbonyl]-2,4-difluoro-benzenesulfonamide;
Trans 4-chloro-N-[[4-[4-(3,4-dichlorophenoxy)-1-piperidinyl]cyclohexyl]carbonyl]-2,5-difluoro-benzenesulfonamide;
Trans 3-chloro-N-[[4-[4-(3,4-dichlorophenoxy)-1-piperidinyl]cyclohexyl]carbonyl]-5-fluoro-2-methyl-benzenesulfonamide;
Trans N-[[4-[4-(3,4-dichlorophenoxy)-1-piperidinyl]cyclohexyl]carbonyl]-2-methyl-benzenesulfonamide;
Trans N-[[4-[4-(3,4-dichlorophenoxy)-1-piperidinyl]cyclohexyl]carbonyl]-2-methoxy-benzenesulfonamide;
Trans N-[[4-[4-(3,4-dichlorophenoxy)-1-piperidinyl]cyclohexyl]carbonyl]-2,6-dimethyl-benzenesulfonamide;
Trans N-[[4-[4-(3,4-dichlorophenoxy)-1-piperidinyl]cyclohexyl]carbonyl]-4-methyl-benzenesulfonamide;
Trans N-[[4-[4-(3,4-dichlorophenoxy)-1-piperidinyl]cyclohexyl]carbonyl]-benzenesulfonamide; or,
Trans N-[[4-[4-(3,4-dichlorophenoxy)-1-piperidinyl]cyclohexyl]carbonyl]-4-(dimethylamino)-benzenesulfonamide.

A compound of formula (Id) is, for example:
4-(3,4-Dichlorophenoxy)-N-(2-methylbenzoyl)-[1,4'-bipiperidine]-1'-carboxamide;
4-(3,4-Dichlorophenoxy)-N-(4-methylbenzoyl)-[1,4'-bipiperidine]-1'-carboxamide;
4-(3,4-Dichlorophenoxy)-N-(4-chlorobenzoyl)-[1,4'-bipiperidine]-1'-carboxamide;
4-(3,4-Dichlorophenoxy)-N-benzoyl-[1,4'-bipiperidine]-1'-carboxamide;
4-(3,4-Dichlorophenoxy)-N-[(4-methylphenyl)sulfonyl]-[1,4'-bipiperidine]-1'-sulfonamide; or,
4-(3,4-dichlorophenoxy)-N-[[4-(1,1-dimethylethyl)phenyl)sulfonyl]-[1,4'-bipiperidine]-1'-sulfonamide.

A compound of formula (Ie) is, for example:
[4-(3,4-dichlorophenoxy)-N-(phenylsulfonyl)-1,4'-bipiperidine]-1'-sulfonamide.

A compound of formula (If) is, for example:
Trans N-benzoyl-4-[4-(3,4-dichlorophenoxy)-1-piperidinyl]-cyclohexanesulfonamide.

A compound of formula (Ig) is, for example:
Trans N-[[4-[4-(3,4-Dichlorophenoxy)-1-piperidinyl]cyclohexyl]carbonyl]-benzamide.

A compound of formula (Ih) is, for example:
Trans N-[[4-[4-(3,4-Dichlorophenoxy)-1-piperidinyl]cyclohexyl]sulfonyl]-benzenesulfonamide.

Compounds of formula (I) (for example compounds of formula (Ia), (Ib), (Ic), (Id), (Ie), (If), (Ig) or (Ih)) can be prepared by the methods described below.

A compound of formula (Ic), (If), (Ig) or (Ih) where $R^3$ and $R^5$ are both hydrogen may be converted to a compound of formula (Ic), (If), (Ig) or (Ih) where $R^5$ is alkyl and $R^3$ is hydrogen by deprotonation to a dianion, for example with 2 equivalents of LDA, followed by reaction with an alkylating agent, $R^5Hal$ (wherein Hal is, for example chlorine).

A compound of formula (Ic), (If), (Ig) or (Ih) where $R^5$ is hydrogen and $R^3$ is not hydrogen may be converted to a compound of formula (Ic), (If), (Ig) or (Ih) where $R^5$ is alkyl and $R^3$ is not hydrogen by deprotonation, for example with 1 equivalent of LDA, followed by reaction with an alkylating agent, $R^5Hal$.

A compound of formula (I), wherein $R^3$ is not hydrogen, can be prepared by alkylating a compound of formula (I), wherein $R^3$ is hydrogen, with a suitable alkylating agent (for example $R^3$-L, wherein L is a leaving group such as triflate, a halide or a diazo group) in the presence of a suitable base (such as sodium hydride) in a suitable solvent.

A compound of formula (I), wherein $R^3$ is hydrogen, T is C(O) and Y is N, can be prepared by reacting a compound of formula (II):

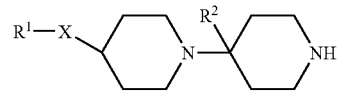

with an isocyanate of formula $R^4N=C=O$ in the presence of a suitable solvent at a suitable temperature (such as room temperature). Isocyanates of formula $R^4WN=C=O$ are commercially available or can be prepared by optional adaptation of methods described in the literature.

A compound of formula (I), wherein T is C(O), W is $S(O)_2$ and Y is N, can be prepared by reacting a compound of formula (II) with a compound of formula (XXII). A compound of formula (XXII):

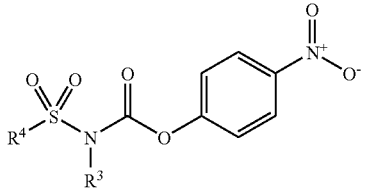

may be prepared from a sulfonamide $R^4SO_2NHR^3$ and p-nitrophenyl chloroformate in the presence of a base, for example triethylamine and a catalyst, for example DMAP, typically at room temperature.

A compound of formula (II) can be prepared by deprotecting a compound of formula (III):

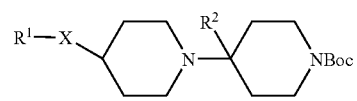

for example using trifluoroacetic acid in a suitable solvent (such as dichloromethane) or using a source of hydrogen chloride in a suitable solvent (such as dioxane).

A compound of formula (III), wherein $R^2$ is hydrogen, can be prepared by reacting a compound of formula (IV):

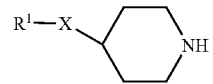

with a compound of formula (V):

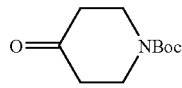
(V)

in the presence of NaBH(OAc)₃ and acetic acid.

A compound of formula (E), wherein $R^2$ is $C_{1-6}$ alkyl, can be prepared by reacting a compound of formula (XVII):

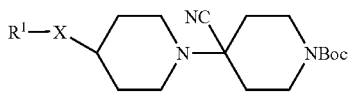
(XVII)

with a Grignard reagent of formula $R^2MgHal$ (wherein Hal is chlorine, bromine or iodine) in a suitable solvent, such as tetrahydrofuran.

A compound of formula (XVII) can be prepared by reacting a compound of formula (IV) with a compound of formula (V) in the presence of titanium tetrisopropoxide, for example in dichloroethane, followed by the addition of diethylaluminium cyanide to a solution, for example in toluene.

A compound of formula (I), wherein $R^3$ is hydrogen, T is $S(O)_2$, W is C(O) and Y is N, can be prepared by reacting a compound of formula (IX):

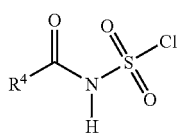
(IX)

with a compound of formula (II) in the presence of a suitable base (such as triethylamine) in a suitable solvent (such as tetrahydrofuran) at a suitable temperature (such as below −60° C.). A compound of formula (IX) can be prepared by reacting an acid $R^4CO_2H$ with $ClS(O)_2N=C=O$, for example below 80° C.

Alternatively, a compound of formula (I), wherein $R^3$ is hydrogen, T is $S(O)_2$, W is C(O) and Y is N, can be prepared by reacting a compound of formula (XVIII):

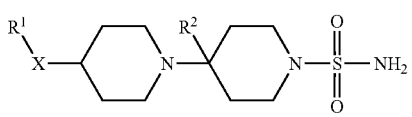
(XVIII)

with an acyl halide $R^4COHal$ in the presence of a base, for example triethylamine in a suitable solvent, for example dichloromethane, for example at room temperature.

A compound of formula (XVIII) may be prepared by the reaction of a compound of formula (II) with sulfamide, for example in dioxan at reflux.

A further method of preparing a compound of formula (I), wherein $R^3$ is hydrogen, T is $S(O)_2$, W is C(O) and Y is N, is to react a compound of formula (XIX):

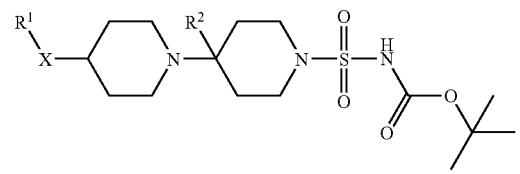
(XIX)

with an acyl halide $R^4COHal$ in the presence of a base, for example triethylamine in a suitable solvent, for example dichloromethane, for example at room temperature, followed by deprotection of the carbamate so formed, for example with trifluoroacetic acid in dichloromethane.

A compound of formula (XIX) can be prepared from a compound of formula (II) and a compound of formula (XX):

$$\text{(XX)}$$

in a suitable solvent for example dichloromethane typically at room temperature.

A compound of formula (I) wherein T and W are both $S(O)_2$ and Y is N, can be prepared by reacting a compound of formula (X):

$$\text{(X)}$$

with a sulfonamide $R^4S(O)_2NHR^3$ in the presence of a base (such as calcium oxide), in a suitable solvent (such as DMSO) at a temperature preferably in the range 50-110° C. (For example see DE 1618439; DE 1249259; Chemical Abstracts 1967, 67, 116716a). A compound of formula (X) can be prepared by reacting a compound of formula (II) with $S(O)_2Cl_2$ in the presence of a suitable base (such as triethylamine).

Alternatively, a compound of formula (I) wherein T and W are both $S(O)_2$ and Y is N, can be prepared by reacting a compound of formula (XVIII) with a sulfonyl chloride $R^4SO_2Cl$ in the presence of a base, for example triethylamine, preferably with dimethylaminopyridine as catalyst in a suitable solvent, for example dichloromethane, for example at room temperature.

A compound of formula (I) wherein T is C(O), W is $S(O)_2$ and Y is $CR^5$, can be prepared by firstly hydrolysing a compound of formula (XI):

$$\text{(XI)}$$

wherein the ester is preferably a $C_{1-6}$ alkyl group, and reacting the product so formed with $R^4S(O)_2NHR^3$ in the presence of an appropriate coupling agent (such as ethyl dimethylaminopropyl carbodiimide (EDCI), with 4-dimethylaminopyridine (DMAP) or 1-hydroxybenzotriazole (HOBT)) in a suitable solvent, for example DMF.

A compound of formula (XI), wherein $R^2$ is hydrogen, can be prepared by reductively aminating a compound of formula (XI):

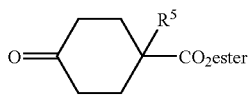

(XII)

with a compound of formula (XIII):

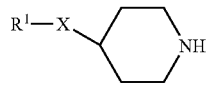

(XIII)

A compound of formula (X) where $R^2$ is alkyl can be prepared by amino nitrile formation between compounds of formula (XII) and (XIII) followed by displacement of the nitrile with a grignard reagent.

A compound of formula (I), wherein T and W are both C(O) and Y is CH or N, can be prepared by heating a compound of formula (XIV):

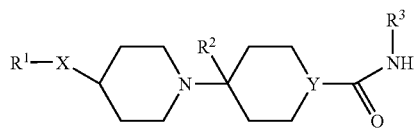

(XIV)

in the presence of $R^4C(OR')_2N(CH_3)_2$ or $R^4C(OR')_3$, wherein R' is methyl or ethyl, or $(OR')_3$ is $(OCH_2)_3CCH_3$. A compound of formula (XI) where Y is $CR^5$ can be prepared by firstly hydrolysing a compound of formula (XI) and then coupling the product so formed with an amine $R^3NH_2$ in the presence of an appropriate coupling agent (such as ethyl dimethylaminopropyl carbodiimide, with 4-dimethylaminopyridine or 1-hydroxybenzotriazole) in a suitable solvent, for example DMF. A compound of formula (XIV) where Y is N and $R^3$ is H may be prepared by reaction of a compound of formula (II) with sodium cyanate in the presence of an acid, for example acetic acid. A compound of formula (XIV) where Y is N and $R^3$ is alkyl may be prepared by reaction of a compound of formula (II) with a compound of formula (XXI): $R^3$—N=C=O; in an inert solvent, for example dichloromethane, for example at room temperature.

A compound of formula (I), wherein T is $S(O)_2$, W is C(O) and Y is $CR^5$, can be prepared by coupling a compound of formula (XV):

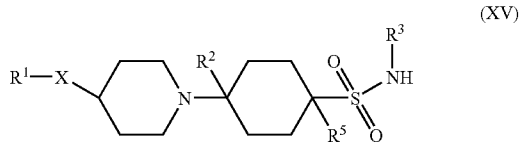

(XV)

to an acid $R^4CO_2H$ in the presence of an appropriate coupling agent (such as ethyl dimethylaminopropyl carbodiimide, 4-dimethylaminopyridine or HOBT) in a suitable solvent.

A compound of formula (I), wherein T and W are both $S(O)_2$ and Y is CH, can be prepared by coupling a compound of formula (XV) to a sulfonyl chloride $R^4S(O)_2CH$, in the presence of a base and a solvent (such as dichloromethane, N,N-dimethylformamide or tetrahydrofuran).

A compound of formula (XV) can be prepared by reductively aminating a compound of formula (XVI):

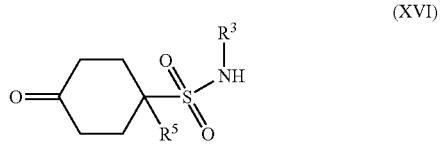

(XVI)

with a compound of formula (IV) to obtain a compound wherein $R^2$ is hydrogen, or aminonitrile formation followed by a Grignard reaction to obtain a compound wherein $R^2$ is alkyl.

A compound of formula (XVI) can be prepared by reacting

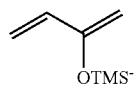

with $CH_2=CR^5—S(O)_2NHR^3$ at an elevated temperature (such as in refluxing toluene) and then hydrolysing the silyl enol ether (such as with acetic acid).

A compound of formula (I) where Y is $CR^5$ and $R^5$ is not hydrogen may be prepared from a compound of formula (I) where Y is CH by reaction of the dianion ($R^3$ is H) or monoanion ($R^3$ is alkyl) (formed with a suitable base, for example LDA) with an alkylating agent (for example $R^5$-L, wherein L is a leaving group such as triflate or a halide) in a suitable solvent for example THF for example at 0° or below.

Further compounds of formula (I) can be prepared by adaptation of: the routes described above, methods described in the art or the Examples recited below. The intermediates identified above are commercially available or can be prepared by using or adapting methods described in the art.

In another aspect the present invention provides processes for the preparation of compounds of formula (I) (for example a compound of formula (Ia), (Ib), (Ic), (Id), (Ie), (If), (Ig) or (Ih)).

The intermediates of formula (X), (XI), (XIV), (XV), (XVI) and (XIX) defined herein are novel and these, and processes for their preparation, are provided as further features of the invention.

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

In one aspect examples of these conditions are:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related, diseases; nasal polyposis; fibroid lung, idiopathic interstitial pneumonia, antittissive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behçet's disease, Sjogren's syndrome or systemic sclerosis;
(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

The compounds of the invention are also H1 antagonists and may be used in the treatment of allergic disorders.

The compounds of the invention may also be used to control a sign and/or symptom of what is commonly referred to as a cold (for example a sign and/or symptom of a common cold or influenza or other associated respiratory virus infection).

According to a further feature of the invention there is provided a compound of formula (I) (for example a compound of formula (Ia), (Ib), (Ic), (Id), (Ie), (If), (Ig) or (Ih)), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity), or antagonising H1, in a warm blooded animal, such as man, in need of such treatment, which comprises administering to said animal an effective amount of a compound of the formula (I) (for example a compound of formula (Ia), (Ib), (Ic), (Id), (Ie), (If), (Ig) or (Ih)), or a pharmaceutically acceptable salt thereof or a solvate thereof.

The invention also provides a compound of the formula (I) (for example a compound of formula (Ia), (Ib), (Ic), (Id), (Ie), (If), (Ig) or (Ih)), or a pharmaceutically acceptable salt thereof or a solvate thereof, for use as a medicament.

In another aspect the invention provides the use of a compound of formula (I) (for example a compound of formula (Ia), (Ib), (Ic), (Id), (Ie), (If), (Ig) or (Ih)), or a pharmaceutically acceptable salt thereof or a solvate thereof, in the manufacture of a medicament for use in therapy (for example modulating chemokine receptor activity (especially CCR3 receptor activity), or antagonising H1, in a warm blooded animal, such as man).

The invention further provides the use of a compound of formula (I) (for example a compound of formula (Ia), (Ib), (Ic), (Id), (Ie), (If), (Ig) or (Ih)), or a pharmaceutically acceptable salt thereof, in the manufacture of a medicament for use in the treatment of:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behçet's disease, Sjogren's syndrome or systemic sclerosis;
(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a warm blooded animal, such as man.

In a further aspect a compound of formula (I) (for example a compound of formula (Ia), (Ib), (Ic), (Id), (Ie), (If), (Ig) or (Ih)), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I) (for example a compound of formula (Ia), (Ib), (Ic), (Id), (Ie), (If), (Ig) or (Ih)), or a pharmaceutically acceptable salt thereof, is useful in the treatment of asthma.

The present invention also provides the use of a compound of formula (I) (for example a compound of formula (Ia), (Ib), (Ic), (Id), (Ie), (If), (Ig) or (Ih)), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I) (for example a compound of formula (Ia), (Ib), (Ic), (Id), (Ie), (If), (Ig) or (Ih)), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition which comprises a compound of the formula (I) (for example a compound of formula (Ia), (Ib), (Ic), (Id), (Ie), (If), (Ig) or (Ih)), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 $mgkg^{-1}$ to 100 $mgkg^{-1}$ of the compound, preferably in the range of 0.1 $mgkg^{-1}$ to 20 $mgkg^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I) (for example a compound of formula (Ia), (Ib), (Ic), (Id), (Ie), (If), (Ig) or (Ih)), or a pharmaceutically-acceptable salt thereof (hereafter Compound X), for therapeutic or prophylactic use in humans:

|  | mg/tablet |
|---|---|
| (a) Tablet I | |
| Compound X | 100 |
| Lactose Ph. Eur. | 179 |
| Croscarmellose sodium | 12.0 |
| Polyvinylpyrrolidone | 6 |
| Magnesium stearate | 3.0 |
| (b) Tablet II | |
| Compound X | 50 |
| Lactose Ph. Eur. | 229 |
| Croscarmellose sodium | 12.0 |
| Polyvinylpyrrolidone | 6 |
| Magnesium stearate | 3.0 |
| (c) Tablet III | |
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

-continued

|  | mg/capsule |
|---|---|
| (d) Capsule | |
| Compound X | 10 |
| Lactose Ph. Eur. | 389 |
| Croscarmellose sodium | 100 |
| Magnesium stearate | 1.0 |

|  | (50 mg/ml) |
|---|---|
| (e) Injection I | |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)-(c) may be enteric coated by conventional means, for example to provide a coating of cellulose acetate phthalate.

The invention will now be illustrated by the following non-limiting Examples in which, unless stated otherwise:
(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$), methanol-D4 ($CD_3OD$) or $CDCl_3$ as the solvent unless otherwise stated;
(ii) mass spectra (MS) were run with an electron energy of 70 electron volts in the chemical ionisation (CI) mode using a direct exposure probe; where indicated ionisation was effected by electron impact (EI) or fast atom bombardment (FAB) or electrospray (ESI); where values for m/z are given, generally only ions which indicate the parent mass are reported, and unless otherwise stated the mass ion quoted is the positive mass ion—$(M+H)^+$;
(iii) the title and sub-title compounds of the examples and methods were named using the ACD/Index name program version 4.55 from Advanced Chemistry Development, Inc;
(iv) unless stated otherwise, reverse phase HPLC was conducted using a Symmetry, NovaPak or Xterra reverse phase silica column; and
(v) the following abbreviations are used:

| RPHPLC | reverse phase HPLC |
|---|---|
| DEAD | diethyl-azodicarboxylate |
| NMP | N-methylpyrrolidone |
| CDI | N,N'-carbonyl diimidazole |
| MTBE | tert-butyl methyl ether |
| DMF | N,N-dimethylformamide |
| HOBT | 1-hydroxybenzotriazole |
| Boc or BOC | tert-butoxycarbonyl |
| HPLC | high pressure liquid chromatography |
| EDCI | Ethyl dimethylaminopropyl carbodiimide |
| TMEDA | Tertamethylethylenediamine |
| PYBROP ™ | bromo-tris-pyrrolidino-phosphonium hexafluorophosphate |
| THF | tetrahydrofuran |
| DCM | dichloromethane |
| TFA | trifluoroacetic acid |
| m. pt. | melting point |
| DMSO | dimethylsulfoxide |
| Ac | Acetate |
| aq | aqueous |
| RT | room temperature |
| IPA | iso-propyl alcohol |
| LDA | Lithium diisopropylamide |
| equiv. | equivalents |

EXAMPLE 1A

N-[[4-(3,4-dichlorophenoxy)[1,4'-bipiperidin]-1'-yl]carbonyl]-4-fluoro-benzenesulfonamide (an Example of a Compound of Formula (Ia)).

To a solution of 4-(3,4-dichlorophenoxy)-1,4'-bipiperidine (Method C; 0.197 g) in dichloromethane (5 ml) was added 4-fluorobenzenesulfonyl isocyanate (0.121 g) dropwise and the reaction was stirred under nitrogen for 12 hours. The solvent was removed under reduced pressure and the resulting product was purified by RPHPLC (Waters Xterra® column), (gradient, 75:25 0.2% aq ammonia/acetonitrile to 5:95 over 10 mins) to give the title compound (60 mg; MS $(M+H)^+$ (APCI+) 530/532).

$^1$H NMR (399.98 MHz, $CD_3OD$) δ 1.50-1.61 (m, 2H), 2.01-2.24 (m, 6H), 2.64-2.73 (m, 2H), 3.25-3.43 (m, 5H), 4.42-4.50 (m, 2H), 4.64-4.71 (m, 1H), 6.95-6.98 (m, 1H), 7.12-7.16 (m, 2H), 7.21-7.22 (m, 1H), 7.41-7.44 (m, 1H), 7.90-7.95 (m, 2H).

The Examples 1B-1AV are examples of compounds of formula (Ia) and were prepared using similar methodology to that of Example 1A. Recrystallisation was required after chromatography for several Examples.

EXAMPLE 2A

N-[[4-(3,4-Dichlorophenoxy)[1,4'-bipiperidin]-1'-yl]carbonyl]-benzenemethanesulfonamide (an Example of a Compound of Formula (Ia)).

To a stirred solution of para-nitrophenylchloroformate (0.141 g) in dichloromethane (5 ml) was added dimethylaminopyridine (0.086 g). After 2 minutes benzenemethanesulfonamide (0.120 g) was added followed by triethylamine (0.078 g). After 30 minutes 4-(3,4-dichlorophenoxy)-1,4'-bipiperidine (Method C; 0.230 g) was added and the reaction was left to stir for 2 hours. The solvent was removed under reduced pressure and the resulting product was purified by RPHPLC (Waters Xterra® column), (gradient, 90:10 0.2% aq ammonia/acetonitrile to 5:95 over 6 mins) to give the title compound (202 mg).

$^1$H NMR (399.98 MHz, $CD_3OD$) δ 1.30-1.43 (m, 2H), 1.73-1.84 (m, 4H), 1.98-2.06 (m, 2H), 2.44-2.55 (m, 3H), 2.59-2.66 (m, 2H), 2.82-2.89 (m, 2H), 4.36-4.42 (m, 3H), 4.41 (s, 2H), 6.88-6.91 (m, 1H), 7.09-7.10 (m, 1H), 7.24-7.31 (m, 3H), 7.36-7.39 (m, 3H); plus 1 drop of 30% NaOD in $D_2O$.

ES+526/528

The Examples 2B-2X are examples of compounds of formula (Ia) and were prepared using similar methodology to that of Example 2A.

EXAMPLE 3A

N-[[4-(3,4-Dichlorophenoxy)[1,4'-bipiperidin]-1'-yl]carbonyl]-N,4-dimethyl-benzenesulfonamide (an Example of a Compound of Formula (Ia) where $R^3$ is not Hydrogen).

To a solution of N-[[4-(3,4-dichlorophenoxy)[1,4'-bipiperidin]-1'-yl]carbonyl]-4-methyl-benzenesulfonamide (Example 1B, 0.3 g) in methanol/dichloromethane (1:1, 40 ml)

was added (trimethylsilyl)diazomethane (2M in hexanes) (5 ml) dropwise. The reaction was stirred under nitrogen for 12 hours. The solvent was removed under reduced pressure and the resulting product was purified by RPHPLC (Waters Xterra® column), (gradient, 75:25 0.2% aq ammonia acetonitrile to 5:95 over 6 mins) to give the title compound (83 mg).

$^1$H NMR (399.98 MHz, CD$_3$OD) δ 1.42-1.53 (m, 2H), 1.63-1.71 (m, 2H), 1.82-1.96 (m, 4H), 2.31 (s, 3H), 2.39-2.47 (m, 2H), 2.48-2.57 (m, 1H); 2.72-2.79 (m, 2H), 2.93-3.01 (m, 2H), 3.69 (s, 3H), 4.20-4.26 (m, 2H), 4.27-4.34 (m, 1H), 6.77-6.81 (m, 1H), 7.00 (d, 1H), 7.21-7.29 (m, 3H), 7.65-7.68 (m, 2H)

ES+540/542; m. pt. 151-153° C.

EXAMPLE 4A

N-Benzoyl-4-(3,4-dichlorophenoxy)-[1,4'-bipiperidine]-1'-sulfonamide (an Example of a Compound of Formula (Ib)).

Benzoyl sulfamoyl chloride (DE931225, (1955) Chemical Abstracts 1956, 50, 7861a; 248 mg) was dissolved in THF (5 ml) and cooled to −78° C. Triethylamine (170 μl) was added dropwise over 160s and the solution was stirred for 25 min. 4-(3,4-Dichlorophenoxy)-1,4'-bipiperidine (Method C; 329 mg) in THF (5 ml) was added dropwise over 35 min. Water was added then the mixture was evaporated. The residue was purified by RPHPLC (Waters Xterra® Column, eluant 0.1% aq ammonium acetate:acetonitrile 75-5:25-95) to give the title compound (37 mg; MS [M+H]$^+$ (APCI+) 512/514).

$^1$H NMR (399.98 MHz, DMSO) δ 1.59 (qd, 2H), 1.74-1.84 (m, 2H), 1.96 (d, 2H), 2.06 (d, 2H), 2.76 (t, 2H), 2.86-3.03 (m, 3H), 3.08-3.17 (m, 2H), 3.71 (d, 2H), 4.57-4.64 (m, 1H), 7.02 (dd, 1H), 7.32 (d, 1H), 7.37 (t, 2H), 7.45 (t, 1H), 7.53 (d, 1H), 7.92 (d, 2H).

EXAMPLE 5A

N-Benzoyl-4-(2,4-dichloro-3-methylphenoxy)-[1,4'-bipiperidine)-1'-sulfonamide (an Example of a Compound of Formula (Ib)).

4-(2,4-Dichloro-3-methylphenoxy)-1,4'-bipiperidine (see Method C; 240 mg) was dissolved in dichloromethane (10 ml). Triethylamine (107 μl) was added followed by benzoyl sulfamoyl chloride (154 mg). The solution was stirrred for 12 h and then concentrated. The residue was purified by by RPHPLC (Waters Xterra® column), (gradient, 90:10 0.2% aq ammonia/acetonitrile to 5:95 over 6 mins) to give the title compound. (70 mg, MS [M+H]$^+$ (APCI+) 526/528; m.pt. 223° C.)

$^1$H NMR (399.98 MHz, CD$_3$OD) δ 8.00-8.03 (m, 2H), 7.38-7.43 (m, 1H), 7.31-7.36 (m, 2H), 7.25 (d, 1H), 6.95 (d, 1H), 4.45-4.52 (m, 1H), 3.80-3.87 (m, 2H), 2.84-2.92 (m, 2H), 2.73-2.81 (m, 2H), 2.51-2.58 (m, 2H), 2.44 (s, 3H), 2.38-2.44 (m, 1H), 1.91-2.03 (m, 4H), 1.80-1.89 (m, 2H), 1.59-1.70 (m, 2H); plus 1 drop of 30% NaOD in D$_2$O.

The Examples 5B-5E are examples of compounds of formula (Ia) and were prepared using similar methodology to that of Example 5A.

EXAMPLE 6A trans 4-Chloro-N-[[(4-[(3,4-dichlorophenoxy)-1-piperidinyl]cyclohexyl]-carbonyl]-benzenesulfonamide (an Example of a Compound of Formula (Ic)).

Sodium 4-[4-(3,4-dichlorophenoxy)-1-piperidinyl]-cyclohexanecarboxylate (Method F, 111 mg), EDCI (99 mg), HOBT (97 mg), DMAP (32 mg) and p-chlorobenzenesulfonamide (98 mg) were combined in DMF (3 ml) and stirred overnight. The solvent was evaporated and the residue was purified by RPHPLC (Waters Xterra® Column, eluant 0.1% aqueous ammonium acetate:acetonitrile 75-25: 25-75) to give the title compound (18 mg; MS [M+H]$^+$ (APCI+) 545/547/549).

$^1$H NMR (399.98 MHz, DMSO) δ 1.23 (q, 2H), 1.35 (q, 2H), 1.74-1.97 (m, 7H), 2.02-2.11 (m, 21), 2.88-3.07 (m, 4H), 3.09-3.21 (m, 2H), 4.56-4.67 (m, 1H), 7.02 (dd, 1H), 7.33 (d, 1H), 7.46 (d, 2H), 7.53 (d, 1H), 7.73 (d, 2H).

EXAMPLE 7A

N-Benzoyl-4-(3,4-dichlorophenoxy)-[1,4'-bipiperidine]-1'-carboxamide (an Example of a Compound of Formula (Id)).

4-(3,4-Dichlorophenoxy)-[1,4'-bipiperidine]-1'-carboxamide (Method H, 200 mg) and triethylorthobenzoate (3 ml) were heated at 150° C. for 16 h, then allowed to reach ambient temperature. 2M HCl (2 ml) was added and the resulting solution was stirred for 4 h. The volatiles were evaporated and the residue was purified by chromatography (24:1 dichloromethane: methanol) followed by RPHPLC (Waters Xterra® column), (gradient, 75:25 0.2% aq ammonia/acetonitrile to 5:95 over 6 mins) to give the title compound (m.pt. 65-80° C.; MS [M+H]$^+$ (ES+) 476/478).

$^1$H NMR (399.98 MHz, DMSO) δ 1.42 (2H, d), 1.58 (2H, d), 1.76 (2H, d), 1.92 (2H, d), 2.39 (2H, t), 2.72-2.78 (2H, m), 2.81-2.94 (3H, m), 3.79-4.22 (2H, m), 4.42 (1H, t), 6.98 (1H, dd), 7.25 (1H, d), 7.44-7.52 (3H, m), 7.56-7.68 (1H, m), 7.83-7.92 (2H, m).

EXAMPLE 8A

N-(3,4-Dichlorobenzoyl)-4-(3,4-dichlorophenoxy)-(1,4'-bipiperidine]-1'-sulfonamide (an Example of a Compound of Formula (Ib)).

4-(3,4-Dichlorophenoxy)-[1,4'-bipiperidine]-1'-sulfonamide (Method G, 200 mg), 3,4 dichlorobenzoylchloride (102 mg) and triethylamine (0.07 ml) were stirred together in dichloromethane (10 ml) at ambient temperature for 24 hours. The solvent was evaporated and the resulting product was purified by RPHPLC (Waters Xterra® column), (gradient, 75:25 0.2% aq ammonia/acetonitrile to 5:95 over 6 mins) to give the title compound (22 mg; m.pt. 166-167° C.; MS APCI 580/582/584 (M+H)).

$^1$H NMR (399.98 MHz, DMSO) δ 1.57-1.79 (m, 4H), 1.89-2.17 (m, 5H), 2.60-2.76 (m, 2H), 3.06-3.25 (m, 2H), 3.36-3.60 (m, 2H), 3.60-3.76 (m, 2H), 4.54-4.87 (m, 1H), 6.93-7.11 (m, 1H), 6.93-7.11 (m, 1H), 7.30-7.40 (m, 1H), 7.49-7.66 (m, 2H), 7.85 (d, 1H), 8.12 (s, 1H).

The Examples 8B-8F are examples of compounds of formula (Ib) and were prepared using similar methodology to that of Example 8A. Recrystallisation was required after chromatography for several Examples.

EXAMPLE 9A 4-(3,4-Dichlorophenoxy)-N-(4-methylbenzoyl)-[1,4'-bipiperidine]-1'-sulfonamide (an Example of a Compound of Formula (Ib)).

1,1-Dimethylethyl[4-(3,4-dichlorophenoxy)-1,4'-bipiperidin-1'-yl]sulfonylcarbamate (Method L; 400 mg) and triethylamine (0.5 ml) in dichloromethane (5 ml) at ambient temperature were treated with 4-methylbenzoylchloride (163 mg). The mixture was stirred overnight, the solvent was evaporated and the residue was dissolved in DMSO (1 ml)

and purified by HPLC (Waters XTerra® column) (acetonitrile/aqueous ammonia gradient) to give the title compound as a white solid (70 mg).

MS [M+H]$^+$ (APCI+) 526/528 (M+H) $^1$H NMR δ (DMSO) 1.51-1.61 (2H, m), 1.67-1.81 (2H, m), 1.86-1.96 (2H, m), 1.98-2.08 (2H, m), 2.33 (3H, s), 2.71-2.92 (5H, m), 2.98-3.09 (2H, m), 3.72 (2H, d), 4.52-4.61 (1H, m), 7.01 (1H, dd), 7.20 (2H, d), 7.30 (1H, d), 7.52 (1H, d), 7.82 (2H, d).

The Examples 9B and 9C are examples of compounds of formula (Ib) and were prepared using similar methodology to that of Example 9A.

EXAMPLE 10A

N-[[4-(3,4-Dichlorophenoxy)[1,4'-bipiperidin]-1'-yl]carbonyl]4-methyl-benzenesulfonamide, Sodium Salt (an Example of a Compound of Formula (Ia)).

To N-[[4-(3,4-dichlorophenoxy)[1,4'-bipiperidin]-1'-yl]carbonyl]-4-methyl-benzenesulfonamide (0.05 g) was added 0.1M sodium hydroxide (0.949 ml) and methanol (5 ml). The solution was stirred until all of the starting material had dissolved. The solvent was removed under reduced pressure to give the title compound.

Mpt 201° C. MS [M+H]$^+$ (APCI+) 526/528 $^1$H NMR δ (CD$_3$OD) 1.28-1.42 (2H, m), 1.70-1.82 (4H, m), 1.96-2.04 (2H, m), 2.35 (3H, s), 2.43-2.54 (3H, m), 2.56-2.66 (2H, m), 2.80-2.87 (2H, m), 4.34-4.42 (3H, m), 6.87-6.90 (1H, m), 7.09-7.10 (1H, m), 7.19-7.23 (2H, m), 7.35-7.38 (1H, m), 7.75-7.79 (2H, m).

The Examples 10B-10D are examples of compounds of formula (Ia) and were prepared using similar methodology to that of Example 10A.

EXAMPLE 11A 4-(3,4-Dichlorophenoxy)-N-[(1,2-dihydro-1-oxo-4-isoquinolinyl)carbonyl]-[1,4'-bipiperidine]-1'-sulfonamide (an Example of a Compound of Formula (Ib)).

To a solution of 1,1-dimethylethyl[[4-(3,4-dichlorophenoxy)[1,4'-bipiperidin]-1'-yl]sulfonyl]-carbamate (Method L; 0.305 g) in dichloromethane was added 1,2-dihydro-1-oxo-4-isoquinolinecarbonyl chloride (0.147 g, prepared from the corresponding acid by treatment with thionyl chloride at reflux) followed by triethylamine (0.097 ml) and the reaction was stirred under nitrogen for 12 h. The solvent was removed under reduced pressure with the resulting product dissolved in DMSO and purified by HPLC (Waters XTerra® column), (gradient, 75% aqueous (0.2% ammonia)/acetonitrile decreasing to 5% over 10 min) to give 1,1-dimethylethyl[[4-(3,4 dichlorophenoxy)[1,4'-bipiperidin]-1'-yl]sulfonyl][(1,2-dihydro-1-oxo-4-isoquinolinyl)carbonyl]-carbamate. (MS [M+H]$^+$ (ES+) 679/681).

1,1-Dimethylethyl[[4-(3,4 dichlorophenoxy)[1,4'-bipiperidin]-1'-yl]sulfonyl][(1,2-dihydro-1-oxo-4-isoquinolinyl)carbonyl]-carbamate was dissolved in dichloromethane (10 ml) followed by the addition of trifluoroacetic acid, (3 ml) and allowed to stir under nitrogen for 12 h. The solvent was removed under reduced pressure and the resulting product was dissolved in DMSO and purified by HPLC (Waters XTerra® column), (gradient, 90% aqueous (0.2% ammonia)/acetonitrile decreasing to 5% over 10 min) to give the title compound (0.028 g)

m.pt. 200° C. MS [M+H]$^+$ (ES+) 579/581 $^1$H NMR (399.98 MHz) δ (CD$_3$OD plus 1 drop NaOD) 1.58-1.69 (2H, m), 1.71-1.81 (2H, m), 1.92-2.05 (4H, m), 2.37-2.46 (1H, m), 2.48-2.56 (2H, m), 2.76-2.90 (4H, m), 0.84-3.90 (2H, m), 4.35-4.42 (1H, m), 6.86-6.90 (1H, m), 7.08 (1H, d), 7.30-7.34 (1H, m), 7.37 (1H, d), 7.49-7.54 (1H, m), 8.27-8.31 (1H, m), 8.44 (1H, s), 8.75 (1H, d)

EXAMPLE 12A

N-(Cyclohexylcarbonyl)-4-(3,4-dichlorophenoxy)-[1,4'-bipiperidine]-1'-sulfonamide (an Example of a Compound of Formula (Ib)).

To a solution of 1,1-dimethylethyl[[4-(3,4-dichlorophenoxy)[1,4'-bipiperidin]-1'-yl]sulfonyl]-carbamate (Method L; 0.305 g) in chloroform was added cyclohexanecarbonyl chloride (0.094 ml), triethylamine (0.097 ml) and dimethylaminopyridine (0.086 g). The reaction mixture was heated in a CEM Discover microwave at 300 W for 5 seconds reaching a temperature of 50° C.; pressure developed. The solvent was removed under reduced pressure and the resulting product was dissolved in DMSO and purified by HPLC (Waters XTerra® column), (gradient, 90% aqueous (0.2% ammonia)/acetonitrile decreasing to 5% over 10 min) to give the title compound (0.176 g) as a foam.

MS [M+H]$^+$ (ES+) 518/520 $^1$H NMR (399.98 kHz) δ (CD$_3$OD) 1.10-1.38 (5H, m), 1.44-1.62 (3H, m), 1.65-1.76 (6H, m), 1.82-1.89 (2H, m), 1.90-1.98 (2H, m), 2.07-2.16 (1H, m), 2.41-2.57 (3H, m), 2.72-2.86 (4H, m), 3.74-3.80 (2H, m), 4.30-4.37 (1H, m), 6.78-6.81 (1H, m), 7.02 (1H, d), 7.28 (1H, d)

EXAMPLE 13A 4-(3,4-Dichlorophenoxy)-N-(2-methyl-1-oxopropyl)-[1,4'-bipiperidine]-1'-sulfonamide (an Example of a Compound of Formula (Ib)).

To a solution of 4-(3,4-dichlorophenoxy)-[1,4'-bipiperidine]-1'-sulfonamide (Method G; 0.408 g) in dichloromethane (5 ml) was added 2-methyl-propanoyl chloride (0.126 ml), triethylamine (0.167 ml) and dimethylaminopyridine (0.147 g). The reaction was heated in a CEM Discover microwave at 50° C. using 50 W of power for 10 minutes. The solvent was removed under reduced pressure and the resulting product was dissolved in DMSO and purified by HPLC (Waters XTerra® column), (gradient, 90% aqueous (0.1% aqueous ammonium acetate)/acetonitrile decreasing to 5% over 10 min) to give the title compound (0.152 g) as a foam.

MS [M+H]$^+$ (ES+) 478/480 $^1$H NMR (399.98 MHz) δ (CD$_3$OD) 1.30 (6H, d), 1.75-1.91 (2H, m), 1.97-2.11 (2H, m), 0.13-2.32 (4H, m), 2.65 (1H, septet), 2.77-2.99 (3H, m), 3.02-3.12 (2H, m), 3.12-3.25 (2H, m), 4.04-4.15 (2H, m), 4.62-4.72 (1H, m), 7.09 (1H, dd), 7.31 (1H, d), 7.57 (1H, d)

EXAMPLE 14A 4-(3,4-Dichlorophenoxy)-N-(2-phenylacetyl)-[1,4'-bipiperidine]-1'-sulfonamide (an Example of a Compound of Formula (Ib)).

To a solution 4-(3,4-dichlorophenoxy)-[1,4'-bipiperidine]-1'-sulfonamide (Method G; 0.100 g) in THF (2 ml) was added potassium tert butoxide (0.083 g) followed after 1 h by phenylacetyl chloride (0.097 ml). After 12 h the solvent was evaporated and the resultant product was dissolved in methanol and loaded onto an Isolute® SCX cartridge which was washed with methanol and eluted with 10% ammonia in methanol. The solvent was evaporated and the residue was dissolved in DMSO and purified by HPLC (Waters XTerra® column), (gradient, 90% aqueous (0.2% ammonia)/acetonitrile decreasing to 75% over 10 min) to give the title compound (0.01 g).

MS [M+H]$^+$ (ES+) 526/528 $^1$H NMR (299.945 MHz) δ (CD$_3$OD plus 1 drop NaOD) 1.45-1.59 (2H, m), 1.70-1.89 (4H, m), 1.96-2.08 (2H, m), 2.23-2.35 (1H, m), 2.43-2.63 (4H, m), 2.77-2.88 (2H, m), 3.45 (2H, s), 3.66-3.75 (2H, m), 4.35-4.44 (1H, m), 6.88-6.94 (1H, m), 7.10-7.13 (1H, m), 7.14-7.30 (3H, m), 7.33-7.42 (3H, m)

EXAMPLE 15A

N-[[4-(3,4-Dichlorophenoxy)[1,4'-bipiperidin]-1'-yl]carbonyl]-2-propanesulfonamide (an Example of a Compound of Formula (Ia)).

To a solution 4-(3,4-dichlorophenoxy)-[1,4'-bipiperidine]-1'-carboxamide (Method H; 0.372 g) in THF (5 ml) was added potassium tert butoxide (0.337 g) followed after 1 h by 2-propanesulfonyl chloride (0.337 ml). After a further 2 h aqueous ammonium chloride was added and THF was evaporated to leave a precipitate which was collected. The precipitate was purified by HPLC (Waters XTerra® column), (gradient, 95% aqueous (0.2% ammonia)/acetonitrile decreasing to 50% over 10 min) to give the title compound (0.061 g).

MS [M+H]$^+$ (ES+) 478/480 $^1$H NMR (399.98 MHz) δ (CD$_3$OD plus 1 drop NaOD) 1.19 (6H, d), 1.23-1.37 (2H, m), 1.62-1.70 (2H, m), 1.71-1.78 (2H, m), 1.88-1.96 (2H, m), 2.34-2.47 (3H, m), 2.48-2.60 (2H, m), 2.72-2.80 (2H, m), 3.38-3.46 (1H, m), 4.27-4.37 (3H, m), 6.79 (1H, dd), 6.99 (1H, d), 7.28 (1H, d)

EXAMPLE 16A 4-(3,4-Dichlorophenoxy)-N-[(4-methylphenyl)sulfonyl]-[1,4'-bipiperidine)-1'-sulfonamide Sodium Salt (an Example of a Compound of Formula (Ie)).

4-(3,4-Dichlorophenoxy)-[1,4'-bipiperidine]-1'-sulfonamide (Method L; 582 mg), toluenesulfonyl chloride (380 mg) and DMAP (180 mg) were combined and dissolved in dichloromethane (10 ml). Triethylamine (0.3 ml) was added, followed after 35 min by a second portion of triethylamine (0.3 ml). The solution was stirred for 21 h and then concentrated. The residue was triturated with methanol and then THF to give a solid (0.65 g). A portion of the product (0.34 g) was dissolved in warm DMSO (30 ml). To this solution was added aqueous sodium hydroxide (1M, 6 ml) followed by water (200 ml). The solution was allowed to cool overnight and the title compound was collected (175 mg).

m. pt. 242-243° C. MS [M+H]$^+$ (ES+) 562/564

$^1$H NMR (399.98 MHz) δ$_{(DMSO)}$ 1.27 (2H, qd), 1.51-1.60 (2H, m), 1.65 (2H, d), 1.88-1.94 (2H, m), 2.23 (1H, tt), 2.31 (3H, s), 2.32-2.43 (4H, m), 2.68-2.75 (2H, m), 3.33-3.38 (2H, m), 4.37-4.43 (1H, m), 6.98 (1H, dd), 7.18 (2H, d), 7.25 (1H, d), 7.48 (1H, d), 7.60 (2H, d)

Example 16B (an example of a compound of formula (Ie)) was prepared using similar methodology to that of Example 16A and recrystallisation was required after chromatography.

| Example | Compound | MS [M + H]$^+$ (ES+) | $^1$H NMR δ | m. pt. ° C. |
|---|---|---|---|---|
| 1B Recrystallisation solvent DMSO | N-[[4-(3,4-Dichlorophenoxy)[1,4'-bipiperidin]-1'-yl]carbonyl]-4-methyl-benzenesulfonamide | 526/528 | (CD$_3$OD) 1.18-1.30(m, 2H), 1.62-1.74(m, 4H); 1.87-1.95 (m, 2H), 2.26(s, 3H), 2.32-2.43(m, 3H), 2.48-2.57(m, 2H), 2.70-2.76(m, 2H), 4.25-4.33(m, 3H), 6.77-6.81(m, 1H), 6.98-7.00(m, 1H), 7.11-7.15(m, 2H), 7.28(d, 1H), 7.65-7.68(m, 2H); 0.7 ml of CD$_3$OD plus 1 drop of NaOD (30% in D$_2$O) | 228.1-228.6 |
| 1C | N-[[4-(2,4-Dichloro-3-methylphenoxy)[1,4'-bipiperidin]-1'-yl]carbonyl]-4-methyl-benzenesulfonamide | 540/542 | (CD$_3$OD) 1.50-1.61(m, 2H), 1.97-2.04(m, 2H), 2.08-2.21 (m, 4H), 2.36(s, 3H), 2.47(s, 3H), 2.64-2.73(m, 2H), 3.22-3.40(m, 5H), 4.40-4.49(m, 2H), 4.70-4.76(m, 1H), 7.01-7.03(m, 1H), 7.22-7.24(m, 2H), 7.27-7.29(m, 1H), 7.76-7.79(m, 2H). | |
| 1D Recrystallisation solvent methanol | 4-Chloro-N-[[4-(3,4-dichlorophenoxy)[1,4'-bipiperidin]-1'-yl]carbonyl]-benzenesulfonamide | 546/548/550 | (CD$_3$OD) 1.18-1.28(m, 2H), 1.61-1.75(m, 4H), 1.87-1.94 (m, 2H), 2.33-2.43(m, 3H), 2.47-2.58(m, 2H), 2.70-2.77 (m, 2H), 4.25-4.32(m, 3H), 6.78-6.80(m, 1H), 6.99-7.00 (m, 1H), 7.27-7.34(m, 3H), 7.74-7.77(m, 2H); 0.7 ml of CD$_3$OD plus 1 drop of NaOD(30% in D$_2$O) | |
| 1E | N[[4-(3,4-Dichlorophenoxy)[1,4'-bipiperidin]-1'-yl]carbonyl]-2-methyl-benzenesulfonamide | 526/528 | (CD$_3$OD) 1.50-1.61(m, 2H), 2.01-2.11(m, 4H), 2.12-2.24 (m, 2H), 2.63-2.73(m, 2H), 2.64(s, 2H), 3.25-3.43(m, 5H), 4.43-4.52(m, 2H), 4.63-4.69(m, 1H), 6.94-6.98(m, 1H), 7.20-7.25(m, 1H), 7.30-7.35(m, 1H), 7.41-7.44(m, 1H), 7.95-7.99(m, 1H) | 160-161 |
| 1F | N-[[4-(3,4-Dichlorophenoxy)[1,4'-bipiperidin]-1'-yl]carbonyl]-benzenesulfonamide | 512/514 | (CD$_3$OD) 1.17-1.33(m, 2H), 1.59-1.76(m, 4H), 1.86-1.96 (m, 2H), 2.31-2.45(m, 3H), 2.47-2.59(m, 2H), 2.69-2.78 (m, 2H), 4.24-4.34(m, 3H), 6.77-6.81(m, 1H), 6.98-7.00 (m, 1H), 7.26-7.36(m, 4H), 7.76-7.81(m, 2H); plus 1 drop of 30% NaOD | 207-214 |
| 1G | N-[[4-(4-Chloro-2-methylphenoxy)[1,4'-bipiperidin]-1'-yl]carbonyl]-4-methyl-benzenesulfonamide | 506/508 | (CD$_3$OD) 1.49-1.61(m, 2H), 1.99-2.05(m, 2H), 2.06-2.14 (m, 2H), 2.15-2.23(m, 2H), 2.22(s, 3H), 2.36(s, 3H), 2.64-2.73(m, 2H), 3.22-3.39(m, 5H), 4.39-4.48(m, 2H), 4.60-4.66(m, 1H), 6.91-6.95(m, 1H), 7.10-7.17(m, 2H), 7.21-7.25(m, 2H), 7.75-7.80(m, 2H) | |
| 1H | N-[[4-(3,4-Dichlorophenoxy)[1,4'-bipiperidin]-1'-yl]carbonyl]-2-chloro-benzenesulfonamide | 546/548 | (CD$_3$OD) 1.17-1.36(m, 2H), 1.59-1.76(m, 4H), 1.85-1.97 (m, 2H), 2.31-2.45(m, 3H), 2.47-2.59(m, 2H), 2.68-2.78 (m, 2H), 4.24-4.37(m, 3H), 6.76-6.81(m, 1H), 6.98-7.00 (m, 1H), 7.21-7.36(m, 4H), 7.94-8.01(m, 1H); plus 1 drop of 30% NaOD in D$_2$O | |

-continued

| Example | Compound | MS [M + H]+ (ES+) | ¹H NMR δ | m. pt. ° C. |
|---|---|---|---|---|
| 1I | N-[[4-(2,4-Dichloro-3-methylphenoxy)[1,4'-bipiperidin]-1'-yl]carbonyl]-4-chloro-benzenesulfonamide | 560/562/564 | (CD₃OD) 1.19-1.31(m, 2H), 1.68-1.79(m, 4H), 1.84-1.93(m, 2H), 2.35(s, 3H), 2.37-2.46(m, 3H), 2.48-2.58 (m, 2H), 2.71-2.79(m, 2H), 4.24-4.34(m, 2H), 4.35-4.41 (m, 1H), 6.83-6.87(m, 1H), 7.14-7.17(m, 1H), 7.30-7.33 (m, 2H), 7.74-7.77(m, 2H) 1 drop of 30% NaOD added in D₂O | |
| 1J | N-[[4-[(3,4-dichlorophenyl)methyl][1,4'-bipiperidin]-1'-yl]carbonyl]-4-methyl-benzenesulfonamide | 524/526 | (CDCl₃) 7.79(3H, d), 7.32(1H, d), 7.20(1H, d), 7.13(1H, d), 6.89(1H, dd), 4.56(1H, s), 3.55(2H, d), 3.07(1H, s), 2.62 (4H, s), 2.35(5H, s), 2.02(1H, d), 1.66(7H, d) | 147-172 |
| 1K | 2-Chloro-N[[4-[(3,4-dichlorophenyl)methyl][1,4'-bipiperidin]-1'-yl]carbonyl]-benzenesulfonamide | 544/546/548 | (CD₃OD) 8.07(1H, dd), 7.47-7.31(5H, m), 7.09(1H, dd), 2.91(2H, d), 2.91(2H, d), 2.59(2H, t), 2.52(2H, d), 2.43-2.34(1H, m), 2.15(2H, d), 1.77(2H, d), 1.62(2H, d), 1.57-1.44(1H, m), 1.29(4H, d) | 212-239 |
| 1L | 4-Chloro-N-[[4-[(3,4-dichlorophenyl)methyl][1,4'-bipiperidin]-1'-yl]carbonyl]-benzenesulfonamide | 542/544/546 | (CD₃OD) 1.18-1.39(4H, m), 1.46-1.59(1H, m), 1.62(2H, d), 1.77(2H, d), 2.15(2H, dd), 2.34-2.44(1H, m), 2.49-2.65(4H, m), 2.90(2H, d), 4.34(2H, s), 7.09(1H, dd), 7.32 (1H, d), 7.38-7.43(3H, m), 7.84(2H, dt) | 164-184 |
| 1M | N-[[4-[(5-Chloro-2-pyridinyl)oxy][1,4'-bipiperidin]-1'-yl]carbonyl]-4-methyl-benzenesulfonamide | 493/495 | (DMSO) 8.20(1H, d), 7.81(1H, dd), 7.67(2H, d), 7.23 (2H, d), 6.87(1H, d), 5.09-5.01(1H, m), 4.16(2H, d), 3.13-3.00 (1H, m), 2.94-2.77(1H, m), 2.62-2.53(5H, m), 2.33(3H, s), 2.13-2.02(2H, m), 1.85-1.75(4H, m), 1.37-1.23(2H, m) | |
| 1N | 2-Chloro-N-[[4-(2-chloro-4-fluorophenoxy)[1,4'-bipiperidin]-1'-yl]carbonyl]-benzenesulfonamide | 530/532 | (CD₃OD) 1.44-1.56(m, 2H), 1.90-1.97(m, 2H), 1.98-2.15(m, 4H), 2.56-2.66(m, 2H), 3.20-3.40(m, 5H), 4.35-4.46(m, 2H), 4.54-4.64(m, 1H), 6.93-6.99(m, 1H), 7.07-7.11(m, 1H), 7.14-7.17(m, 1H), 7.24-7.35 (m, 3H), 7.99-8.02(m, 1H) | |
| 1O | N-[[4-(2-Chloro-4-fluorophenoxy)[1,4'-bipiperidin]-1'-yl]carbonyl]-4-methyl-benzenesulfonamide | 510/512 | (CD₃OD) 1.27-1.37(m, 2H), 1.78-1.87(m, 4H), 1.93-2.02(m, 2H), 2.35(s, 3H), 2.42-2.53(m, 3H), 2.57-2.67 (m, 2H), 2.82-2.89(m, 2H), 4.34-4.45(m, 3H), 6.97-7.03(m, 1H), 7.08-7.12(m, 1H), 7.16-7.20(m, 1H), 7.20-7.24(m, 2H), 7.74-7.77(m, 2H) 0.7 ml of CD3OD plus 1 drop of NaOD(30% in D2O) | 221-222 |
| 1P | N-[[4-(2,4-Dichloro-3-methylphenoxy)[1,4'-bipiperidin]-1'-yl]carbonyl]-benzenesulfonamide | ES+ 526/528 | (CD₃OD) 1.42-1.53(m, 2H), 1.89-1.95(m, 2H), 2.01-2.09(m, 4H), 2.37(s, 3H), 2.55-2.65(m, 2H), 3.17-3.34 (m, 5H), 4.32-4.41(m, 2H), 4.61-4.67(m, 1H), 6.91-6.94(m, 1H), 7.20-7.22(m, 1H), 7.30-7.37(m, 3H), 7.78-7.82(m, 2H) | |
| 1Q | N-[[4-(4-chlorophenoxy)[1,4'-bipiperidin]-1'-yl]carbonyl]-4-methyl-benzenesulfonamide | 492/494 | (CD₃OD plus 1 drop NaOD) 1.27-1.39(2H, m), 1.70-1.84 (4H, m), 1.96-2.04(2H, m), 2.36(3H, s), 2.40-2.51, (3H, m), 2.56-2.67(2H, m), 2.79-2.87(2H, m), 4.31-4.42 (3H, m), 6.89(2H, d), 7.20-7.24(4H, m), 7.76(2H, d) | 237-238 |
| 1R | N-[[4-(2,4-dichloro-3-methylphenoxy)[1,4'-bipiperidin]-1'-yl]carbonyl]-2-methyl-benzenesulfonamide | 540/542 | (CD₃OD plus 1 drop NaOD) 1.27-1.41(2H, m), 1.78-1.88 (4H, m), 1.93-2.02(2H, m), 2.44-2.55(3H, m), 2.44(3H, s), 2.57-2.67(2H, m), 2.66(3H, m), 2.81-2.89(2H, m), 4.35-4.51(3H, m), 6.95(1H, d), 7.19-7.34(4H, m), 7.94-7.97(1H, m) | |
| 1S | N-[[4-(2,4-dichloro-3-fluorophenoxy)[1,4'-bipiperidin]-1'-yl]carbonyl]-4-methyl-benzenesulfonamide | | (CDCl₃) 1.61(2H, q), 2.07(4H, t), 2.28(2H, t), 2.38(3H, s), 2.70(2H, t), 2.93-3.05(1H, m), 3.12(2H, t), 3.18-3.28 (2H, m), 4.45(2H, d), 4.60-4.67(1H, m), 6.79(1H, dd), 7.24(2H, d), 7.30(1H, d), 7.80(2H, d) | |
| 1T | N-[[4-(4-chloro-2-methylphenoxy)[1,4'-bipiperidin]-1'-yl]carbpnyl]-2-methyl-benzenesulfonamide | 506/508 | (CD₃OD) 1.40-1.55(3H, m), 1.91-2.03(6H, m), 2.13(3H, s), 2.56(3H, s), 2.56-2.64(3H, m), 3.23-3.30(3H, m), 4.34-4.44(2H, m), 4.50-4.56(1H, m), 6.80(1H, d), 7.00-7.07(2H, m), 7.11-7.16(2H, m), 7.20-7.25(1H, m), 7.84-7.88(1H, m) | 161 |
| 1U | 2-chloro-N-[[4-(4-chloro-2-methylphenoxy)[1,4'-bipiperidin]-1'-yl]carbonyl]benzenesulfonamide | 526/528 | (CD₃OD) 1.51-1.64(3H, m), 2.05(5H, d), 2.71(3H, t), 3.33-3.40(4H, m), 4.44-4.56(3H, m), 4.61-4.68(2H, m), 6.94(1H, d), 7.12(1H, dd), 7.34(1H, d), 7.35(1H, d), 7.38(1H, dd), 7.42-7.45(1H, m), 8.09(1H, dd) | 164 |
| 1V | 4-chloro-N-[[4-(4-chloro-2-methylphenoxy)[1,4'-bipiperidin]-1'-yl]carbonyl]-benzenesulfonamide | 526/528 | (CD₃OD) 1.68-1.82(2H, m), 2.09-2.15(4H, m), 2.17-2.21(3H, m), 2.37-2.48(2H, m), 2.59-2.71(2H, m), 2.99-3.14(3H, m), 3.40-3.52(2H, m), 4.49-4.63(3H, m), 6.68(1H, d), 7.07-7.16(2H, m), 7.36(2H, d), 7.88(2H, d) | 160 |

-continued

| Example | Compound | MS [M + H]+ (ES+) | 1H NMR δ | m. pt. ° C. |
|---|---|---|---|---|
| 1W | N-[[4-(2,4-dichlorophenoxy)[1,4'-bipiperidin]-1'-yl]carbonyl-4-methyl-benzenesulfonamide | 526/528 | (CD$_3$OD plus 1 drop NaOD) 1.27-1.40(2H, m), 1.77-1.88 (4H, m), 1.94-2.03(2H, m), 2.35(3H, s), 2.42-2.55(3H, m), 2.56-2.68(2H, m), 2.80-2.88(2H, m), 4.33-4.44 (2H, m), 4.45-4.52(1H, m), 7.08(1H, d), 7.21-7.25(3H, m), 7.38(1H, d), 7.76(2H, d) | |
| 1X | N-[[4-(3-chlorophenoxy)[1,4'-bipiperidin]-1'-yl]carbonyl]-4-methyl-benzenesulfonamide | 492/494 | (CD$_3$OD plus 1 drop NaOD) 1.30(2H, q), 1.71-1.83(4H, m), 1.94-2.04(2H, m), 2.34(3H, s), 2.40-2.50(3H, m), 2.56-2.68(2H, m), 2.75-2.83(2H, m), 4.32-4.43(3H, m), 6.81-6.89(3H, m), 7.22(1H, t), 7.22(2H, d), 7.76(2H, d) | 172-178 |
| 1Y | 2-chloro-N-[[4-(3-chlorophenoxy)[1,4'-bipiperidin]-1'-yl]carbonyl]-benzenesulfonamide | 512/514 | (CD$_3$OD plus 1 drop NaOD) 1.30-1.43(2H, m), 1.72-1.86 (4H, m), 1.97-2.03(2H, m), 2.42-2.53(3H, m), 2.58-2.67(2H, m), 2.80-2.87(2H, m), 4.35-4.46(3H, m), 6.85-6.94(3H, m), 7.22(1H, t), 7.32-7.46(3H, m), 8.08(1H, dd) | 180-186 |
| 1Z | N-[[4-(3-chlorophenoxy)[1,4'-bipiperidin]-1'-yl]carbonyl]-benzenesulfonamide | 478/480 | (CD$_3$OD plus 1 drop NaOD) 1.26-1.41(2H, m), 1.69-1.85 (4H, m), 1.95-2.04(2H, m), 2.41-2.53(3H, m), 2.57-2.68(2H, m), 2.79-2.88(2H, m), 4.34-4.46(3H, m), 6.83-6.94(3H, m), 7.22(1H, dt), 7.39-7.46(3H, m), 7.87-7.89 (2H, m) | 197-206 |
| 1AA | 2-chloro-N-[[4-(3-chloro-2-methylphenoxy)[1,4'-bipiperidin]-1'-yl]carbdnyl]-benzenesulfonamide | 526/528 | (CD$_3$OD plus 1 drop NaOD) 1.32-1.43(2H, m), 1.76-1.86 (4H, m), 1.95-2.04(2H, m), 2.25(3H, s), 2.46-2.55(3H, m), 2.59-2.69(2H, m), 2.79-2.87(2H, m), 4.35-4.48 (3H, m), 6.88(1H, d), 6.93(1H, d), 7.08(1H, t), 7.32-7.45 (3H, m), 8.08(1H, dd) | 223-234 |
| 1AB | N-[[4-(2-chloro-4-fluorophenoxy)[1,4'-bipiperidin]-1'-yl]carbonyl]-2-methyl-benzenesulfonamide | 510/512 | (DMSO) 1.17-1.46(2H, m), 1.65-2.16(8H, m), 2.57 (3H, s), 2.77-3.85(6H, m), 4.12-4.32(2H, m), 7.12-7.34(5H, m), 7.46(1H, dd), 7.78(1H, d) | 164-165 |
| 1AC | 2-chloro-N-[[4-(2,4-dichloro-3-fluorophenoxy)[1,4'-bipiperidin]-1'-yl]carbonyl]-benzenesulfonamide | 564/566/568 | (DMSO) 1.20-1.50(2H, m), 1.69-2.30(7H, m), 2.88-3.60(8H, m), 4.17-4.40(1H, m), 7.10-7.27(1H, m), 7.27-7.44(3H, m), 7.57(1H, t), 7.83-7.98(1H, m) | 172-173 |
| 1AD | 4-chloro-N-[[4-(2,4-dichloro-3-fluorophenoxy)[1,4'-bipiperidin]-1'-yl]carbonyl]-benzenesulfonamide | 564/566/568 | (DMSO) 1.21-1.48(2H, m), 1.64-2.25(6H, m), 2.88-3.40(9H, m), 4.10-4.41(1H, m), 7.18(1H, dd), 7.43(2H, d), 7.56(1H, t), 7.67-7.85(2H, d) | 167-168 |
| 1AE | N-[[4-(2,4-dichloro-3-fluorophenoxy)[1,4'-bipiperidin]-1'-yl]carbonyl]-2-methyl-benzenesulfonamide | 544/546 | (DMSO) 1.21-1.42(2H, m), 1.62-2.17(6H, m), 2.55(3H, s), 2.75-3.24(7H, m), 4.09-4.35(2H, m), 4.60-4.87(1H, m), 7.13-7.24(3.H, m), 7.28-7.37(1H, m), 7.55(1H, t), 7.80(1H, d) | 151-152 |
| 1AF | 2-chloro-N-[[4-(4-chlorophenoxy)[1,4'-bipiperidin]-1'-yl]carbonyl]-benzenesulfonamide | 512/514 | (DMSO) 1.23-1.53(2H, m), 1.62-2.39(7H, m), 2.92-3.68(6H, m), 4.13-4.44(2H, m), 4.44-4.91(1H, m), 6.95-7.17(2H, m), 7.30-7.45(5H, m), 7.82-8.01(1H, m) | 182-183 |
| 1AH | 4-chloro-N-[[4-(4-chlorophenoxy)[1,4'-bipiperidin]-1'-yl]carbonyl]-benzenesulfonamide | 512/514 | (DMSO) 1.11-1.37(3H, m), 1.47-2.20(7H, m), 2.55-3.24(6H, m), 4.04-4.64(2H, m), 7.00(2H, d), 7.32(2H, d), 7.39(2H, dt), 7.72(2H, dt) | 249-250 |
| 1AI | N-[[4-(4-chlorophenoxy)[1,4'-bipiperidin]-1'-yl]carbonyl]-2-methyl-benzenesulfonamide | 492/494 | (DMSO) 1.14-1.43(2H, m), 1.64-2.16(6H, m), 2.55(3H, s), 2.77-3.52(7H, m), 4.15-4.32(2H, m), 4.42-4.71(1H, m), 7.02(2H, d), 7.12-7.25(2H, m), 7.25-7.39(3H, m), 7.78(1H, d) | 153-154 |
| 1AJ | 2-chloro-N-[[4-(2,4-dichlorophenoxy)[1,4'-bipiperidin]-1'-yl]carbonyl]-benzenesulfonamide | 546/548/550 | (DMSO) 1.22-1.49(2H, m), 1.65-2.27(6H, m), 2.94-3.62(8H, m), 4.15-4.43(2H, m), 7.20-7.47(5H, m), 7.62 (1H, s), 7.83-8.02(1H, m) | 162-163 |
| 1AK | 4-chloro-N-[[4-(2,4-dichlorophenoxy)[1,4'-bipiperidin]-1'-yl]carbonyl] benzenesulfonamide. | 546/548/550 | (DMSO) 1.14-1.50(2H, m), 1.66-2.23(6H, m), 2.83-3.48(9H, m), 4.19-4.31(1H, m), 7.29(2H, d), 7.36-7.45 (2H, m), 7.61(1H, d) 7.68-7.88(2H, m) | 169-170 |

-continued

| Example | Compound | MS [M + H]+ (ES+) | 1H NMR δ | m. pt. ° C. |
|---|---|---|---|---|
| 1AL | N-[[4-(2,4-dichlorophenoxy)[1,4'-bipiperidin]-1'-yl]carbonyl]-2-methyl-benzenesulfonamide | 526/528 | (CD3OD) 1.73-2.06(6H, m), 2.42-2.63(6H, m), 2.66(3H, s), 2.78-2.92(3H, m), 4.35-4.54(3H, m), 7.08(1H, d), 7.19-7.26(3H, m), 7.28-7.34(1H, m), 7.39(1H, d), 7.91-8.02(1H, m) | 165-166 |
| 1AM | 2-chloro-N-[[4-(3,4-difluorophenoxy)[1,4'-bipiperidin]-1'-yl]carbonyl]-benzenesulfonamide | 514/516 | (DMSO) 1.28-1.47(2H, m), 1.59-2.40(6H, m), 2.90-3.60(7H, m), 4.16-4.42(2H, m), 4.44-4.92(1H, m), 6.77-6.92(1H, m), 7.07-7.45(5H, m), 7.81-7.98(1H, m) | 165-166 |
| 1AN | N-[[4-(3,4-difluorophenoxy)[1,4'-bipiperidin]-1'-yl]carbonyl]-2-methyl-benzenesulfonamide | 494 | (DMSO) 1.20-1.48(2H, m), 1.56-2.27(6H, m), 2.55(3H, s), 2.86-3.57(8H, m), 4.04-4.64(2H, m), 6.77-6.90(1H, m), 7.11-7.46(5H, m), 7.75-7.88(1H, d) | 147-148 |
| 1AO | N-[[4-(3,4-difluorophenoxy)[1,4'-bipiperidin]-1'-yl]carbonyl]-4-methyl-benzenesulfonamide | 494 | (DMSO) 1.18-1.44(2H, m), 1.57-2.20(6H, m), 2.53(3H, s), 2.63-3.53(7H, m), 4.11-4.23(2H, m), 4.38-4.67(1H, m), 6.78-6.85(1H, m), 7.09-7.18(1H, m), 7.22(2H, d), 7.34(1H, dd), 7.67(2H, d) | 140-141 |
| 1AP | N-[[4-(3-chloro-2-methylphenoxy)[1,4'-bipiperidin]-1'-yl]carbonyl]-4-methyl-benzenesulfonamide | 506/508 | (CD3OD plus 1 drop NaOD) 1.23-1.36(2H, m), 1.80(4H, d), 1.93-2.03(2H, m), 2.22(3H, s), 2.32(3H, s), 2.42-2.52(3H, m), 2.58-2.67(2H, m), 2.73-2.80(2H, m), 4.33-4.45(3H, m), 6.84(1H, d), 6.90(1H, d), 7.08(1H, t), 7.21(2H, d), 7.76(2H, d) | 206-210 |
| 1AQ | N-[[4-(3-chloro-2-methylphenoxy)[1,4'-bipiperidin]-1'-yl]carbonyl]-benzenesulfonamide | 492/494 | (CD3OD plus 1 drop NaOD) 1.28-1.45(2H, m), 1.79-1.89(4H, m), 1.97-2.08(2H, m), 2.26(3H, s), 2.42-2.70(5H, m), 2.79-2.89(2H, m), 4.37-4.48(3H, m), 6.89(1H, d), 6.94(1H, d), 7.09(1H, td), 7.39-7.47(3H, m), 7.87-7.92(2H, m) | 173-186 |
| 1AR | 3-chloro-N-[[4-(3,4-dichlorophenoxy)[1,4'-bipiperidin]-1'-yl]carbonyl]-benzenesulfonamide | 546/548/550 | (CD3OD) 1.23-1.44(4H, m), 1.70-1.87(4H, m), 1.99(2H, s), 2.49(2H, d), 2.56-2.70(1H, m), 2.83(2H, s), 4.38(3H, s), 6.88(1H, dd), 7.09(1H, d), 7.33-7.45(3H, m), 7.79(1H, dd), 7.88(1H, d) | 145-155 |
| 1AS | N-[[4-(2,4-dichloro-3-methylphenoxy)[1,4'-bipiperidin]-1'-yl]carbonyl]-4-fluoro-benzenesulfonamide | 544/546 | (CD3OD) 1.58(2H, td), 2.00-2.08(2H, m), 2.16(4H, d), 2.46(3H, s), 2.70(2H, t), 3.32-3.46(4H, m), 4.46(2H, d), 4.58(1H, s), 4.74(1H, s), 7.03(1H, d), 7.14(2H, t), 7.30(1H, d), 7.88-7.94(2H, m) | 147-169 |
| 1AT | 2-chloro-N-[[4-(2,4-dichloro-3-methylphenoxy)[1,4'-bipiperidin]-1'-yl]carbonyl]-benzenesulfonamide | 560/562/564 | (CD3OD plus 1 drop NaOD) 1.28-1.45(2H, m), 1.77-1.88(4H, m), 1.94-2.02(2H, m), 2.45(3H, s), 2.46-2.56(3H, m), 2.58-2.68(2H, m), 2.82-2.89(2H, m), 4.36-4.51(3H, m), 6.95(1H, d), 7.25(2H, d), 7.32-7.44(3H, m), 8.08-8.11(1H, m) | 216 |
| 1AU | N-[[4-(3,4-dichloro-2-methylphenoxy)[1,4'-bipiperidin]-1'-yl]carbonyl]-4-methyl-benzenesulfonamide | 540/2 | (CD3OD plus 1 drop NaOD) 1.28-1.41(2H, m), 1.76-1.85(4H, m), 1.96-2.05(2H, m), 2.31(3H, s), 2.35(3H, s), 2.43-2.56(3H, m), 2.57-2.67(2H, m), 2.77-2.85(2H, m), 4.34-4.47(3H, m), 6.91(1H, d), 7.22(2H, d), 7.27(1H, d), 7.76(2H, d) | 195-200 |
| 1AV | 2-chloro-N-[[4-(3,4-dichloro-2-methylphenoxy)[1,4'-bipiperidin]-1'-yl]carbonyl]-benzenesulfonamide | 560/562/564 | | 171 |
| 2B | 3-Cyano-N[[4-(3,4-dichlorophenoxy)[1,4'-bipiperidin]-1'-yl]carbonyl]-benzenesulfonamide | 537/539 | (CD3OD) 1.27-1.40(m, 2H), 1.70-1.85(m, 4H), 1.96-2.04(m, 2H), 2.43-2.53(m, 3H), 2.56-2,69(m, 2H), 2.79-2.86(m, 2H), 4.33-4.42(m, 3H), 6.86-6.90(m, 1H), 7.07-7.09(m, 1H), 7.36-7.39(m, 1H), 7.59-7.64(m, 1H), 7.78-7.81(m, 1H), 8.13-8.16(m, 1H), 8.21-8.22(m, 1H); plus 1 drop of NaOD, 30% in D2O | |
| 2C | N-[[4-(3,4-dichlorophenoxy)[1,4'-bipiperidin]-1'-yl]carbonyl]-3-(trifluoroniethyl)-benzenesulfonamide | 580/582 | (CD3OD) 1.40-1.53(m, 2H), 1.91-1.97(m, 4H), 2.01-2.16(m, 2H), 2.55-2.65(m, 2H), 3.17-3.36(m, 5H), 4.33-4.42(m, 2H), 4.55-4.62(m, 1H), 6.84-6.89(m, 1H), 7.11-7.13(m, 1H), 7.33(d, 1H), 7.51-7.56(m, 1H), 7.63-7.67(m, 1H), 8.02-8.05(m, 1H), 8.09(s, 1H) | 170-180 |
| 2D | N-[[4-(3,4-dichlorophenoxy)[1,4'-bipiperidin]-1'-yl]carbonyl]-4-methoxy-benzenesulfonamide | 542/544 | (CD3OD plus 1 drop NaOD) 1.28-1.40(2H, m), 1.70-1.84(4H, m), 1.96-2.04(2H, m), 2.42-2.53(3H, m), 2.56-2.66(2H, m), 2.78-2.86(2H, m), 3.81(3H, s), 4.34-4.42(3H, m), 6.87-6.90(1H, m), 6.91-6.95(2H, m), 7.09(1H, d), 7.37(1H, d), 7.79-7.83(2H, m) | |

-continued

| Example | Compound | MS [M + H]+ (ES+) | ¹H NMR δ | m. pt. ° C. |
|---|---|---|---|---|
| 2E | N-[[4-(3,4-dichlorophenoxy)[1,4'-bipiperidin]-1'-yl]carbonyl]-2,4,5-trifluoro-benzenesulfonamide | 566/568 | (CD₃OD plus 1 drop NaOD) 1.28-1.43(2H, m), 1.70-1.85 (4H, m), 1.96-2.05(2H, m), 2.43-2.54(3H, m), 2.57-2.69(2H, m), 2.80-2.88(2H, m), 4.33-4.43(3H, m), 6.88 (1H, dd), 7.09(1H, d), 7.20(1H, ddd), 7.37(1H, d), 7.79 (1H, ddd) | 223-228 |
| 2F | N-[[4-(3,4-dichlorophenoxy)[1,4'-bipiperidin]-1'-yl]carbonyl]-2,5-difluoro-benzenesulfonamide | 548/550 | (CD₃OD) 1.51-1.63(2H, m), 2.00-2.09(4H, m), 2.09-2.27(3H, m), 2.65-2.76(2H, m), 3.32-3.46(4H, m), 4.41-4.54(2H, m), 4.63-4.73(1H, m), 6.97(1H, dd), 7.12-7.24(3H, m), 7.43(1H, d), 7.59-7.63(1H, m) | 212-222 |
| 2G | N-[[4-(3,4-dichlorophenoxy)[1,4'-bipiperidin]-1'-yl]carbonyl]-4-(dimethylamino)-benzenesulfonamide | 555/557 | (CD₃OD plus 1 drop NaOD) 1.25-1.34(2H, m), 1.66-1.77 (4H, m), 1.94-2.02(2H, m), 2.39-2.47(3H, m), 2.52-2.61(2H, m), 2.75-2.83(2H, m), 2.97(6H, s), 4.31-4.43 (3H, m), 6.67-6.70(2H, m), 6.93(1H, dd), 7.14(1H, d), 7.42(1H, d), 7.64-7.68(2H, m) | 194-196 |
| 2H | N-[[4-(3,4-dichlorophenoxy)[1,4'-bipiperidin]-1'-yl]carbonyl]-2-methoxy-benzenesulfonamide | 542/544 | (CD₃OD) 1.28-1.41(2H, m), 1.71-1.84(4H, m), 1.96-2.04(2H, m), 2.42-2.53(3H, m), 2.57-2.66(2H, m), 2.80-2.87(2H, m), 3.89(3H, s), 4.35-4.44(3H, m), 6.88(1H, dd), 6.94-6.99(1H, m), 7.05-7.10(2H, m), 7.37(1H, d), 7.40-7.44(1H, m), 7.87(1H, dd) | 215-218 |
| 2I | 4-bromo-N-[[4-(3,4-dichlorophenoxy)[1,4'-bipiperidin]-1'-yl]carbonyl]-benzenesulfonamide | 590/592/594 | | 220-223 |
| 2J | 3,5-dichloro-N-[[4-(3,4-dichlorophenoxy)[1,4'-bipiperidin]-1'-yl]carbonyl]-benzenesulfonamide | 580/582/584 | | |
| 2K | Methyl 2-[[[[4-(3,4-dichlorophenoxy)[1,4'-bipiperidin]-1'-yl]carbonyl]amino]sulfonyl]-benzoate | 570/572 | | |
| 2L | 2-bromo-N-[[4-(3,4-dichlorophenoxy)[1,4'-bipiperidin]-1'-yl]carbonyl]-benzenesulfonamide | 590/592/594 | | |
| 2M | 5-chloro-N-[[4-(3,4-dichlorophenoxy)[1,4'-bipiperidin]-1'-yl]carbonyl]-2-thiophenesulfonamide | 552/554/556 | | |
| 2N | 4,5-dichloro-N-[[4-(3,4-dichlorophenoxy)[1,4'-bipiperidin]-1'-yl]carbonyl]-2-thiophenesulfonamide | 586/588/590 | | |
| 2O | 4-chloro-N-[[4-(3,4-dichlorophenoxy)[1,4'-bipiperidin]-1'-yl]carbonyl]-2,5-dimethyl-benzenesulfonamide | 574/576/578 | | |
| 2P | 2,5-dichloro-N-[[4-(3,4-dichlorophenoxy)[1,4'-bipiperidin]-1'-yl]carbonyl]-3-thiophenesulfonamide | 586/588/590 | | |
| 2Q | N-[[4-(3,4-dichlorophenoxy)[1,4'-bipiperidin]-1'-yl]carbonyl]-2-(trifluoromethoxy)-benzenesulfonamide | 596/598 | | |

-continued

| Example | Compound | MS [M + H]+ (ES+) | ¹H NMR δ | m. pt. ° C. |
|---|---|---|---|---|
| 2R | 4-bromo-N-[[4-(3,4-dichlorophenoxy)[1,4'-bipiperidin]-1'-yl]carbonyl]-2-thiophenesulfonamide | 596/598/600 | | |
| 2S | N-[[4-(3,4-dichlorophenoxy)[1,4'-bipiperidin]-1'-yl]carbonyl]-4-(trifluoromethoxy)-benzenesulfonamide | 596/598 | | |
| 2T | 5-chloro-N-[[4-(3,4-dichlorophenoxy) [1,4'-bipiperidin]-1'-yl]carbonyl]-2,4-difluoro-benzenesulfonamide | 582/584/586 | | |
| 2U | 4-chloro-N-[[4-(3,4-dichlorophenoxy)[1,4'-bipiperidin]-1'-yl]carbonyl]-2,5-difluoro-benzenesulfonamide | 582/584/586 | | |
| 2V | 3-chloro-N-[[4-(3,4-dichlorophenoxy)[1,4'-bipiperidin]-1'-yl]carbonyl]-5-fluoro-2-methyl-benzenesulfonamide | 578/580/582 | | |
| 2X | N-[[4-(3,4-dichlorophenoxy)[1,4'-bipiperidin]-1'-yl]carbonyl]-2,6-dimethyl-benzenesulfonamide | 540/542 | (CD₃OD plus 1 drop NaOD) 1.53(2H, dd), 1.98-2.24(7H, m), 2.63-2.74(2H, m), 2.72(6H, s), 3.20-3.39(4H, m), 4.43(2H, d), 4.63-4.69(1H, m), 6.96(1H, dd), 7.05(2H, d), 7.14(1H, dd), 7.21(1H, d), 7.42(1H, d) | |
| 2Y | N-[[4-(3,4-dichlorophenoxy)[1,4'-bipiperidin]-1'-yl]carbonyl]-2-(dimethylamino)-benzenesulfonamide | 555/557 | (CD₃OD plus 1 drop NaOD) 1.27-1.42(2H, m), 1.70-1.86 (4H, m), 1.96-2.05(2H, m), 2.41-2.54(3H, m), 2.57-2.67(2H, m), 2.73(6H, s), 2.80-2.88(2H, m), 4.35-4.47 (3H, m), 6.88(1H, dd), 7.08-7.14(2H, m), 7.30-7.43(3H, m), 7.98(1H, dd) | |
| 2Z | N-[[4-(3,4-dichlorophenoxy)[1,4'-bipiperidin]-1'-yl]carbonyl]-4-(ethylamino)-benzenesulfonamide | 555/557 | (DMSO) 1.15(3H, t), 1.20-1.28(2H, m), 1.53-1.63(2H, m), 1.65-1.72(2H, m), 1.88-1.96(2H, m), 2.37-2.47 (3H, m), 2.57-2.68(2H, m), 2.70-2.79(2H, m), 3.08(2H, dt), 3.94-4.01(2H, m), 4.39-4.47(1H, m), 6.38-6.43 (1H, m), 6.53-6.58(2H, m), 6.97(1H, m), 7.25(1H, d), 7.48-7.51(1H, m), 7.53-7.57(2H, m) | |
| 5B | N-Benzoyl-4-(4-chloro-2-methylphenoxy)-[1,4'-bipiperidine]-1'-sulfonamide | 492/494 | (CD₃OD) 1.57-1.73(m, 2H), 1.75-1.88(m, 2H), 1.90-2.07(m, 4H), 2.19(s, 3H), 2.37-2.49(m, 1H), 2.50-2.61 (m, 2H), 2.73-2.91(m, 4H), 3.80-3.90(m, 2H), 4.36-4.45(m, 1H), 6.87-6.91(m, 1H), 7.07-7.13(m, 2H), 7.32-7.46(m, 3H), 8.04(d, 2H); (plus 1 drop of 30% NaOD in D₂O) | 237-238 |
| 5C | N-Benzoyl-4-[(3,4-dichlorophenyl)methyl]-[1,4'-bipiperidine]-1'-sulfonamide | 510/512 | (CD₃OD) 8.00(2H, dt), 7.43-7.37(2H, m), 7.36-7.29(3H, m), 7.09(1H, dd), 3.81(2H, d), 2.94(2H, d), 2.74(2H, t), 2.53(2H, d), 2.35(1H, t), 2.18(2H, t), 1.89(3H, s), 1.67-1.48(5H, m), 1.33-1.21(2H, m) | 193-196 |
| 5D | N-Benzoyl-4-(3,4-dichloro-2-methylphenoxy)-[1,4'-bipiperidine]-1'-sulfonamide | 526/528 | (CD₃OD plus 1 drop NaOD) 1.58-1.70(2H, m), 1.76-1.86 (2H, m), 1.90-1.96(2H, m), 1.97-2.05 (2H, m), 2.31(3H, s), 2.38-2.47(1H, m), 2.51-2.58(2H, m), 2.74-2.88(4H, m), 3.81-3.87(2H, m), 4.40-4.47(1H, m), 6.91(1H, d), 7.27(1H, d), 7.31-7.36(2H, m), 7.38-7.43(1H, m), 8.00-8.03 (2H, m) | 198-199 |
| 5E | N-benzoyl-4-(2,4-dichlorophenoxy)-[1,4-bipiperidine]-1'-sulfonamide | 512/514 | (CD₃OD plus 1 drop NaOD) 1.58-1.70(2H, m), 1.79-1.88 (2H, m); 1.90-2.04(4H, m), 2.38-2.47(1H, m), 2.51-2.58(2H, m), 2.74-2.82(2H, m), 2.84-2.92(2H, m), 3.81-3.87(2H, m), 4.45-4.52(1H, m), 7.08(1H, d), 7.23(1H, dd), 7.31-7.36(2H, m), 7.39-7.43(2H, m), 8.00-8.03 (2H, m) | 233-235 |
| 6B | trans N-[[4-[4-(3,4-dichlorophenoxy)-1-piperidinyl]cyclohexyl]carbonyl]-2-methyl-benzenesulfonamide | 525/527 | (CD₃OD) 1.33(4H, d), 1.66-1.79(2H, m), 1.83-2.12(7H, m), 2.25-2.37(1H, m), 2.50(2H, s), 2.64(3H, s), 2.78-2.89(2H, m), 4.32-4.40(1H, m), 6.87(1H, dd), 7.08(1H, d), 7.22(2H, d), 7.30-7.34(1H, m), 7.36(1H, d), 7.98(1H, d) | |

-continued

| Example | Compound | MS [M + H]+ (ES+) | $^1$H NMR δ | m. pt. ° C. |
|---|---|---|---|---|
| 6C | trans N-[[4-[4-(3,4-dichlorophenoxy)-1-piperidinyl]cyclohexyl]carbonyl]-2-methoxy-benzenesulfonamide | 541/543 | (CD$_3$OD) 1.27-1.45(4H, m), 1.70-1.81(2H, m), 1.85-2.19(7H, m), 2.24-2.39(1H, m), 2.45-2.58(2H, m), 2.80-2.91(2H, m), 3.89(3H, s), 4.33-4.44(1H, m), 6.85-7.13 (4H, m), 7.35-7.50(2H, m), 7.87-7.92(1H, m) | |
| 6D | trans N-[[4-[4-(3,4-dichlorophenoxy)-1-piperidinyl]cyclohexyl]carbonyl]-2,6-dimethyl-benzenesulfonamide | 539/541 | (CD$_3$OD) 1.34(4H, d), 1.64-1.80(2H, m), 1.85-2.14(7H, m), 2.25-2.37(1H, m), 2.45-2.57(2H, m), 2.73(6H, s), 2.80-2.90(2H, m), 4.32-4.41(1H, m), 6.85-6.92(1H, m), 7.00-7.21(4H, m), 7.38(1H, d) | |
| 6E | trans N-[[4-[4-(3,4-dichlorophenoxy)-1-piperidinyl]cyclohexyl]carbonyl]-4-methyl-benzenesulfonamide | 525/527/529 | (CD$_3$OD plus 1 drop NaOD) 1.26-1.41(4H, m), 1.72-1.82 (2H, m), 1.88-2.13(7H, m), 2.28-2.37(1H, m), 2.40(3H, s), 2.53(2H, s), 2.86(2H, s), 4.40(1H, s), 6.90(1H, dd), 7.11(1H, d), 7.27(2H, d), 7.39(1H, d), 7.79(2H, d); | |
| 6F | trans N-[[4-[4-(3,4-dichlorophenoxy)-1-piperidinyl]cyclohexyl]carbonyl]-benzenesulfonamide | 511/513/515 | (CD$_3$OD plus 1 drop NaOD) 6.78(1H, d), 6.99(1H, d), 7.27 (1H, d), 7.30-7.38(3H, m), 7.76-7.83(2H, m) (of aromatic region only) | |
| 6G | tarns N-[[4-[4-(3,4-dichlorophenoxy)-1-piperidinyl]cyclohexyl]carbonyl]-4-(dimethylamino)-benzenesulfonamide | 554/556/558 | (CD$_3$OD plus 1 drop NaOD) 1.27-1.46(4H, m), 1.71-1.85 (2H, m), 1.88-2.12(7H, m), 2.31-2.40(1H, m), 2.53(2H, t), 2.86(2H, d), 3.03(6H, s), 4.36-4.45(1H, m), 6.73(2H, d), 6.91(1H, dd), 7.11(1H, d), 7.40(1H, d), 7.74(2H, d) | |
| 8B | N-(3-cyanobenzoyl)-4-(3,4-dichlorophenoxy)-[1,4-bipiperidine]-1-sulfonamide | 537/539 | (DMSO) 1.55-1.80(4H, m), 1.92-2.18(6H, m), 2.63-2.75(2H, m), 3.00-3.26(4H, m), 3.59-3.77(2H, m), 6.96-7.11(1H, m), 7.29-7.41(1H, m), 7.44-7.63(2H, m), 7.85(1H, d), 8.21(2H, dt) | 254-255 |
| 8C | 4-(3,4-dichlorophenoxy)-N-(4-fluorobenzoyl)-[1,4'-bipiperidine]-1'-sulfonamide | 530/532 | (DMSO) 1.55-1.80(3H, m), 1.92-2.18(6H, m), 2.63-2.75(2H, m), 3.00-3.26(4H, m), 3.59-3.77(2H, m) 3.59-3.78(1H, m), 6.89-7.24(3H, m), 7.33(1H, s), 7.53(1H, d), 7.96(2H, dd) | 141-143 |
| 8D | 4-(3,4-dichlorophenoxy)-N-[3-(methylsulfonyl)benzoyl]-[1,4'-bipiperidine]-1'-sulfonamide | 590/592 | (DMSO) 1.46-2.20(10H, m), 2.62-2.80(6H, m), 3.24 (3H, s), 3.66-3.76(2H, m), 7.04(1H, s), 7.35(1H, s), 7.54 (1H, d), 7.62(1H, t), 7.95(1H, d), 8.23(1H, dt), 8.42(1H, t) | 244-246 |
| 8E | 4-(4-chloro-2-methylphenoxy)-N-[3-(methylsulfonyl)benzoyl]-[1,4-bipiperidine]-1'-sulfonamide | 570/572 | (DMSO) 1.51-1.79(4H, m), 1.91-2.24(8H, m), 2.64-2.75(3H, m), 3.20(3H, s), 3.66-3.75(2H, m), 4.43-4.81 (1H, m), 6.98-7.05(1H, m), 7.19(1H, dd), 7.24(1H, d), 7.62(1H, t), 7.94(1H, d), 8.23(1H, dt), 8.42(1H, t) | 235-236 |
| 8F | N-(2-chlorobenzoyl)-4-(3,4-dichlorophenoxy)-[1,4-bipiperidine]-1'-sulfonamide | 546/548/550 | (DMSO) 1.44-1.73(4H, m), 1.86-2.17(6H, m), 2.63-2.77(2H, m), 3.03-3.16(4H, m), 3.64-3.72(2H, m), 7.03 (1H, d), 7.32-7.42(3H, m), 7.54(1H, d), 7.92(2H, dt) | 187-188 |
| 8G | N-(4-chlorobenzoyl)-4-(3,4-dichlorophenoxy)-[1,4'-bipiperidine]-1'-sulfonamide | 546/548/550 | (DMSO) 0.92-2.22(11H, m), 2.57-2.78(6H, m), 3.63-3.77(1H, m), 7.03(1H, d), 7.31-7.41(3H, m), 7.54(1H, d), 7.92(2H, dd) | 156-157 |
| 8H | N-(4-chlorobenzoyl)-4-(4-chloro-2-methylphenoxy)-[1,4'-bipiperidine]-1'-sulfonamide | 526/528 | (DMSO) 1.02-1.61(4H, m), 1.63-2.03(3H, m), 2.13-2.19(2H, m), 2.52(3H, s), 2.56-2.69(3H, m), 2.97-3.14 (4H, m), 3.52-3.78(2H, m), 7.00(1H, d), 7.16(1H, dd), 7.22(1H, d), 7.32-7.39(2H, m), 7.91(2H, dt) | 138-139 |
| 9B | 4-(3,4-dichlorophenoxy)-N-(2-methoxybenzoyl)-[1,4'-bipiperidine]-1'-sulfonamide | 542/544 | (DMSO) 0.95-1.31(3H, m), 1.31-1.96(6H, m), 2.24(3H, s), 2.57-2.75(7H, m), 3.55-3.73(2H, m), 6.95-7.05(2H, m), 7.13(1H, d), 7.26(1H, d), 7.47(3H, dd) | 202-203 |
| 9C | 4-(3,4-dichlorophenoxy)-N-(4-methoxybenzoyl)-[1,4'-bipiperidine]-1'-sulfonamide | 542/544 | (DMSO) 1.40-2.19(6H, m), 2.70-2.89(5H, m), 2.95-3.13(2H, m), 3.68-3.79(4H, m), 3.87(3H, s), 4.43-4.66 (1H, m), 6.95(2H, d), 7.01(1H, dd), 7.30(1H, d), 7.52(1H, d), 7.90(2H, dd) | 142-143 |
| 10B | N-[[4-(3,4-dichlorophenoxy)[1,4'-bipiperidin]-1'-yl]carbonyl]-2-methylbenzenesulfonamide sodium salt | 526/528 | (DMSO) 1.16(2H, qd), 1.50-1.61(4H, m), 1.87-1.94(2H, m), 2.28-2.46(5H, m), 2.69-2.75(2H, m), 4.18-4.27 (2H, m), 4.39(1H, septet), 6.97(1H, dd), 7.11(2H, t), 7.20 (1H, td), 7.25(1H, d), 7.48(1H, d), 7.74(1H, d) | |

-continued

| Example | Compound | MS [M + H]+ (ES+) | ¹H NMR δ | m. pt. ° C. |
|---------|----------|-------------------|----------|-------------|
| 10C | N-[[4-(3,4-dichlorophenoxy)[1,4'-bipiperidin]-1'-yl]carbonyl]-benzenesulfonamide sodium salt | 512/514 | (DMSO) 1.16(2H, qd), 1.49-1.62(4H, m), 1.87-1.94(2H, m), 2.27-2.46(5H, m), 2.69-2.75(2H, m), 4.17-4.26 (2H, m), 4.39(1H, septet), 6.97(1H, dd), 7.25(1H, d), 7.29-7.33(3H, m), 7.48(1H, d), 7.69-7.72(2H, m) | |
| 10D | N-[[4-(4-chloro-2-methylphenoxy)[1,4'-bipiperidin]-1'-yl]carbonyl]-4-methyl-benzenesulfonamide sodium salt | 506/508 | (DMSO) 1.10-1.21(2H, m), 1.54-1.65(4H, m), 1.83-1.91(2H, m), 2.28(3H, s), 2.12(3H, d), 2.30-2.46(5H, m), 2.65-2.72(2H, m), 4.20(2H, d), 4.32-4.39(1H, m), 6.97 (1H, d), 7.10(2H, d), 7.13(1H, dd), 7.19(1H, dd), 7.58 (2H, d) | |
| 16B | 4-(3,4-dichlorophenoxy)-N-[[4-(1,1-dimethylethyl)phenyl]sulfonyl]-[1,4'-bipiperidine]-1'-sulfonamide | 604/606/608 | | 274-276 recrystallised from DMSO-methanol. |

The preparations of certain intermediates are now presented.

Method A

[1,4']Bipiperidinyl-4-ol

4-Oxo-piperidine-1-carboxylic acid tert-butyl ester (20 g) and 4-hydroxypiperidine (6.7 g) were stirred together in dichloroethane (200 ml) with acetic acid (4 ml) at RT for 30 minutes. Sodium triacetoxyborohydride (23 g) was then added and the mixture stirred at RT overnight. The mixture was evaporated to dryness and the residue taken into water, extracted with diethyl ether (3×200 ml), the aqueous was basified to pH 9-10 and extracted with dichloromethane (3×200 ml). The dichloromethane extracts were combined, dried (MgSO₄) and evaporated to leave an oil (19 g). The oil was dissolved in methanol (300 ml) and treated with concentrated hydrochloric acid (5 ml). The mixture was stirred overnight and then evaporated to dryness to leave the title compound as the hydrochloride salt (15 g).

¹H NMR (400 MHz, DMSO-D6) δ 1.6-2.4 (m, 9H), 2.8-3.5 (m, 8H), 3.62 (m, 1H), 3.95 (s, 1H), 9.29 and 9.059 (bs, 2H), 10.9 and 11.09 (bs, 1H).

Method B 4-(3,4-Dichlorophenoxy)piperidine

Step a: tert-Butyl 4-(3,4-dichlorophenoxy)-1-piperidinecarboxylate

Diethyl azodicarboxylate (41.0 ml) was added to a solution of triphenylphosphine (62.9 g) in tetrahydrofuran (800 ml) at 0° C. After 15 minutes 3,4-dichlorophenol (39.1 g) was added, after a further 15 minutes tert-butyl 4-hydroxy-1-piperidinecarboxylate (48.3 g) in tetrahydrofuran (400 ml) was added dropwise over 30 min. The solution was stirred at room temperature for 16 hours and concentrated to a small volume. Purification by chromatography (ethyl acetate:isohexane 95:5) gave the sub-title compound as an oil (61.3 g).

MS: APCI(+ve): 246/248 (M-BOC+2H)

Step b: 4-(3,4-Dichlorophenoxy)piperidine

The product from Step a was dissolved in dichloromethane (600 ml) and trifluoroacetic acid (300 ml) was added. After 24 hours at room temperature the solution was evaporated and the resultant gum triturated under ether to give the sub-title product as a solid (36.6 g). The free base was liberated by addition of aqueous NaOH (2M) and extraction with ethyl acetate followed by evaporation of solvent to give the title compound as a gum (25 g).

¹H NMR: δ (CDCl₃) 1.77 (1H, br s), 2.05-2.26 (4H, m), 3.20-3.49 (4H, m), 4.61 (1H, s), 6.69-7.52 (3H, m).

Method C 4-(3,4-Dichlorophenoxy)-[1,4']bipiperidine

Step a: 4-(3,4-Dichlorophenoxy)-[1,4']bipiperidinyl-1'-carboxylic acid tert-butyl ester 4-(3,4-Dichlorophenoxy)piperidine (1.5 g) was dissolved in 1,2-dichloroethane (21 ml). 1-Boc-4-piperidone was added (1.21 g) followed by NaBH(OAc)₃ (1.81 g) and acetic acid (0.37 g). After 18 hours at room temperature aqueous NaOH (1M) solution and diethyl ether were added. The product was extracted with diethyl ether, the combined organic extracts dried with MgSO₄ and concentrated. Purification by chromatography (dichloromethane methanol 92:8) gave the sub-title product (1.97 g; MS: APCI(+ve): 429/431 (M+H)).

Step b: 4-(3,4-Dichloro-phenoxy)-[1,4']bipiperidine

The product of Step a was dissolved in dichloromethane (30 ml) and trifluoroacetic acid (15 ml) was added. After 4 hours at room temperature the solution was evaporated and the resultant gum triturated under ether to give the trifluoroacetate salt of the sub-titled product as a solid (1.15 g). The free base was liberated by addition of aqueous NaOH (2M) and extraction with ethyl acetate followed by evaporation of solvent to give the sub-title compound as a solid (0.68 g).

¹H NMR: δ(CDCl₃) 1.38-1.51 (2H, m), 1.74-2.02 (6H, m), 2.38-2.50 (3H, m), 2.56-2.61 (2H, m), 2.79-2.86 (2H, m), 3.14-3.18 (2H, m), 4.22-4.28 (1H, m), 6.73-7.32 (3H, m).

The following intermediates were prepared in a similar manner to Method C:

| | MS: (M + H) |
|---|---|
| 4-(4-chloro-2-methylphenoxy)-1,4'-bipiperidine | 309/311 |
| 4-(2-chloro-4-fluorophenoxy)-1,4'-bipiperidine | 313/315 |
| 4-(3,4-diflorophenoxy)-1,4'-bipiperidine | 297 |
| 4-(2,4-dichlorophenoxy)-1,4'-bipiperidine | 329/331 |
| 4-(2,4-dichloro-3-methylphenoxy)-1,4'-bipiperidine | 343/345 |
| 4-(3,4-dichloro-2-methylphenoxy)-1,4'-bipiperidine | 343/345 |
| [1] 4-[(3,4-Dichlorophenyl)methyl]-1,4'-bipiperidine | 327/329 |
| [2] 2-([1,4'-bipiperidin]-4-yloxy)-5-chloro-pyridine | [3] |

[1] for starting material see DE19837386
[2] for starting material see WO 00/12478
[3] $^1$H NMR (399.978 MHz, CDCl$_3$): δ 1.44(2H, qd), 1.74-1.86(5H, m), 2.01-2.07(2H, m), 2.38-2.42(1H, m), 2.44-2.50(2H, m), 2.60(2H, td), 2.82-2.87(2H, m), 3.15(2H, d), 4.98(1H, septet), 6.66(1H, d), 7.50(1H, dd), 8.06(1H, d).

Method D

4-(3-Chloro-4-fluoro-phenoxy)-piperidine

DEAD (0.43 ml) was added to a solution of triphenylphosphine (0.72 g), 3-chloro-4-fluorophenol (0.403 g) and 4-hydroxy-piperidine-1-carboxylic acid tert-butyl ester (0.5 g) in THF at RT. The resulting mixture was stirred overnight, HCl in dioxan (2 ml of 4M) was added and the mixture stirred at RT overnight. The mixture was then evaporated to dryness and triethylamine (5 ml) was added. The mixture was evaporated and the residue was dissolved in methanol (10 ml), placed onto a SCX cartridge (Varian, 10 g, SCX cartridge available from International Sorbent Technology Isolute® Flash SCX-2) and eluted: first with methanol then with 10% NH$_3$ in methanol. The basic fractions were combined and evaporated to give the product as an oil (0.6 g).

$^1$H NMR (299.946 MHz, DMSO-D6) δ 1.34-1.46 (2H, m), 1.83-1.91 (2H, m), 2.53-2.59 (2H, m), 2.87-2.96 (2H, m), 3.22-3.39 (1H, m), 4.39 (1H, septet), 6.92-6.98 (1H, m), 7.17-7.20 (1H, m), 7.30 (1H, t).

The following intermediates were prepared in similar manner to Method D:

| | MS: (M + H) |
|---|---|
| 4-(4-chloro-2-methyl-phenoxy)-piperidine | 226/228 |
| 4-(4-chloro-3-fluoro-phenoxy)-piperidine | 230/232 |
| 4-(4-chloro-2-methoxy-phenoxy)-piperidine | 242/244 |
| 4-(4-fluoro-2-methoxy-phenoxy)-piperidine | 226 |
| 4-(4-methoxy-phenoxy)-piperidine | 208 |
| 4-p-tolyloxy-piperidine | 192 |
| 4-(4-chloro-3-methyl-phenoxy)-piperidine | 226/228 |
| 4-(4-chloro-phenoxy)-piperidine | 212/214 |
| 4-(4-fluoro-phenoxy)-piperidine | 196 |
| 4-(2,4-dichloro-phenoxy)-piperidine | 246/248 |
| 4-(2-chloro-4-fluoro-phenoxy)-piperidine | 230/232 |
| 4-(2,4-difluoro-phenoxy)-piperidine | 214 |
| 4-(4-chloro-2-fluoro-phenoxy)-piperidine | 230/232 |
| 4-(4-fluoro-2-methyl-phenoxy)-piperidine | 210 |
| 4-(4-chloro-2,6-dimethyl-phenoxy)-piperidine | 240/242 |
| 4-(2,3-dichloro-phenoxy)-piperidine | 246/248 |
| 4-(2,5-dichloro-phenoxy)-piperidine | 246/248 |
| 4-(2-chloro-4-methyl-phenoxy)-piperidine | 226/228 |
| 4-(2-chloro-5-methyl-phenoxy)-piperidine | 226/228 |
| 1-[3-methyl-4-(piperidin-4-yloxy)-phenyl]-ethanone | 234 |
| 4-(2-chloro-6-methyl-phenoxy)-piperidine | 226/228 |
| 4-(4-chloro-2-ethyl-phenoxy)-piperidine | 240/242 |

-continued

| | MS: (M + H) |
|---|---|
| 7-(piperidin-4-yloxy)-quinoline | 229 |
| 4-(2-tert-butyl-phenoxy)-piperidine | 234 |
| 4-(indan-5-yloxy)-piperidine | 218 |
| 4-(4-chloro-2-cyclohexyl-phenoxy)-piperidine | 294/296 |
| 5-chloro-2-(piperidin-4-yloxy)-benzamide | 255/257 |
| 4-(4-chloro-2-isoxazol-5-yl-phenoxy)-piperidine | 279/281 |
| 4-(5-chloro-2-methyl-phenoxy)-piperidine | 226/228 |
| 4-phenoxy-piperidine | 178 |
| 4-(2,4-dichloro-6-methyl-phenoxy)-piperidine | 260/262 |
| 4-(3-chloro-4-methyl-phenoxy)-piperidine | 226/228 |
| 5-chloro-2-(piperidin-4-yloxy)-benzonitrile | 237/239 |
| 4-(2,4-dichloro-3-methyl-phenoxy)-piperidine | 260/262 |
| 4-(2-ethyl-4-fluoro-phenoxy)-piperidine | 224 |
| 4-(4-methanesulfonyl-phenoxy)-piperidine | 297 |
| 4-(3,4-dichloro-2-methylphenoxy)-piperidine | 260/262 |

Method E

4-(3,4-Dichlorophenoxy)-4'-methyl-1,4'-bipiperidine dihydrochloride a) 1,1-Dimethylethyl 4'-cyano-4-(3,4-dichlorophenoxy)-[1,4'-bipiperidine]-1'carboxylate 4-(3,4-Dichlorophenoxypiperidine) (Method B step b; 500 mg) was dissolved in dichloroethane (2 ml) with 1-Boc-4-piperidone (446 mg). Titanium teraisopropoxide (0.85 ml) was added and the mixture was stirred overnight. The solvent was evaporated and toluene (5 ml) was added followed by diethylaluminium cyanide (3 ml of 1M solution in toluene). The mixture was stirred for 3 h, then ethyl acetate was added (5 ml) followed by water (0.5 ml) and the mixture was stirred for a further 2 h. The mixture was filtered through a GF filter paper, and evaporated to give the subtitle compound (912 mg; MS [M+H]+ (APCI+) 454/456). $^1$H NMR (399.98 MHz, CD$_3$OD) δ 1.36 (s, 9H), 1.57-1.77 (m, 4H), 1.90-1.99 (m, 2H), 2.04-2.12 (m, 2H), 2.44-2.52 (m, 2H), 2.77-2.87 (m, 2H), 3.02-3.13 (m, 2H), 3.82 (dt, 2H), 4.31-4.40 (m, 1H), 6.81 (dd, 1H), 7.02 (d, 1H), 7.29 (d, 1H).

b) 1,1-Dimethylethyl 4-(3,4-dichlorophenoxy)-4'-methyl-[1,4'-bipiperidine]-1'-carboxylate 1,1-Dimethylethyl 4'-cyano-4-(3,4-dichlorophenoxy)-[1,4'-bipiperidine]-1'-carboxylate (100 mg) was dissolved in THF (6 ml). Methyl magnesium bromide (3M in ether, 220 μl) was added and the mixture was stirred at RT for 2 h. Further methyl magnesium bromide (220 μl) was added and the solution was stirred for a further 60 h. Potassium carbonate solution (saturated aqueous) was added and the mixture was extracted with DCM. The organic phase was dried, filtered and evaporated to give the subtitle compound (100 mg; MS [M+H]$^+$ (APCI+) 443/445).

$^1$H NMR (299.945 MHz, CD$_3$OD) δ 1.01 (s, 3H), 1.47 (s, 9H), 1.69-1.84 (m, 4H), 1.97-2.08 (m, 2H), 2.42-2.52 (m, 2H), 2.81-2.92 (m, 2H), 3.36-3.42 (m, 2H), 3.45-3.57 (m, 2H), 3.62-3.89 (m, 2H), 4.32-4.41 (m, 1H), 6.89 (dd, 1H), 7.10 (d, 1H), 7.38 (d, 1H).

c) 4-(3,4-dichlorophenoxy)-4'-methyl-1,4'-bipiperidine dihydrochloride 1,1-Dimethylethyl 4-(3,4-dichlorophenoxy)-4'-methyl-[1,4'-bipiperidine]-1'-carboxylate (100 mg) was dissolved in ethanol (5 ml). Hydrogen chloride (2 ml of 4M in dioxan) was added and the solution was stirred overnight. Further hydrogen chloride solution (2 ml) was added and the mixture was stirred for a further 2 h. The solvents were evaporated to give the title compound (95 mg; MS [M+H]+ (APCI+) 343/345).

Method F trans Sodium 4-[4-(3,4-dichlorophenoxy)-1-piperidinyl]-cyclohexanecarboxylate a) Ethyl 4-[4-(3,4-dichlorophenoxy)-1-piperidinyl]-cyclohexanecarboxylate 4-(3,4-Dichlorophenoxy)piperidine (Method B, 1.44 g), ethyl 4-oxocyclohexanecarboxylate (1.0 g) and acetic acid (0.34 ml) were combined in THF 10 ml and the solution was cooled in ice. Sodium triacetoxy borohydride (1.45 g) was added and the mixture was stirred overnight and allowed to come to ambient temperature. The reaction mixture was poured onto a stirred saturated aq solution of sodium bicarbonate. The mixture was extracted with ethyl acetate thrice, the organic phases were washed with brine, dried, filtered and evaporated. The residue was purified on an SCX cartridge (International Sorbent Technology Isolute® Flash SCX-2), washed with methanol and then product eluted with 0.7M ammonia in methanol. Further purification by chromatography (silica, 90:9:1 DCM:methanol:triethylamine) gave the subtitle compound (1.59 g; MS [M+H]+ (APCI+) 400/402) as a mixture of cis/trans isomers.

$^1$H NMR (399.98 MHz, CD$_3$OD) δ 1.23 (t), 1.25 (t), 1.28-1.59 (m), 1.70-1.81 (m), 1.96-2.07 (m), 2.17-2.27 (m), 2.32-2.40 (m), 2.45-2.56 (m), 2.581-2.61 (m), 2.80-2.89 (m), 3.30 (quintet), 4.10 (q), 4.14 (q), 4.34-4.40 (m), 6.88 (dd), 6.88 (dd), 7.09 (d), 7.09 (d), 7.37 (d), 7.37 (d).

b) trans Sodium 4-[4-(3,4-dichlorophenoxy)-1-piperidinyl]-cyclohexanecarboxylate Ethyl 4-[4-(3,4-dichlorophenoxy)-1-piperidinyl]-cyclohexanecarboxylate (0.97 g) was added to a solution of sodium ethoxide in ethanol (prepared from sodium (1.28 g) and ethanol (100 ml)) the solution was heated to reflux overnight. Acetic acid was added and the solvent was evaporated. Ethyl acetate, water and sodium hydroxide were added to the residue and an insoluble white solid formed which was collected by filtration and dried in vacuo to give the sub-titled compound (469 mg; MS [M−Na]− (APCI−) 370/372) containing sodium acetate.

$^1$H NMR (399.98 MHz, CD$_3$OD) δ 1.27-1.38 (m, 2H), 1.46 (q, 2H), 1.72-1.81 (m, 2H), 1.95-2.09 (m, 7H), 2.40 (t, 1H), 2.55 (td, 2H), 2.84-2.91 (m, 2H), 4.39 (septet, 1H), 6.89 (dd, 1H), 7.10 (d, 1H), 7.37 (d, 1H).

Method G 4-(3,4-Dichlorophenoxy)-[1,4'-bipiperidine]-1'-sulfonamide 4-(3,4-Dichlorophenoxy)-1,4'-bipiperidine (5 g, 0.0152 mol) and sulfamide (1.45 g, 0.0152 mol) were stirred together in dioxan (150 ml) at reflux for 24 hours. The resulting mixture was cooled to ambient temperature, evaporated to dryness and the residue was triturated with ether to give the title compound as a tan solid (5 g; MS APCI 409/411 (M+H)).

$^1$H NMR (399.98 MHz, DMSO) δ 1.38-2.03 (m, 6H), 2.25-2.45 (m, 6H), 2.66-2.84 (m, 3H), 3.41-3.53 (m, 2H), 4.35-4.47 (m, 1H), 6.31-6.45 (m, 2H), 6.91-7.03 (m, 1H), 7.18-7.31 (m, 1H), 7.43-7.55 (m, 1H).

Method H 4-(3,4-Dichlorophenoxy)-[1,4'-bipiperidine]-1'-carboxamide.

4-(3,4-Dichlorophenoxy)-1,4'-bipiperidine (2.0 g) was dissolved in glacial acetic acid (0.608 ml), the solution was diluted with water (6 ml) and added with stirring to a solution of sodium cyanate (0.395 g) in warm water (3 ml). The reaction was allowed to stand for 30 mins. 2M Sodium hydroxide solution was added until the solution was alkaline. The resulting precipitate was collected and washed with water followed by dichloromethane and then dried to leave the sub-title compound (1.3 g; ES+ 372/374).

$^1$H NMR (399.98 MHz, DMSO) δ 1.20-1.31 (m, 2H), 1.51-1.61 (m, 2H), 1.62-1.69 (m, 2H), 1.88-1.95 (m, 2H), 2.32-2.44 (m, 3H), 2.55-2.64 (m, 2H), 2.70-2.77 (m, 2H), 3.92-3.99 (m, 2H), 4.37-4.44 (m, 1H), 5.86 (s, 2H), 6.95-6.99 (m, 1H), 7.24-7.25 (m, 1H), 7.49 (d, 1H).

Method I 2,4-Dichloro-3-fluorophenol a) N,N-Diethyl-4-chloro-3-fluorophenyl carbamate A solution of 4-chloro-3-fluorophenol (26.9 g) and diethylcarbamoyl chloride (25 g) in pyridine (100 ml) was heated to 100° C. for 12 h and then allowed to cool. Water (100 ml) was added and the product was extracted with diethylether/pentane (1:1) (50 ml×2). The combined organic extracts were washed with HCl (2M, 70 ml), NaOH (2M, 75 ml) and dried (MgSO$_4$), filtered and evaporated to give the subtitle compound as an oil (37.7 g)

$^1$H NMR δ (CDCl$_3$) 1.18-1.26 (6H, m), 3.35-3.44 (4H, m), 6.90 (1H, ddd), 6.99-7.02 (1H, m), 7.35 (1H, t)

b) N,N-Diethyl-2,4-dichloro-3-fluorophenyl carbamate

To a solution of N,N-diethyl-4-chloro-3-fluorophenyl carbamate (15 g) in THF (100 ml) and TMEDA (9.7 ml) at −90° C. was added secBuLi (1.3M, 49.5 ml) whilst maintaining the temperature between −80° C. and −90° C. The mixture was stirred at −80° C. for 2 h. 1,1,1,2,2,2-Hexachloroethane (17.39 g) as a solution in THF (50 ml) was added. During this period the reaction was allowed to warm to 0° C. Water (50 ml) was added and the product was extracted with pentane. The combined organic extracts were dried (MgSO$_4$) and filtered. Evaporation of solvent and purification by HPLC (Waters XTerra® column)(gradient (25% MeCN/NH3(aq) (0.1%) to 95% MeCN//NH3(aq) (0.1%)) gave the subtitle compound as an oil (9.3 g).

$^1$H NMR δ (CDCl$_3$) 1.19-1.32 (6h, m), 3.36-3.51 (4H, m), 7.03 (1H, dq), 7.26-7.33 (1H, m)

2,4-Dichloro-3-fluorophenol

N,N-Diethyl-2,4-dichloro-3-fluorophenyl carbamate (8.14 g) was dissolved in THF (17 ml). A solution of lithium aluminium hydride (33 ml of 1M in THF) was added dropwise and the resulting solution was stirred overnight. Ethanol was added followed by hydrochloric acid (2M, 17 ml). The resulting suspension was filtered and the solid was washed with ether. The phases were separated, the aqueous phase was extracted thrice with ether and the combined organic phases were dried (MgSO$_4$), filtered- and evaporated to give the title compound (3.4 g).

$^1$H NMR δ (CD$_3$OD) 6.65 (1H, dd), 7.11 (1H, t)

Method J 2,6-Dimethyl-benzenesulfonamide

To a solution of 2,6-dimethyl-benzenethiol (2 ml) in water (20 ml), chlorine gas was introduced over 15 minutes resulting in precipitation of an orange solid. The reaction was left to stir in a stoppered flask for a further 60 minutes. An excess of ammonia solution (0.88 sg) was added and the mixture was left to stir for 12 h. The reaction was evaporated to remove ammonia and then filtered. The solid was washed with water followed by iso-hexane to give the title compound.

MS [M–H]$^-$ (ES–) 184
$^1$H NMR δ (DMSO) 2.59 (6H, s), 7.18 (2H, d), 7.27 (2H, s), 7.30 (1H, t)

Method K trans 4-[4-(3,4-Dichlorophenoxy)-1-piperidinyl]-cyclohexanecarboxylic acid a) trans Ethyl 4-[4-(3,4-dichlorophenoxy)-1-piperidinyl]-cyclohexanecarboxylate Ethyl 4-[4-(3,4-dichlorophenoxy)-1-piperidinyl]-cyclohexanecarboxylate (method F, step a, 0.97 g) was added to a solution of sodium ethoxide prepared from sodium (1.28 g) and ethanol (100 ml). The resultant solution was heated under reflux for 18 h. Acetic acid (0.1 ml) was added and the solvent was evaporated. Ethyl acetate, water and sodium hydroxide were added to the residue and separated. The aqueous phase was extracted twice with ethyl acetate-methanol mixtures and the combined organic phases were washed with brine, dried (MgSO$_4$), filtered and evaporated to give the subtitle compound as an oil.

MS [M+H]$^+$ (APCI+) 400/402 $^1$H NMR of major isomer (ca 3.5:1 ratio) δ (acetone) 1.20 (3H, t), 1.27-1.46 (4H, m), 1.57 1.71 (3H, m), 1.84-1.90 (2H, m), 1.95-2.02 (4H, m), 2.15-2.23 (1H, m), 2.27-2.41 (2H, m), 2.46 (2H, ddd), 4.06 (2H, q), 4.40 (1H, septet), 6.95 (1H, dd), 7.15 (1H, d), 7.43 (1H, d)

b) trans 4-[4-(3,4-Dichlorophenoxy)-1-piperidinyl]-cyclohexanecarboxylic acid trans Ethyl 4-[4-(3,4-dichlorophenoxy)-1-piperidinyl]-cyclohexanecarboxylate (0.8 g) was dissolved in t-BuOH (180 ml) at 38° C. To this was added *Candia rugosa* lipase powder (3 g). This was stirred for 30 minutes then water (20 ml) was added over 4 h. The mixture was then stirred for 48 h and filtered. The enzyme was washed with 9:1 t-BuOH-water (2×20 ml) and the filtrate was evaporated. Ethyl acetate was added to the residue and then decanted. The resultant solid was dissolved in methanol/DMSO and was purified by HPLC (Waters XTerra® column with at-column dilution of sample) (gradient (5% MeCN/NH3(aq) (0.2%) to 40% MeCN//NH3(aq) (0.2%)] gave the title compound (0.44 g) as a white solid.

m.pt. 167-168° C. MS [M+H]$^+$ (ES+) 372/374 $^1$H NMR δ$_{(DMSO)}$1.19-1.36 (4H, m), 1.50-1.59 (2H, m), 1.78 (2H, d), 1.87-1.96 (4H, m), 2.09 (1H, td), 2.24-2.32 (1H, m), 2.38 (2H, td), 2.72 (2H, dt), 4.39 (1H, septet), 6.97 (1H, dd), 7.24 (1H, d), 7.49 (1H, d)

Method L 1,1-Dimethylethyl [4-(3,4-dichlorophenoxy)-1,4'-bipiperidin-1'-yl]sulfonylcarbamate tert-Butanol (0.48 ml) in dichloromethane (2 ml) was added to a solution of chlorosulfonylisocyanate (0.43 ml) in dichloromethane (5 ml) stirring at 0° C. The resulting solution was then added to a solution of 4-(3,4-dichlorophenoxy)-1,4'-bipiperidine (1.6 g) and triethylamine (0.77 ml) in dichloromethane (20 ml) at 0° C. After stirring at 0° C. for 2 h, the reaction mixture was washed with 0.1M hydrochloric acid (30 ml), dried (MgSO$_4$) and evaporated. The residue was triturated with diethylether (20 ml) to give the title compound as a white solid. (1.9 g)

$^1$H NMR δ$_{(DMSO)}$1.44 (9H, s), 1.64-1.77 (2H, m), 1.94-2.08 (2H, m), 2.15-2.27 (4H, m), 2.86 (2H, t), 3.03-3.18 (2H, m), 3.28-3.53 (3H, m), 3.76 (2H, d), 4.59-4.81 (1H, m), 6.99-7.11 (1H, m), 7.33-7.39 (1H, m), 7.52-7.58 (1H, m)

EXAMPLE 17

Pharmacological Analysis: Calcium Flux $[Ca^{2+}]_i$ Assay

Human Eosinophils

Human eosinophils were isolated from EDTA anticoagulated peripheral blood as previously described (Hansel et al., *J. Immunol. Methods*, 1991, 145, 105-110). The cells were resuspended (5×10$^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1%(v/v) DMSO. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

Compounds of the Examples were found to be antagonists if the increase in fluorescence induced by eotaxin (a selective CCR3 agonist) was inhibited in a concentration dependent manner. The concentration of antagonist required to inhibit the fluorescence by 50% can be used to determine the IC$_{50}$ for the antagonist at the CCR3 receptor.

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at 10×10$^6$ ml$^{-1}$ in RPMI containing 200 IU/ml penicillin, 200 μg/ml streptomycin sulfate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin 0.1 to 100 nM (a selective CCR3 agonist over this concentration range) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton ×100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Compounds of the Examples were found to be antagonists of eotaxin mediated human eosinophil chemotaxis if the concentration response to eotaxin was shifted to the right of the control curve. Measuring the concentration of eotaxin required to give 50% chemotaxis in the presence or absence of compounds enables the apparent affinity of the compounds at CCR3 to be calculated.

The invention claimed is:

1. A compound of formula (I):

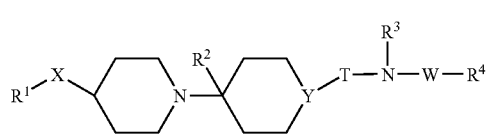

wherein:
T is C(O) or $S(O)_2$;
W is C(O) or $S(O)_2$;
X is $CH_2$, O or NH;
Y is N;
$R^1$ is optionally substituted aryl or optionally substituted heterocyclyl;
$R^2$ is hydrogen or $C_{1-6}$ alkyl;
$R^3$ is hydrogen;
$R^4$ is alkyl, optionally substituted aryl, optionally substituted aralkyl or optionally substituted heterocyclyl;
$R^5$ is hydrogen or $C_{1-6}$ alkyl;
wherein the foregoing aryl and heterocyclyl moieties are optionally substituted by: halogen, cyano, nitro, hydroxy, oxo, $S(O)_pR^{25}$, $OC(O)NR^6R^7$, $NR^8R^9$, $NR^{10}C(O)R^{11}$, $NR^{12}C(O)NR^{13}R^{14}$, $S(O)_2NR^{15}R^{16}$, $NR^{17}S(O)_2R^{18}$, $C(O)NR^{19}R^{20}$, $C(O)R^{21}$, $CO_2R^{22}$, $NR^{23}CO_2R^{24}$, $C_{1-6}$ alkyl, $CF_3$, $C_{1-6}$ alkoxy($C_{1-6}$)alkyl, $C_{1-6}$ alkoxy, $OCF_3$, $C_{1-6}$ alkoxy($C_{1-6}$)alkoxy, $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;
p and q are, independently, 0, 1 or 2;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, and $R^{23}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$, $S(O)_2(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$, $S(O)_2(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);
alternatively $NR^6R^7$, $NR^8R^9$, $NR^{13}R^{14}$, $NR^{15}R^{16}$, $NR^{19}R^{20}$ or $N(C_{1-4}$ alkyl$)_2$ may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen;
$R^{25}$, $R^{18}$ and $R^{24}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^6$ and $R^7$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^6$ and $R^7$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^6$ and $R^7$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^6$ and $R^7$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^6$ and $R^7$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);
or an N-oxide thereof; or a pharmaceutically acceptable salt thereof.

2. A compound as claimed in claim 1 wherein X is O.

3. A compound as claimed in claim 1 wherein $R^1$ is phenyl substituted with one or more of fluorine, chlorine, $C_{1-4}$ alkyl or $C_{1-4}$ alkoxy.

4. A compound as claimed in claim 1 wherein one of T and W is C(O) and the other is $S(O)_2$.

5. A compound as claimed in claim 1 wherein T is C(O).

6. A compound as claimed in claim 1 wherein W is $S(O)_2$.

7. A compound as claimed in claim 1 wherein $R^2$ is hydrogen or methyl.

8. A compound as claimed in claim 1 wherein $R^4$ is substituted phenyl, the substituents being chosen from those provided in claim 1.

9. A compound as claimed in claim 1 which is:
N-[[4-(2-Chloro-4-fluorophenoxy)[1,4'-bipiperidin]-1'-yl]carbonyl]-4-methyl benzenesulfonamide;

N-[[4-(2-Chloro-4-fluorophenoxy)[1,4'-bipiperidin]-1'-yl]carbonyl]-2-methyl benzenesulfonamide;
4-Chloro-N-[[4-(2-chloro-4-fluorophenoxy)[1,4'-bipiperidin]-1'-yl]carbonyl]benzenesulfonamide;
2-Chloro-N-[[4-(2-Chloro-4-fluorophenoxy)[1,4'-bipiperidin]-1'-yl]carbonyl]-benzenesulfonamide;
N-[[4-(2-Chloro-4-fluorophenoxy)[1,4'-bipiperidin]-1'-yl]carbonyl]-4-fluoro-benzenesulfonamide;
N-[[4-(2-Chloro-4-fluorophenoxy)[1,4'-bipiperidin]-1'-yl]carbonyl]-benzenesulfonamide;
N-[[4-(4-Chloro-2-methylphenoxy)[1,4'-bipiperidin]-1'-yl]carbonyl]-2-methyl benzenesulfonamide;
4-Chloro-N-[[4-(4-chloro-2-methylphenoxy)[1,4'-bipiperidin]-1'-yl]carbonyl]benzenesulfonamide;
2-Chloro-N-[[4-(4-chloro-2-methylphenoxy)[1,4'-bipiperidin]-1'-yl]carbonyl]benzenesulfonamide;
N-[[4-(4-Chloro-2-methylphenoxy)[1,4'-bipiperidin]-1'-yl]carbonyl]-4-fluoro benzenesulfonamide;
N-[[4-(4-Chloro-2-methylphenoxy)[1,4'-bipiperidin]-1'-yl]carbonyl]-4-methyl benzenesulfonamide;
N-[[4-(4-Chloro-2-methylphenoxy)[1,4'-bipiperidin]-1'-yl]carbonyl]-benzenesulfonamide;
N-[[4-(2,4-Dichloro-3-methylphenoxy)[1,4'-bipiperidin]-1'-yl]carbonyl]-2-methyl benzenesulfonamide;
N-[[4-(2,4-Dichloro-3-methylphenoxy)[1,4'-bipiperidin]-1'-yl]carbonyl]-4-methyl benzenesulfonamide;
2-Chloro-N-[[4-(2,4-dichloro-3-methylphenoxy)[1,4'-bipiperidin]-1'-yl]carbonyl]benzenesulfonamide;
4-Chloro-N-[[4-(2,4-dichloro-3-methylphenoxy)[1,4'-bipiperidin]-1'-yl]carbonyl]benzenesulfonamide;
N-[[4-(2,4-Dichloro-3-methylphenoxy)[1,4'-bipiperidin]-1'-yl]carbonyl]-4-fluoro benzenesulfonamide;
N-[[4-(2,4-Dichloro-3-methylphenoxy)[1,4'-bipiperidin]-1'-yl]carbonyl]-benzenesulfonamide;
N-[[4-(3,4-Dichloro-2-methylphenoxy)[1,4'-bipiperidin]-1'-yl]carbonyl]-2-methyl benzenesulfonamide;
N-[[4-(3,4-Dichloro-2-methylphenoxy)[1,4'-bipiperidin]-1'-yl]carbonyl]-4-methyl-benzenesulfonamide;
2-Chloro-N-[[4-(3,4-dichloro-2-methylphenoxy)[1,4'-bipiperidin]-1'-yl]carbonyl]benzenesulfonamide;
4-Chloro-N-[[4-(3,4-dichloro-2-methylphenoxy)[1,4'-bipiperidin]-1'-yl]carbonyl]benzenesulfonamide;
N-[[4-(3,4-Dichloro-2-methylphenoxy)[1,4'-bipiperidin]-1'-yl]carbonyl]-4-fluoro benzenesulfonamide;
N-[[4-(3,4-Dichloro-2-methylphenoxy)[1,4'-bipiperidin]-1'-yl]carbonyl]-benzenesulfonamide;
N-[[4-(3,4-Dichlorophenoxy)-4'-methyl[1,4'-bipiperidin]-1'-yl]carbonyl]-4-methyl benzenesulfonamide;
N-[[4-(3,4-Dichlorophenoxy)-4'-methyl[1,4'-bipiperidin]-1'-yl]carbonyl]-4-fluoro benzenesulfonamide;
N-[[4-(3,4-Dichlorophenoxy)-4'-methyl[1,4'-bipiperidin]-1'-yl]carbonyl]-2-methyl benzenesulfonamide;
4-Chloro-N-[[4-(3,4-dichlorophenoxy)-4'-methyl[1,4'-bipiperidin]-1'-yl]carbonyl]-benzenesulfonamide;
2-Chloro-N-[[4-(3,4-dichlorophenoxy)-4'-methyl[1,4'-bipiperidin]-1'-yl]carbonyl]benzenesulfonamide;
N-[[4-(3,4-Dichlorophenoxy)-4'-methyl[1,4'-bipiperidin]-1'-yl]carbonyl]-3-trifluoromethyl benzenesulfonamide;
3-Cyano-N-[[4-(3,4-dichlorophenoxy)-4'-methyl[1,4'-bipiperidin]-1'-yl]carbonyl]benzenesulfonamide;
N-[[4-(3,4-Dichlorophenoxy)[1,4'-bipiperidin]-1'-yl]carbonyl]-benzenemethanesulfonamide;
N-[[4-(3,4-Dichlorophenoxy)[1,4'-bipiperidin]-1'-yl]carbonyl]-methanesulfonamide;
N-[[4-(4-Chloro-3-methylphenoxy)[1,4'-bipiperidin]-1'-yl]carbonyl]-2-methyl benzenesulfonamide;
N-[[4-(4-Chloro-3-methylphenoxy)[1,4'-bipiperidin]-1'-yl]carbonyl]-4-methyl benzenesulfonamide;
4-Chloro-N-[[4-(4-chloro-3-methylphenoxy)[1,4'-bipiperidin]-1'-yl]carbonyl]benzenesulfonamide;
N-[[4-[(3,4-Dichlorophenyl)methyl][1,4'-bipiperidin]-1'-yl]carbonyl]-4-methyl benzenesulfonamide;
4-Chloro-N-[[4-[(3,4-dichlorophenyl)methyl][1,4'-bipiperidin]-1'-yl]carbonyl]benzenesulfonamide;
N-[[4-[(3,4-Dichlorophenyl)amino]-[1,4'-bipiperidin]-1'-yl]carbonyl]-4-methyl benzenesulfonamide;
4-Chloro-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-4-methyl-benzenesulfonamide;
N-[[4-(3,4-Dichlorophenoxy)[1,4'-bipiperidin]-1'-yl]carbonyl]-2-methyl-benzenesulfonamide;
3-Bromo-N-[[4-(3,4-dichlorophenoxy)[1,4'-bipiperidin]-1'-yl]carbonyl]-benzenesulfonamide;
4-Bromo-N-[[4-(3,4-dichlorophenoxy)[1,4'-bipiperidin]-1'-yl]carbonyl]-benzenesulfonamide;
3,5-Dichloro-N-[[4-(3,4-dichlorophenoxy)[1,4'-bipiperidin]-1'-yl]carbonyl]benzenesulfonamide;
3-Cyano-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-2,5-dimethoxy benzenesulfonamide;
N-[[4-(3,4-Dichlorophenoxy)[1,4'-bipiperidin]-1'-yl]carbonyl]-3,4-dimethoxy-benzenesulfonamide;
N-[[4-(3,4-Dichlorophenoxy)[1,4'-bipiperidin]-1'-yl]carbonyl]-4-(3,3-dimethyl-2-oxo-1 azetidinyl)-benzenesulfonamide;
N-[[4-(3,4-Dichlorophenoxy)[1,4'-bipiperidin]-1'-yl]carbonyl]-4-(4,5-dihydro-3-methyl-5-oxo-1H-pyrazol-1-yl)-benzenesulfonamide;
N-[[4-(3,4-Dichlorophenoxy)[1,4'-bipiperidin]-1'-yl]carbonyl]-3-(4,5-dihydro-3-methyl-5-oxo-1H-pyrazol-1-yl)-benzenesulfonamide;
N-[[4-(3,4-Dichlorophenoxy)[1,4'-bipiperidin]-1'-yl]carbonyl]-4-hydroxy-benzenesulfonamide;
N-[[4-(3,4-Dichlorophenoxy)[1,4'-bipiperidin]-1'-yl]carbonyl]-3-(trifluoromethyl)benzenesulfonamide;
N-[[4-(3,4-Dichlorophenoxy)[1,4'-bipiperidin]-1'-yl]carbonyl]-benzenesulfonamide;
4-[[[[4-(3,4-Dichlorophenoxy)[1,4'-bipiperidin]-1'-yl]carbonyl]amino]sulfonyl]-benzoic acid, methyl ester;
2-Bromo-N-[[4-(3,4-dichlorophenoxy)[1,4'-bipiperidin]-1'-yl]carbonyl]-benzenesulfonamide;
N-[5-[[[[4-(3,4-Dichlorophenoxy)[1,4'-bipiperidin]-1'-yl]carbonyl]amino]sulfonyl]-1,3,4 thiadiazol-2-yl]-acetamide;
N-[[4-(3,4-Dichlorophenoxy)[1,4'-bipiperidin]-1'-yl]carbonyl]-5-(dimethylamino)-1 naphthalenesulfonamide;
N-[[4-(3,4-Dichlorophenoxy)[1,4'-bipiperidin]-1'-yl]carbonyl]-2-naphthalenesulfonamide;
N-[[4-(3,4-Dichlorophenoxy)[1,4'-bipiperidin]-1'-yl]carbonyl]-2,4-dimethyl-5 thiazolesulfonamide;
N-[[4-(3,4-Dichlorophenoxy)[1,4'-bipiperidin]-1'-yl]carbonyl]-2-(1-piperidinyl)-3 pyridinesulfonamide;
5-Chloro-N-[[4-(3,4-dichlorophenoxy)[1,4'-bipiperidin]-1'-yl]carbonyl]-2 thiophenesulfonamide;
5-Bromo-N-[[4-(3,4-dichlorophenoxy)[1,4'-bipiperidin]-1'-yl]carbonyl]-2 thiophenesulfonamide;
N-[[4-(3,4-Dichlorophenoxy)[1,4'-bipiperidin]-1'-yl]carbonyl]tetrahydro-3 thiophenesulfonamide; 1,1-dioxide
4,5-Dichloro-N-[[4-(3,4-dichlorophenoxy)[1,4'-bipiperidin]-1'-yl]carbonyl]-2 thiophenesulfonamide;

4-Chloro-N-[[4-(3,4-dichlorophenoxy)[1,4'-bipiperidin]-1'-yl]carbonyl]-2,5-dimethyl benzenesulfonamide;
4-n-Butyl-N-[[4-(3,4-dichlorophenoxy)[1,4'-bipiperidin]-1'-yl]carbonyl]-benzenesulfonamide;
2,5-Dichloro-N-[[4-(3,4-dichlorophenoxy)[1,4'-bipiperidin]-1'-yl]carbonyl]-3 thiophenesulfonamide;
4-n-Butoxy-N-[[4-(3,4-dichlorophenoxy)[1,4'-bipiperidin]-1'-yl]carbonyl]-benzenesulfonamide;
N-[[4-(3,4-Dichlorophenoxy)[1,4'-bipiperidin]-1'-yl]carbonyl]-2-(trifluoromethoxy)benzenesulfonamide;
N-[[4-(3,4-Dichlorophenoxy)[1,4'-bipiperidin]-1'-yl]carbonyl]-1-methyl-1H-imidazole-4 sulfonamide;
5-Amino-N-[[4-(3,4-dichlorophenoxy)[1,4'-bipiperidin]-1'-yl]carbonyl]-1,3,4-thiadiazole-2 sulfonamide;
4-Bromo-N-[[4-(3,4-dichlorophenoxy)[1,4'-bipiperidin]-1'-yl]carbonyl]-2 thiophenesulfonamide;
N-[[4-(3,4-Dichlorophenoxy)[1,4'-bipiperidin]-1'-yl]carbonyl]-2-(4-morpholinyl)-3 pyridinesulfonamide;
6-Bromo-N-[[4-(3,4-dichlorophenoxy)[1,4'-bipiperidin]-1'-yl]carbonyl]-3-pyridinesulfonamide;
N-[[4-(3,4-Dichlorophenoxy)[1,4'-bipiperidin]-1'-yl]carbonyl]-4-(1,1-dimethylethyl)benzenesulfonamide;
N-[[4-(3,4-Dichlorophenoxy)[1,4'-bipiperidin]-1'-yl]carbonyl]-5-methyl-2-pyridinesulfonamide;
N-[[4-(3,4-Dichlorophenoxy)[1,4'-bipiperidin]-1'-yl]carbonyl]-2,5-difluoro benzenesulfonamide;
N-[[4-(3,4-Dichlorophenoxy)[1,4'-bipiperidin]-1'-yl]carbonyl]-4-(trifluoromethoxy)benzenesulfonamide;
N-[[4-(3,4-Dichlorophenoxy)[1,4'-bipiperidin]-1'-yl]carbonyl]-2,4,5-trifluoro benzenesulfonamide;
5-Chloro-N-[[4-(3,4-dichlorophenoxy)[1,4'-bipiperidin]-1'-yl]carbonyl]-2,4-difluoro benzenesulfonamide;
4-Chloro-N-[[4-(3,4-dichlorophenoxy)[1,4'-bipiperidin]-1'-yl]carbonyl]-2,5-difluoro benzenesulfonamide;
3-Chloro-N-[[4-(3,4-dichlorophenoxy)[1,4'-bipiperidin]-1'-yl]carbonyl]-5-fluoro-2-methyl benzenesulfonamide;
N-[[4-(2,4-dichloro-3-methylphenoxy)[1,4'-bipiperidin]-1'-yl]carbonyl]-4-fluoro-benzenesulfonamide;
2-chloro-N-[[4-(2,4-dichloro-3-methylphenoxy)[1,4'-bipiperidin]-1'-yl]carbonyl]-benzenesulfonamide;
N-[[4-(3,4-dichloro-2-methylphenoxy)[1,4'-bipiperidin]-1'-yl]carbonyl]-4-methyl-benzenesulfonamide;
2-chloro-N-[[4-(3,4-dichloro-2-methylphenoxy)[1,4'-bipiperidin]-1'-yl]carbonyl]-benzenesulfonamide;
N-[[4-(4-chlorophenoxy)[1,4'-bipiperidin]-1'-yl]carbonyl]-4-methyl-benzenesulfonamide;
N-[[4-(2,4-dichloro-3-methylphenoxy)[1,4'-bipiperidin]-1'-yl]carbonyl]-2-methyl-benzenesulfonamide;
N-[[4-(2,4-dichloro-3-fluorophenoxy)[1,4'-bipiperidin]-1'-yl]carbonyl]-4-methyl-benzenesulfonamide;
N-[[4-(4-chloro-2-methylphenoxy)[1,4'-bipiperidin]-1'-yl]carbonyl]-2-methyl-benzenesulfonamide;
2-chloro-N-[[4-(4-chloro-2-methylphenoxy)[1,4'-bipiperidin]-1'-yl]carbonyl]-benzenesulfonamide;
4-chloro-N-[[4-(4-chloro-2-methylphenoxy)[1,4'-bipiperidin]-1'-yl]carbonyl]-benzenesulfonamide;
N-[[4-(2,4-dichlorophenoxy)[1,4'-bipiperidin]-1'-yl]carbonyl]-4-methyl-benzenesulfonamide;
N-[[4-(3-chlorophenoxy)[1,4'-bipiperidin]-1'-yl]carbonyl]-4-methyl-benzenesulfonamide;
2-chloro-N-[[4-(3-chlorophenoxy)[1,4'-bipiperidin]-1'-yl]carbonyl]-benzenesulfonamide;
N-[[4-(3-chlorophenoxy)[1,4'-bipiperidin]-1'-yl]carbonyl]-benzenesulfonamide;
2-chloro-N-[[4-(3-chloro-2-methylphenoxy)[1,4'-bipiperidin]-1'-yl]carbonyl]-benzenesulfonamide;
N-[[4-(2-chloro-4-fluorophenoxy)[1,4'-bipiperidin]-1'-yl]carbonyl]-2-methyl-benzenesulfonamide;
2-chloro-N-[[4-(2,4-dichloro-3-fluorophenoxy)[1,4'-bipiperidin]-1'-yl]carbonyl]-benzenesulfonamide;
4-chloro-N-[[4-(2,4-dichloro-3-fluorophenoxy)[1,4'-bipiperidin]-1'-yl]carbonyl]-benzenesulfonamide;
N-[[4-(2,4-dichloro-3-fluorophenoxy)[1,4'-bipiperidin]-1'-yl]carbonyl]-2-methyl-benzenesulfonamide;
2-chloro-N-[[4-(4-chlorophenoxy)[1,4'-bipiperidin]-1'-yl]carbonyl]-benzenesulfonamide;
4-chloro-N-[[4-(4-chlorophenoxy)[1,4'-bipiperidin]-1'-yl]carbonyl]-benzenesulfonamide;
N-[[4-(4-chlorophenoxy)[1,4'-bipiperidin]-1'-yl]carbonyl]-2-methyl-benzenesulfonamide;
2-chloro-N-[[4-(2,4-dichlorophenoxy)[1,4'-bipiperidin]-1'-yl]carbonyl]-benzenesulfonamide;
4-chloro-N-[[4-(2,4-dichlorophenoxy)[1,4'-bipiperidin]-1'-yl]carbonyl]-benzenesulfonamide;
N-[[4-(2,4-dichlorophenoxy)[1,4'-bipiperidin]-1'-yl]carbonyl]-2-methyl-benzenesulfonamide;
2-chloro-N-[[4-(3,4-difluorophenoxy)[1,4'-bipiperidin]-1'-yl]carbonyl]-benzenesulfonamide;
N-[[4-(3,4-difluorophenoxy)[1,4'-bipiperidin]-1'-yl]carbonyl]-2-methyl-benzenesulfonamide;
N-[[4-(3,4-difluorophenoxy)[1,4'-bipiperidin]-1'-yl]carbonyl]-4-methyl-benzenesulfonamide;
N-[[4-(3-chloro-2-methylphenoxy)[1,4'-bipiperidin]-1'-yl]carbonyl]-4-methyl-benzenesulfonamide;
N-[[4-(3-chloro-2-methylphenoxy)[1,4'-bipiperidin]-1'-yl]carbonyl]-benzenesulfonamide;
3-chloro-N-[[4-(3,4-dichlorophenoxy)[1,4'-bipiperidin]-1'-yl]carbonyl]-benzenesulfonamide;
N-[[4-(3,4-dichlorophenoxy)[1,4'-bipiperidin]-1'-yl]carbonyl]-4-methoxy-benzenesulfonamide;
N-[[4-(3,4-dichlorophenoxy)[1,4'-bipiperidin]-1'-yl]carbonyl]-2,4,5-trifluoro-benzenesulfonamide;
N-[[4-(3,4-dichlorophenoxy)[1,4'-bipiperidin]-1'-yl]carbonyl]-2,5-difluoro-benzenesulfonamide;
N-[[4-(3,4-dichlorophenoxy)[1,4'-bipiperidin]-1'-yl]carbonyl]-4-(dimethylamino)-benzenesulfonamide;
N-[[4-(3,4-dichlorophenoxy)[1,4'-bipiperidin]-1'-yl]carbonyl]-2-methoxy-benzenesulfonamide;
4-bromo-N-[[4-(3,4-dichlorophenoxy)[1,4'-bipiperidin]-1'-yl]carbonyl]-benzenesulfonamide;
3,5-dichloro-N-[[4-(3,4-dichlorophenoxy)[1,4'-bipiperidin]-1'-yl]carbonyl]-benzenesulfonamide;
Methyl 2-[[[[4-(3,4-dichlorophenoxy)[1,4'-bipiperidin]-1'-yl]carbonyl]amino]sulfonyl]-benzoate;
2-bromo-N-[[4-(3,4-dichlorophenoxy)[1,4'-bipiperidin]-1'-yl]carbonyl]-benzenesulfonamide;
5-chloro-N-[[4-(3,4-dichlorophenoxy)[1,4'-bipiperidin]-1'-yl]carbonyl]-2-thiophenesulfonamide;
4,5-dichloro-N-[[4-(3,4-dichlorophenoxy)[1,4'-bipiperidin]-1'-yl]carbonyl]-2-thiophenesulfonamide;
4-chloro-N-[[4-(3,4-dichlorophenoxy)[1,4'-bipiperidin]-1'-yl]carbonyl]-2,5-dimethyl-benzenesulfonamide;
2,5-dichloro-N-[[4-(3,4-dichlorophenoxy)[1,4'-bipiperidin]-1'-yl]carbonyl]-3-thiophenesulfonamide;
N-[[4-(3,4-dichlorophenoxy)[1,4'-bipiperidin]-1'-yl]carbonyl]-2-(trifluoromethoxy)-benzenesulfonamide;
4-bromo-N-[[4-(3,4-dichlorophenoxy)[1,4'-bipiperidin]-1'-yl]carbonyl]-2-thiophenesulfonamide;
N-[[4-(3,4-dichlorophenoxy)[1,4'-bipiperidin]-1'-yl]carbonyl]-4-(trifluoromethoxy)-benzenesulfonamide;
5-chloro-N-[[4-(3,4-dichlorophenoxy)[1,4'-bipiperidin]-1'-yl]carbonyl]-2,4-difluoro-benzenesulfonamide;

4-chloro-N-[[4-(3,4-dichlorophenoxy)[1,4'-bipiperidin]-1'-yl]carbonyl]-2,5-difluoro-benzenesulfonamide;
3-chloro-N-[[4-(3,4-dichlorophenoxy)[1,4'-bipiperidin]-1'-yl]carbonyl]-5-fluoro-2-methyl-benzenesulfonamide;
N-[[4-(3,4-dichlorophenoxy)[1,4'-bipiperidin]-1'-yl]carbonyl]-2,6-dimethyl-benzenesulfonamide;
N-[[4-(3,4-Dichlorophenoxy)[1,4'-bipiperidin]-1'-yl]carbonyl]-2-propanesulfonamide;
4-(3,4-Dichlorophenoxy)-N-(4-methylbenzoyl)-[1,4'-bipiperidine]-1'-sulfonamide;
4-(3,4-dichlorophenoxy)-N-(4-fluorobenzoyl)-[1,4'-bipiperidine]-1'-sulfonamide;
N-(4-chlorobenzoyl)-4-(3,4-dichlorophenoxy)-[1,4'-bipiperidine]-1'-sulfonamide;
4-(3,4-dichlorophenoxy)-N-(4-methylbenzoyl)-[1,4'-bipiperidine]-1'-sulfonamide;
4-(3,4-dichlorophenoxy)-N-[4-(dimethylamino)benzoyl]-[1,4'-bipiperidine]-1'-sulfonamide;
4-(3,4-dichlorophenoxy)-N-(4-ethylbenzoyl)-[1,4'-bipiperidine]-1'-sulfonamide;
4-(3,4-dichlorophenoxy)-N-(2-methoxybenzoyl)-[1,4'-bipiperidine]-1'-sulfonamide;
4-(3,4-dichlorophenoxy)-N-(4-methoxybenzoyl)-[1,4'-bipiperidine]-1'-sulfonamide;
N-(2-chlorobenzoyl)-4-(3,4-dichlorophenoxy)-[1,4'-bipiperidine]-1'-sulfonamide;
4-(3,4-dichlorophenoxy)-N-[3-(methylsulfonyl)benzoyl]-[1,4'-bipiperidine]-1'-sulfonamide;
N-(3-cyanobenzoyl)-4-(3,4-dichlorophenoxy)-[1,4'-bipiperidine]-1'-sulfonamide;
4-(4-chloro-2-methylphenoxy)-N-(4-fluorobenzoyl)-[1,4'-bipiperidine]-1'-sulfonamide;
N-(4-chlorobenzoyl)-4-(4-chloro-2-methylphenoxy)-[1,4'-bipiperidine]-1'-sulfonamide;
4-(4-chloro-2-methylphenoxy)-N-(4-methylbenzoyl)-[1,4'-bipiperidine]-1'-sulfonamide;
4-(4-chloro-2-methylphenoxy)-N-[4-(dimethylamino)benzoyl]-[1,4'-bipiperidine]-1'-sulfonamide;
4-(4-chloro-2-methylphenoxy)-N-(4-ethylbenzoyl)-[1,4'-bipiperidine]-1'-sulfonamide;
4-(4-chloro-2-methylphenoxy)-N-(2-methoxybenzoyl)-[1,4'-bipiperidine]-1'-sulfonamide;
4-(4-chloro-2-methylphenoxy)-N-(4-methoxybenzoyl)-[1,4'-bipiperidine]-1'-sulfonamide;
N-(2-chlorobenzoyl)-4-(4-chloro-2-methylphenoxy)-[1,4'-bipiperidine]-1'-sulfonamide;
4-(4-chloro-2-methylphenoxy)-N-[3-(methylsulfonyl)benzoyl]-[1,4'-bipiperidine]-1'-sulfonamide;
4-(4-chloro-2-methylphenoxy)-N-(3-cyanobenzoyl)-[1,4'-bipiperidine]-1'-sulfonamide;
4-(2,4-dichloro-3-methylphenoxy)-N-(4-fluorobenzoyl)-[1,4'-bipiperidine]-1'-sulfonamide;
N-(4-chlorobenzoyl)-4-(2,4-dichloro-3-methylphenoxy)-[1,4'-bipiperidine]-1'-sulfonamide;
4-(2,4-dichloro-3-methylphenoxy)-N-(4-methylbenzoyl)-[1,4'-bipiperidine]-1'-sulfonamide;
4-(2,4-dichloro-3-methylphenoxy)-N-[4-(dimethylamino)benzoyl]-[1,4'-bipiperidine]-1'-sulfonamide;
4-(2,4-dichloro-3-methylphenoxy)-N-(4-ethylbenzoyl)-[1,4'-bipiperidine]-1'-sulfonamide;
4-(2,4-dichloro-3-methylphenoxy)-N-(2-methoxybenzoyl)-[1,4'-bipiperidine]-1'-sulfonamide;
4-(2,4-dichloro-3-methylphenoxy)-N-(4-methoxybenzoyl)-[1,4'-bipiperidine]-1'-sulfonamide;
N-(2-chlorobenzoyl)-4-(2,4-dichloro-3-methylphenoxy)-[1,4'-bipiperidine]-1'-sulfonamide;
4-(2,4-dichloro-3-methylphenoxy)-N-[3-(methylsulfonyl)benzoyl]-[1,4'-bipiperidine]-1'-sulfonamide;
N-(3-cyanobenzoyl)-4-(3,4-dichlorophenoxy)-[1,4'-bipiperidine]-1'-sulfonamide;
4-(3,4-dichloro-2-methylphenoxy)-N-(4-fluorobenzoyl)-[1,4'-bipiperidine]-1'-sulfonamide;
N-(4-chlorobenzoyl)-4-(3,4-dichloro-2-methylphenoxy)-[1,4'-bipiperidine]-1'-sulfonamide;
4-(3,4-dichloro-2-methylphenoxy)-N-(4-methylbenzoyl)-[1,4'-bipiperidine]-1'-sulfonamide;
4-(3,4-dichloro-2-methylphenoxy)-N-[4-(dimethylamino)benzoyl]-[1,4'-bipiperidine]-1'-sulfonamide;
4-(3,4-dichloro-2-methylphenoxy)-N-(4-ethylbenzoyl)-[1,4'-bipiperidine]-1'-sulfonamide;
4-(3,4-dichloro-2-methylphenoxy)-N-(2-methoxybenzoyl)-[1,4'-bipiperidine]-1'-sulfonamide;
4-(3,4-dichloro-2-methylphenoxy)-N-(4-methoxybenzoyl)-[1,4'-bipiperidine]-1'-sulfonamide;
N-(2-chlorobenzoyl)-4-(3,4-dichloro-2-methylphenoxy)-[1,4'-bipiperidine]-1'-sulfonamide;
4-(3,4-dichloro-2-methylphenoxy)-N-[3-(methylsulfonyl)benzoyl]-[1,4'-bipiperidine]-1'-sulfonamide;
N-(3-cyanobenzoyl)-4-(3,4-dichloro-2-methylphenoxy)-[1,4'-bipiperidine]-1'-sulfonamide;
N-benzoyl-4-(3,4-dichloro-2-methylphenoxy)-[1,4'-bipiperidine]-1'-sulfonamide;
N-benzoyl-4-(2,4-dichlorophenoxy)-[1,4'-bipiperidine]-1'-sulfonamide;
N-(3-cyanobenzoyl)-4-(3,4-dichlorophenoxy)-[1,4'-bipiperidine]-1'-sulfonamide;
4-(3,4-dichlorophenoxy)-N-(4-fluorobenzoyl)-[1,4'-bipiperidine]-1'-sulfonamide;
4-(3,4-dichlorophenoxy)-N-[3-(methylsulfonyl)benzoyl]-[1,4'-bipiperidine]-1'-sulfonamide;
4-(4-chloro-2-methylphenoxy)-N-[3-(methylsulfonyl)benzoyl]-[1,4'-bipiperidine]-1'-sulfonamide;
N-(2-chlorobenzoyl)-4-(3,4-dichlorophenoxy)-[1,4'-bipiperidine]-1'-sulfonamide;
N-(4-chlorobenzoyl)-4-(3,4-dichlorophenoxy)-[1,4'-bipiperidine]-1'-sulfonamide;
N-(4-chlorobenzoyl)-4-(4-chloro-2-methylphenoxy)-[1,4'-bipiperidine]-1'-sulfonamide;
4-(3,4-dichlorophenoxy)-N-(2-methoxybenzoyl)-[1,4'-bipiperidine]-1'-sulfonamide;
4-(3,4-dichlorophenoxy)-N-(4-methoxybenzoyl)-[1,4'-bipiperidine]-1'-sulfonamide;
4-(3,4-dichlorophenoxy)-N-(4-methylbenzoyl)-[1,4'-bipiperidine]-1'-sulfonamide;
4-(3,4-dichlorophenoxy)-N-[(1,2-dihydro-1-oxo-4-isoquinolinyl)carbonyl]-[1,4'-bipiperidine]-1'-sulfonamide;
N-(cyclohexylcarbonyl)-4-(3,4-dichlorophenoxy)-[1,4'-bipiperidine]-1'-sulfonamide;
4-(3,4-dichlorophenoxy)-N-(2-methyl-1-oxopropyl)-[1,4'-bipiperidine]-1'-sulfonamide;
4-(3,4-dichlorophenoxy)-N-(2-phenylacetyl)-[1,4'-bipiperidine]-1'-sulfonamide;
N-[[4-(3,4-dichlorophenoxy)[1,4'-bipiperidin]-1'-yl]carbonyl]-2-propanesulfonamide;
4-(3,4-Dichlorophenoxy)-N-(2-methylbenzoyl)-[1,4'-bipiperidine]-1'-carboxamide;
4-(3,4-Dichlorophenoxy)-N-(4-methylbenzoyl)-[1,4'-bipiperidine]-1'-carboxamide;
4-(3,4-Dichlorophenoxy)-N-(4-chlorobenzoyl)-[1,4'-bipiperidine]-1'-carboxamide;
4-(3,4-Dichlorophenoxy)-N-benzoyl-[1,4'-bipiperidine]-1'-carboxamide;

4-(3,4-Dichlorophenoxy)-N-[(4-methylphenyl)sulfonyl]-[1,4'-bipiperidine]-1'-sulfonamide;

4-(3,4-dichlorophenoxy)-N-[[4-(1,1-dimethylethyl)phenyl]sulfonyl]-[1,4'-bipiperidine]-1'-sulfonamide;

[4-(3,4-dichlorophenoxy)-N-(phenylsulfonyl)-1,4'-bipiperidine]-1'-sulfonamide.

* * * * *